US007960541B2

(12) United States Patent
Wilton et al.

(10) Patent No.: US 7,960,541 B2
(45) Date of Patent: Jun. 14, 2011

(54) ANTISENSE OLIGONUCLEOTIDES FOR INDUCING EXON SKIPPING AND METHODS OF USE THEREOF

(75) Inventors: Stephen Donald Wilton, Applecross (AU); Sue Fletcher, Bayswater (AU); Graham McClorey, Bayswater (AU)

(73) Assignee: The University of Western Australia, Crawley (AU)

( * ) Notice: Subject to any disclaimer, the term of this patent is extended or adjusted under 35 U.S.C. 154(b) by 0 days.

(21) Appl. No.: 12/860,078

(22) Filed: Aug. 20, 2010

(65) Prior Publication Data

US 2011/0046203 A1    Feb. 24, 2011

Related U.S. Application Data

(63) Continuation of application No. 11/570,691, filed as application No. PCT/AU2005/000943 on Jun. 28, 2005, now Pat. No. 7,807,816.

(30) Foreign Application Priority Data

Jun. 28, 2004  (AU) ............................... 2004903474

(51) Int. Cl.
*A06K 21/00* (2006.01)
(52) U.S. Cl. .................. 536/24.5; 536/24.1; 536/24.31; 435/6; 435/325; 435/375; 514/44
(58) Field of Classification Search .................. None
See application file for complete search history.

(56) References Cited

U.S. PATENT DOCUMENTS

| | | | |
|---|---|---|---|
| 5,034,506 A | 7/1991 | Summerton et al. | 528/391 |
| 5,142,047 A | 8/1992 | Summerton et al. | 544/118 |
| 5,149,797 A | 9/1992 | Pederson et al. | 536/27 |
| 5,166,315 A | 11/1992 | Summerton et al. | 528/406 |
| 5,185,444 A | 2/1993 | Summerton et al. | 544/81 |
| 5,217,866 A | 6/1993 | Summerton et al. | 435/6 |
| 5,506,337 A | 4/1996 | Summerton et al. | 528/391 |
| 5,521,063 A | 5/1996 | Summerton et al. | 435/6 |
| 5,627,274 A | 5/1997 | Kole et al. | 536/23.1 |
| 5,665,593 A | 9/1997 | Kole et al. | 435/375 |
| 5,892,023 A | 4/1999 | Pirotzky et al. | 536/24.5 |
| 6,210,892 B1 | 4/2001 | Bennett et al. | 435/6 |
| 6,656,732 B1 | 12/2003 | Bennett et al. | 435/375 |
| 6,784,291 B2 | 8/2004 | Iversen et al. | 536/24.5 |
| 7,070,807 B2 | 7/2006 | Mixson | 424/484 |
| 7,163,695 B2 | 1/2007 | Mixson | 424/486 |
| 7,250,289 B2 | 7/2007 | Zhou | 435/287.2 |
| 7,468,418 B2 | 12/2008 | Iversen et al. | 530/300 |
| 7,807,816 B2 | 10/2010 | Wilton et al. | 536/24.5 |
| 2003/0224353 A1 | 12/2003 | Stein et al. | 435/5 |
| 2004/0248833 A1 | 12/2004 | Emanuele et al. | 514/44 |
| 2007/0082861 A1 | 4/2007 | Matsuo et al. | 514/44 |
| 2010/0130591 A1 | 5/2010 | Sazani et al. | 514/44 A |
| 2011/0015253 A1 | 1/2011 | Wilton et al. | 514/44 A |
| 2011/0015258 A1 | 1/2011 | Wilton et al. | 514/44 R |

FOREIGN PATENT DOCUMENTS

| | | |
|---|---|---|
| AU | 780517 | 11/2001 |
| AU | 2003284638 A1 | 6/2004 |
| CA | 2 507 125 A1 | 6/2004 |
| EP | 1 191 097 A1 | 3/2002 |
| EP | 1 766 010 A0 | 3/2007 |
| WO | WO 94/02595 A1 | 2/1994 |
| WO | WO 96/10391 A1 | 4/1996 |
| WO | WO 96/10392 A1 | 4/1996 |
| WO | WO 97/30067 A1 | 8/1997 |
| WO | WO 97/34638 A1 | 9/1997 |
| WO | WO 00/44897 A1 | 8/2000 |
| WO | WO 01/49775 A2 | 7/2001 |
| WO | WO 01/83740 A2 | 11/2001 |
| WO | WO 02/024906 A1 | 3/2002 |
| WO | WO 2004/048570 A1 | 6/2004 |
| WO | WO 2004/083432 A1 | 9/2004 |
| WO | WO 2004/083446 A2 | 9/2004 |
| WO | WO 2006/000057 A1 | 1/2006 |

OTHER PUBLICATIONS

Aartsma-Rus et al., "Antisense-Induced Multiexon Skipping for Duchenne Muscular Dystrophy Makes More Sense," *Am. J. Hum. Genet.* 74:83-92, 2004.
Aartsma-Rus et al., "Therapeutic antisense-induced exon skipping in cultured muscle cells from six different DMD patients," *Human Molecular Genetics* 12(8):907-914, 2003.
Aartsma-Rus et al., "Targeted exon skipping as a potential gene correction therapy for Duchenne muscular dystrophy," *Neuromuscular Disorders* 12:S71-S77, 2002.
Abbs et al., "A convenient multiplex PCR system for the detection of dystrophin gene deletions: a comparative analysis with cDNA hybridisation shows mistyping by both methods," *J. Med. Genet.* 28:304-311, 1991.
Agrawal et al., "Oligodeoxynucleoside phosphoramidates and phosphorothioates as inhibitors of human immunodeficiency virus," *Proc. Natl. Acad. Sci. USA* 85:7079-7083, Oct. 1988.
Akhtar et al., "Cellular uptake and intracellular fate of antisense oligonucleotides," *Trends in Cell Biology* 2:139-144, May 1992.
Akhtar, Saghir, (ed.), *Delivery Strategies for Antisense Oligonucleotide Therapeutics*, CRC Press, Boca Raton, Florida, 1995.
Anderson, "Human Gene Therapy," *Science* 256:808-813, May 8, 1992.
Berge et al., "Pharmaceutical Salts," *Journal of Pharmaceutical Sciences* 66(1):1-19, Jan. 1977.
Brown et al., "Dystrophic phenotype induced in vitro by antibody blockade of muscle α-dystroglycan-laminin interaction," *Journal of Cell Science* 112:209-216, 1999.
Collins et al., "Duchenne's muscular dystrophy: animal models used to investigate pathogenesis and develop therapeutic strategies," *International Journal of Experimental Pathology* 84:165-172, 2003.
De Angelis et al., "Chimeric snRNA molecules carrying antisense sequences against the splice junctions of exon 51 of the dystrophin pre-mRNA induce exon skipping and restoration of a dystrophin synthesis in Δ48-50 DMD cells," *Proc. Natl. Acad. Sci. USA* 99(14):9456-9461, Jul. 9, 2002.

(Continued)

*Primary Examiner* — Kimberly Chong
(74) *Attorney, Agent, or Firm* — Seed IP Law Group PLLC

(57) ABSTRACT

An antisense molecule capable of binding to a selected target site to induce exon skipping in the dystrophin gene, as set forth in SEQ ID NO: 1 to 202.

24 Claims, 22 Drawing Sheets

OTHER PUBLICATIONS

DelloRusso et al., "Functional correction of adult *mdx* mouse muscle using gutted adenoviral vectors expressing full-length dystrophin," *Proc. Natl. Acad. Sci. USA* 99(20):12979-12984, Oct. 2002.

Dirksen et al., "Mapping the SF2/ASF Binding Sites in the Bovine Growth Hormone Exonic Splicing Enhancer," *The Journal of Biological Chemistry* 275(37):29170-29177, 2000.

Dunckley et al., "Modification of splicing in the dystrophin gene in cultured *Mdx* muscle cells by antisense oligoribonucleotides," *Human Molecular Genetics* 5(1):1083-1090, 1995.

Dunckley et al., "Modulation of Splicing in the *DMD* Gene by Antisense Oligoribonucleotides," *Nucleosides & Nucleotides* 16(7-9):1665-1668, 1997.

Errington et al., "Target selection for antisense oligonucleotide induced exon skipping in the dystrophin gene," *The Journal of Gene Medicine* 5:518-527, 2003.

Friedmann, "Progress Toward Human Gene Therapy," *Science* 244:1275-1281, Jun. 16, 1989.

Gebski et al., "Morpholino antisense oligonucleotide induced dystrophin exon 23 skipping in *mdx* mouse muscle," *Human Molecular Genetics* 12(15):1801-1811, 2003.

Giles et al., "Antisense Morpholino Oligonucleotide Analog Induces Missplicing of C-*myc* mRNA," *Antisense & Nucleic Acid Drug Development* 9:213-220, 1999.

Gennaro, Alfonso R., (ed.), *Remington's Pharmaceutical Studies*, 18$^{th}$ Edition, Mack Publishing, Co., Eastern, PA. 1990.

Harel-Bellan et al., "Specific Inhibition of c-*myc* Protein Biosynthesis Using an Antisense Synthetic Deoxy-Oligonucleotide in Human T Lymphocytes," *The Journal of Immunology* 140(7):2431-2435, Apr. 1, 1988.

Hussey et al., "Analysis of five Duchenne muscular dystrophy exons and gender determination using conventional duplex polymerase chain reaction on single cells," *Molecular Human Reproduction* 5(11):1089-1094, 1999.

International Search Report for International Application No. PCT/US01/14410, mailed Mar. 6, 2002, 5 pages.

Karras et al., "Deletion of Individual Exons and Induction of Soluble Murine Interleukin-5 Receptor-α Chain Expression through Antisense Oligonucleotide-Mediated Redirection of Pre-mRNA Splicing," *Molecular Pharmacology* 58:380-387, 2000.

Liu et al., "Identification of functional exonic splicing enhancer motifs recognized by individual SR proteins," *Genes & Development* 12:1998-2012, 1998.

Lu et al., "Massive Idiosyncratic Exon Skipping Corrects the Nonsense Mutation in Dystrophic Mouse Muscle and Produces Functional Revertant Fibers by Clonal Expansion," *The Journal of Cell Biology* 148(5):985-995, Mar. 6, 2000.

Lu et al., "Functional amounts of dystrophin produced by skipping the mutated exon in the *mdx* dystrophic mouse," *Nature Medicine* 9(8):1009-1014, Aug. 2003.

Mann et al., "Antisense-induced exon skipping and synthesis of dystrophin in the *mdx* mouse," *Proc. Natl. Acad. Sci. USA* 98(1):42-47, Jan. 2, 2001.

Mann et al., "Improved antisense oligonucleotide induced exon skipping in the *mdx* mouse model of muscular dystrophy," *The Journal of Gene Medicine* 4:644-654, 2002.

Matsuo et al., "Exon Skipping during Splicing of Dystrophin mRNA Precursor due to an intraexon Deletion in the Dystrophin Gene of Duchenne Muscular Dystrophy Kobe," *J. Clin. Invest.* 87:2127-2131, Jun. 1991.

Matsuo, "Duchenne/Becker muscular dystrophy: from molecular diagnosis to gene therapy," *Brain & Development* 18:167-172, 1996.

Matsuo, "Duchenne and Becker Muscular Dystrophy: From Gene Diagnosis to Molecular Therapy," *IUBMB Life* 53:147-152, 2002.

Monaco et al., "An Explanation for the Phenotypic Differences between Patients Bearing Partial Deletions of the DMD Locus," *Genomics* 2:90-95, 1988.

Patentee's Response to European Patent Application No. 05076770. 6, dated Jul. 28, 2006, 4 pages.

Pramono et al., "Induction of Exon Skipping of the Dystrophin Transcript in Lymphoblastoid Cells by Transfecting an Antisense Oligodeoxynucleotide Complementary to an Exon Recognition Sequence," *Biochemical and Biophysical Research Communications* 226:445-449, 1996.

Roberts et al., "Exon Structure of the Human Dystrophin Gene," *Genomics* 16:536-538, 1993.

Shapiro et al., "RNA splice junctions of different classes of eukaryotes: sequence statistics and functional implications in gene expression," *Nucleic Acids Research* 15(17):7155-7174, 1987.

Sherratt et al., "Exon Skipping and Translation in Patients with Frameshift Deletions in the Dystrophin Gene," *Am. J. Hum. Genet.* 53:1007-1015, 1993.

Shiga et al., "Disruption of the Splicing Enhancer Sequence within Exon 27 of the Dystrophin Gene by a Nonsense Mutation Induces Partial Skipping of the Exon and Is Responsible for Becker Muscular Dystrophy," *J. Clin. Invest.* 100(9):2204-2210, Nov. 1997.

Sierakowska et al., "Repair of thalassemic human β-globin mRNA in mammalian cells by antisense oligonucleotides," *Proc. Natl. Acad. Sci. USA* 93:12840-12844, Nov. 1996.

Summerton et al., "Morpholino Antisense Oligomers: Design, Preparation, and Properties," *Antisense & Nucleic Acid Drug Development* 7:187-195, 1997.

Takeshima et al., "Modulation of In Vitro Splicing of the Upstream Intron by Modifying an Intra-Exon Sequence Which Is Deleted from the Dystrophin Gene in Dystrophin Kobe," *J. Clin. Invest.* 95:515-520, Feb. 1995.

Tanaka et al., "Polypurine Sequences within a Downstream Exon Function as a Splicing Enhancer," *Molecular and Cellular Biology* 14(2):1347-1354, Feb. 1994.

Thanh et al., "Characterization of Revertant Muscle Fibers in Duchenne Muscular Dystrophy, Using Exon-Specific Monoclonal Antibodies against Dystrophin," *Am. J. Hum. Genet.* 56:725-731, 1995.

van Deutekom et al., "Advances in Duchenne Muscular Dystrophy Gene Therapy," *Nature Reviews Genetics* 4:774-783, Oct. 2003.

van Deutekom et al., "Antisense-induced exon skipping restores dystrophin expression in DMD patient derived muscle cells," *Human Molecular Genetics* 10(15):1547-1554, 2001.

Volloch et al., "Inhibition of Pre-mRNA Splicing by Antisense RNA In Vitro: Effect of RNA Containing Sequences Complementary to Exons," *Biochemical and Biophysical Research Communications* 179(3):1593-1599, Sep. 30, 1991.

Watakabe et al., "The role of exon sequences in splice site selection," *Genes & Development* 7:407-418, 1993.

Wilton et al., "Specific removal of the nonsense mutation from the *mdx* dystrophin mRNA using antisense oligonucleotides," *Neuromuscular Disorders* 9:330-338, 1999.

Asvadi et al., "Expression and functional analysis of recombinant scFv and diabody fragments with specificity for human RhD," *Journal of Molecular Recognition* 15:321-330, 2002.

Rosso et al., "An *Arabidopsis thaliana* T-DNA mutagenized population (GABI-Kat) for flanking sequence tag-based reverse genetics," *Plant Molecular Biology* 53:247-259, 2003.

FIGURE 1.

```
         Acceptor            ESE                                    Donor
bp  ucaugcacugagugacccucuuucucgcagGCGCUAGCUGGAGCA/////CCGUGCAGACUGACGgucucau
```

6A(+69+91)

1

ANTISENSE OLIGONUCLEOTIDES FOR INDUCING EXON SKIPPING AND METHODS OF USE THEREOF

CROSS-REFERENCE TO RELATED APPLICATIONS

This application is a continuation of U.S. patent application Ser. No. 11/570,691, filed Jan. 15, 2008, now issued as U.S. Pat. No. 7,807,816, which application is a 35 U.S.C. §371 National Phase Application of PCT/AU2005/000943, filed Jun. 28, 2005, which claims priority to Australian Patent Application No. 2004903474, filed Jun. 28, 2004; which applications are each incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_411C3_SEQUENCE_LISTING.txt. The text file is 49 KB, was created on Nov. 3, 2009, and is being submitted electronically via EFS-Web.

FIELD OF THE INVENTION

The present invention relates to novel antisense compounds and compositions suitable for facilitating exon skipping. It also provides methods for inducing exon skipping using the novel antisense compounds as well as therapeutic compositions adapted for use in the methods of the invention.

BACKGROUND ART

Significant effort is currently being expended researching methods for suppressing or compensating for disease-causing mutations in genes. Antisense technologies are being developed using a range of chemistries to affect gene expression at a variety of different levels (transcription, splicing, stability, translation). Much of that research has focused on the use of antisense compounds to correct or compensate for abnormal or disease-associated genes in a myriad of different conditions.

Antisense molecules are able to inhibit gene expression with exquisite specificity and because of this many research efforts concerning oligonucleotides as modulators of gene expression have focused on inhibiting the expression of targeted genes such as oncogenes or viral genes. The antisense oligonucleotides are directed either against RNA (sense strand) or against DNA where they form triplex structures inhibiting transcription by RNA polymerase II. To achieve a desired effect in specific gene down-regulation, the oligonucleotides must either promote the decay of the targeted mRNA or block translation of that mRNA, thereby effectively preventing de novo synthesis of the undesirable target protein.

Such techniques are not useful where the object is to up-regulate production of the native protein or compensate for mutations which induce premature termination of translation such as nonsense or frame-shifting mutations. Furthermore, in cases where a normally functional protein is prematurely terminated because of mutations therein, a means for restoring some functional protein production through antisense technology has been shown to be possible through intervention during the splicing processes (Sierakowska H, et al., (1996) *Proc Natl Acad Sci USA* 93,12840-12844; Wilton S D, et al., (1999) *Neuromusc Disorders* 9, 330-338; van Deutekom J C et al., (2001) *Human Mol Genet.* 10, 1547-1554). In these cases, the defective gene transcript should not be subjected to targeted degradation so the antisense oligonucleotide chemistry should not promote target mRNA decay.

In a variety of genetic diseases, the effects of mutations on the eventual expression of a gene can be modulated through a process of targeted exon skipping during the splicing process. The splicing process is directed by complex multi-particle machinery that brings adjacent exon-intron junctions in pre-mRNA into close proximity and performs cleavage of phosphodiester bonds at the ends of the introns with their subsequent reformation between exons that are to be spliced together. This complex and highly precise process is mediated by sequence motifs in the pre-mRNA that are relatively short semi-conserved RNA segments to which bind the various nuclear splicing factors that are then involved in the splicing reactions. By changing the way the splicing machinery reads or recognises the motifs involved in pre-mRNA processing, it is possible to create differentially spliced mRNA molecules. It has now been recognised that the majority of human genes are alternatively spliced during normal gene expression, although the mechanisms invoked have not been identified. Using antisense oligonucleotides, it has been shown that errors and deficiencies in a coded mRNA could be bypassed or removed from the mature gene transcripts.

In nature, the extent of genetic deletion or exon skipping in the splicing process is not fully understood, although many instances have been documented to occur, generally at very low levels (Sherrat T G, et al., (1993) *Am J Hum Genet* 53, 1007-1015). However, it is recognised that if exons associated with disease-causing mutations can be specifically deleted from some genes, a shortened protein product can sometimes be produced that has similar biological properties of the native protein or has sufficient biological activity to ameliorate the disease caused by mutations associated with the target exon (Lu Q L, et al., (2003) *Nature Medicine* 9, 1009-1014; Aartsma-Rus A et al., (2004) *Am J Hum Genet* 74: 83-92).

This process of targeted exon skipping is likely to be particularly useful in long genes where there are many exons and introns, where there is redundancy in the genetic constitution of the exons or where a protein is able to function without one or more particular exons (e.g. with the dystrophin gene, which consists of 79 exons; or possibly some collagen genes which encode for repeated blocks of sequence or the huge nebulin or titin genes which are comprised of ~80 and over 370 exons, respectively).

Efforts to redirect gene processing for the treatment of genetic diseases associated with truncations caused by mutations in various genes have focused on the use of antisense oligonucleotides that either: (1) fully or partially overlap with the elements involved in the splicing process; or (2) bind to the pre-mRNA at a position sufficiently close to the element to disrupt the binding and function of the splicing factors that would normally mediate a particular splicing reaction which occurs at that element (e.g., binds to the pre-mRNA at a position within 3, 6, or 9 nucleotides of the element to be blocked).

For example, modulation of mutant dystrophin pre-mRNA splicing with antisense oligoribonucleotides has been reported both in vitro and in vivo. In one type of dystrophin mutation reported in Japan, a 52-base pair deletion mutation causes exon 19 to be removed with the flanking introns during the splicing process (Matsuo et al., (1991) *J Clin Invest.*

87:2127-2131). An in vitro minigene splicing system has been used to show that a 31-mer 2'-O-methyl oligoribonucleotide complementary to the 5' half of the deleted sequence in dystrophin Kobe exon 19 inhibited splicing of wild-type pre-mRNA (Takeshima et al. (1995), *J. Clin. Invest.*, 95, 515-520). The same oligonucleotide was used to induce exon skipping from the native dystrophin gene transcript in human cultured lymphoblastoid cells.

Dunckley et al., (1997) *Nucleosides & Nucleotides*, 16, 1665-1668 described in vitro constructs for analysis of splicing around exon 23 of mutated dystrophin in the mdx mouse mutant, a model for muscular dystrophy. Plans to analyse these constructs in vitro using 2' modified oligonucleotides targeted to splice sites within and adjacent to mouse dystrophin exon 23 were discussed, though no target sites or sequences were given.

2'-O-methyl oligoribonucleotides were subsequently reported to correct dystrophin deficiency in myoblasts from the mdx mouse from this group. An antisense oligonucleotide targeted to the 3' splice site of murine dystrophin intron 22 was reported to cause skipping of the mutant exon as well as several flanking exons and created a novel in-frame dystrophin transcript with a novel internal deletion. This mutated dystrophin was expressed in 1-2% of antisense treated mdx myotubes. Use of other oligonucleotide modifications such as 2'-O-methoxyethyl phosphodiesters are described (Dunckley et al. (1998) *Human Mol. Genetics*, 5, 1083-90).

Thus, antisense molecules may provide a tool in the treatment of genetic disorders such as Duchenne Muscular Dystrophy (DMD). However, attempts to induce exon skipping using antisense molecules have had mixed success. Studies on dystrophin exon 19, where successful skipping of that exon from the dystrophin pre-mRNA was achieved using a variety of antisense molecules directed at the flanking splice sites or motifs within the exon involved in exon definition as described by Errington et al. (2003) *J Gen Med* 5, 518-527".

In contrast to the apparent ease of exon 19 skipping, the first report of exon 23 skipping in the mdx mouse by Dunckley et al., (1998) is now considered to be reporting only a naturally occurring revertant transcript or artefact rather than any true antisense activity. In addition to not consistently generating transcripts missing exon 23, Dunckley et al., (1998) did not show any time course of induced exon skipping, or even titration of antisense oligonucleotides, to demonstrate dose dependent effects where the levels of exon skipping corresponded with increasing or decreasing amounts of antisense oligonucleotide. Furthermore, this work could not be replicated by other researchers.

The first example of specific and reproducible exon skipping in the mdx mouse model was reported by Wilton et al., (1999) *Neuromuscular Disorders* 9, 330-338. By directing an antisense molecule to the donor splice site, consistent and efficient exon 23 skipping was induced in the dystrophin mRNA within 6 hours of treatment of the cultured cells. Wilton et al., (1999), also describe targeting the acceptor region of the mouse dystrophin pre-mRNA with longer antisense oligonucleotides and being unable to repeat the published results of Dunckley et al., (1998). No exon skipping, either 23 alone or multiple removal of several flanking exons, could be reproducibly detected using a selection of antisense oligonucleotides directed at the acceptor splice site of intron 22.

While the first antisense oligonucleotide directed at the intron 23 donor splice site induced consistent exon skipping in primary cultured myoblasts, this compound was found to be much less efficient in immortalized cell cultures expressing higher levels of dystrophin. However, with refined targeting and antisense oligonucleotide design, the efficiency of specific exon removal was increased by almost an order of magnitude (see Mann C J et al., (2002) *J Gen Med* 4, 644-654).

Thus, there remains a need to provide antisense oligonucleotides capable of binding to and modifying the splicing of a target nucleotide sequence. Simply directing the antisense oligonucleotides to motifs presumed to be crucial for splicing is no guarantee of the efficacy of that compound in a therapeutic setting.

SUMMARY OF THE INVENTION

The present invention provides antisense molecule compounds and compositions suitable for binding to RNA motifs involved in the splicing of pre-mRNA that are able to induce specific and efficient exon skipping and a method for their use thereof.

The choice of target selection plays a crucial role in the efficiency of exon skipping and hence its subsequent application of a potential therapy. Simply designing antisense molecules to target regions of pre-mRNA presumed to be involved in splicing is no guarantee of inducing efficient and specific exon skipping. The most obvious or readily defined targets for splicing intervention are the donor and acceptor splice sites although there are less defined or conserved motifs including exonic splicing enhancers, silencing elements and branch points.

The acceptor and donor splice sites have consensus sequences of about 16 and 8 bases respectively (see FIG. 1 for schematic representation of motifs and domains involved in exon recognition, intron removal and the splicing process).

According to a first aspect, the invention provides antisense molecules capable of binding to a selected target to induce exon skipping.

For example, to induce exon skipping in exons 3 to 8, 10 to 16, 19 to 40, 42 to 44, 46, 47, and 50 to 53 in the Dystrophin gene transcript the antisense molecules are preferably selected from the group listed in Table 1A.

In a further example, it is possible to combine two or more antisense oligonucleotides of the present invention together to induce multiple exon skipping in exons 19-20, and 53. This is a similar concept to targeting of a single exon. A combination or "cocktail" of antisense oligonucleotides are directed at adjacent exons to induce efficient exon skipping.

In another example, to induce exon skipping in exons 19-20, 31, 34 and 53 it is possible to improve exon skipping of a single exon by joining together two or more antisense oligonucleotide molecules. This concept is termed by the inventor as a "weasel", an example of a cunningly designed antisense oligonucleotide. A similar concept has been described in Aartsma-Rus A et al., (2004) *Am J Hum Genet* 74: 83-92).

According to a second aspect, the present invention provides antisense molecules selected and or adapted to aid in the prophylactic or therapeutic treatment of a genetic disorder comprising at least an antisense molecule in a form suitable for delivery to a patient.

According to a third aspect, the invention provides a method for treating a patient suffering from a genetic disease wherein there is a mutation in a gene encoding a particular protein and the affect of the mutation can be abrogated by exon skipping, comprising the steps of: (a) selecting an antisense molecule in accordance with the methods described herein; and (b) administering the molecule to a patient in need of such treatment.

The invention also addresses the use of purified and isolated antisense oligonucleotides of the invention, for the manufacture of a medicament for treatment of a genetic disease.

The invention further provides a method of treating a condition characterised by Duchenne muscular dystrophy, which method comprises administering to a patient in need of treatment an effective amount of an appropriately designed antisense oligonucleotide of the invention, relevant to the particular genetic lesion in that patient. Further, the invention provides a method for prophylactically treating a patient to prevent or at least minimise Duchene muscular dystrophy, comprising the step of: administering to the patient an effective amount of an antisense oligonucleotide or a pharmaceutical composition comprising one or more of these biological molecules.

The invention also provides kits for treating a genetic disease, which kits comprise at least a antisense oligonucleotide of the present invention, packaged in a suitable container and instructions for its use.

Other aspects and advantages of the invention will become apparent to those skilled in the art from a review of the ensuing description, which proceeds with reference to the following figures.

BRIEF DESCRIPTION OF THE DRAWINGS

FIG. 1 Schematic representation of motifs and domains involved in exon recognition, intron removal and the splicing process (SEQ ID NOS: 213 and 214).

Brief Description of the Sequence Listings

TABLE 1A

Figure 2:
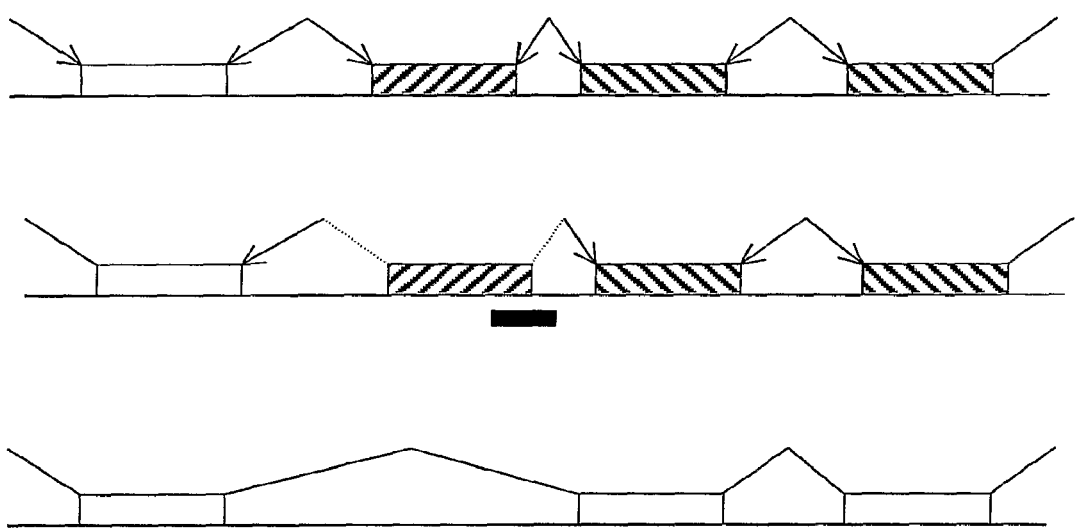
FIG. 2 Diagrammatic representation of the concept of antisense oligonucleotide induced exon skipping to by-pass disease-causing mutations (not drawn to scale). The hatched box represents an exon carrying a mutation that prevents the translation of the rest of the mRNA into a protein. The solid black bar represents an antisense oligonucleotide that prevents inclusion of that exon in the mature mRNA.

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptidenucleic acids or morpholinos, these U bases may be shown as "T".

| SEQ ID | SEQUENCE | NUCLEOTIDE SEQUENCE (5'-3') |
|---|---|---|
| 1 | H8A(-06+18) | GAU AGG UGG UAU CAA CAU CUG UAA |
| 2 | H8A (-03+18) | GAU AGG UGG UAU CAA CAU CUG |
| 3 | H8A(-07+18) | GAU AGG UGG UAU CAA CAU CUG UAA G |
| 4 | H8A(-06+14) | GGU GGU AUC AAC AUC UGU AA |
| 5 | H8A(-10+10) | GUA UCA ACA UCU GUA AGC AC |
| 6 | H7A(+45+67) | UGC AUG UUC CAG UCG UUG UGU GG |
| 7 | H7A(+02+26) | CAC UAU UCC AGU CAA AUA GGU CUG G |
| 8 | H7D(+15-10) | AUU UAC CAA CCU UCA GGA UCG AGU A |
| 9 | H7A(-18+03) | GGC CUA AAA CAC AUA CAC AUA |
| 10 | C6A(-10+10) | CAU UUU UGA CCU ACA UGU GG |
| 11 | C6A(-14+06) | UUU GAC CUA CAU GUG GAA AG |
| 12 | C6A(-14+12) | UAC AUU UUU GAC CUA CAU GUG GAA AG |
| 13 | C6A(-13+09) | AUU UUU GAC CUA CAU GGG AAA G |
| 14 | CH6A(+69+91) | UAC GAG UUG AUU GUC GGA CCC AG |
| 15 | C6D(+12-13) | GUG GUC UCC UUA CCU AUG ACU GUG G |
| 16 | C6D(+06-11) | GGU CUC CUU ACC UAU GA |
| 17 | H6D(+04-21) | UGU CUC AGU AAU CUU CUU ACC UAU |
| 18 | H6D(+18-04) | UCU UAC CUA UGA CUA UGG AUG AGA |
| 19 | H4A(+13+32) | GCA UGA ACU CUU GUG GAU CC |
| 20 | H4D(+04-16) | CCA GGG UAC UAC UUA CAU UA |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptidenucleic acids or morpholinos, these U bases may be shown as "T".

| SEQ ID | SEQUENCE | NUCLEOTIDE SEQUENCE (5'-3') |
|---|---|---|
| 21 | H4D(-24-44) | AUC GUG UGU CAC AGC AUC CAG |
| 22 | H4A(+11+40) | UGU UCA GGG CAU GAA CUC UUG UGG AUC CUU |
| 23 | H3A(+30+60) | UAG GAG GCG CCU CCC AUC CUG UAG UCA CUG |
| 24 | H3A(+35+65) | AGG UCU AGG AGG CGC CUC CCA UCC UGU AGG U |
| 25 | H3A(+30+54) | GCG CCU CCC AUC CUG UAG GUC ACU G |
| 26 | H3D(+46-21) | CUU CGA GGA GGU CUA GGA GGC GCC UC |
| 27 | H3A(+30+50) | CUC CCA UCC UGU AGG UCA CUG |
| 28 | H3D(+19-03) | UAC CAG UUU UUG CCC UGU CAG G |
| 29 | H3A(-06+20) | UCA AUA UGC UGC UUC CCA AAC UGA AA |
| 30 | H3A(+37+61) | CUA GGA GGC GCC UCC CAU CCU GUA G |
| 31 | H5A(+20+50) | UUA UGA UUU CCA UCU ACG AUG UCA GUA CUU C |
| 32 | H5D(+25-05) | CUU ACC UGC CAG UGG AGG AUU AUA UUC CAA A |
| 33 | H5D(+10-15) | CAU CAG GAU UCU UAC CUG CCA GUG G |
| 34 | H5A(+10+34) | CGA UGU CAG UAC UUC CAA UAU UCA C |
| 35 | H5D(-04-21) | ACC AUU CAU CAG GAU UCU |
| 36 | H5D(+16-02) | ACC UGC CAG UGG AGG AUU |
| 37 | H5A(-07+20) | CCA AUA UUC ACU AAA UCA ACC UGU UAA |
| 38 | H5D(+18-12) | CAG GAU UCU UAC CUG CCA GUG GAG GAU UAU |
| 39 | H5A(+05+35) | ACG AUG UCA GUA CUU CCA AUA UUC ACU AAA U |
| 40 | H5A(+15+45) | AUU CCA UCU ACG AUG UCA AGU ACU UCC AAU A |
| 41 | H10A(-05+16) | CAG GAG CUU CCA AAU GCU GCA |
| 42 | H10A(-05+24) | CUU GUC UUC AGG AGC UUC CAA AUG CUG CA |
| 43 | H10A(+98+119) | UCC UCA GCA GAA AGA AGC CAC G |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptidenucleic acids or morpholinos, these U bases may be shown as "T".

| SEQ ID | SEQUENCE | NUCLEOTIDE SEQUENCE (5'-3') |
|---|---|---|
| 44 | H10A(+130+149) | UUA GAA AUC UCU CCU UGU GC |
| 45 | H10A(-33-14) | UAA AUU GGG UGU UAC ACA AU |
| 46 | H11D(+26+49) | CCC UGA GGC AUU CCC AUC UUG AAU |
| 47 | H11D(+11-09) | AGG ACU UAC UUG CUU UGU UU |
| 48 | H11A(+118+140) | CUU GAA UUU AGG AGA UUC AUC UG |
| 49 | H11A(+75+97) | CAU CUU CUG AUA AUU UUC CUG UU |
| 50 | H12A(+52+75) | UCU UCU GUU UUU GUU AGC CAG UCA |
| 51 | H12A(-10+10) | UCU AUG UAA ACU GAA AAU UU |
| 52 | H12A(+11+30) | UUC UGG AGA UCC AUU AAA AC |
| 53 | H13A(+77+100) | CAG CAG UUG CGU GAU CUC CAC UAG |
| 54 | H13A(+55+75) | UUC AUC AAC UAC CAC CAC CAU |
| 55 | H13D(+06-19) | CUA AGC AAA AUA AUC UGA CCU UAA G |
| 56 | H14A(+37+64) | CUU GUA AAA GAA CCC AGC GGU CUU CUG U |
| 57 | H14A(+14+35) | CAU CUA CAG AUG UUU GCC CAU C |
| 58 | H14A(+51+73) | GAA GGA UGU CUU GUA AAA GAA CC |
| 59 | H14D(-02+18) | ACC UGU UCU UCA GUA AGA CG |
| 60 | H14D(+14-10) | CAU GAC ACA CCU GUU CUU CAG UAA |
| 61 | H14A(+61+80) | CAU UUG AGA AGG AUG UCU UG |
| 62 | H14A(-12+12) | AUC UCC AAU ACU CUG GAG AAG AGA |
| 63 | H15A(-12+19) | GCC AUG CAC UAA AAA GGC ACU GCA AGA CAU U |
| 64 | H15A(+48+71) | UCU UUA AAG CCA GUU GUG UGA AUC |
| 65 | H15A(+08+28) | UUU CUG AAA GCC AUG CAC UAA |
| 66 | H15D(+17-08) | GUA CAU ACG GCC AGU UUU UGA AGA C |
| 67 | H16A(-12+19) | CUA GAU CCG CUU UUA AAA CCU GUU AAA ACA A |
| 68 | H16A(-06+25) | UCU UUU CUA GAU CCG CUU UUA AAA CCU GUU A |
| 69 | H16A(-06+19) | CUA GAU CCG CUU UUA AAA CCU GUU A |
| 70 | H16A(+87+109) | CCG UCU UCU GGG UCA CUG ACU UA |
| 71 | H16A(-07+19) | CUA GAU CCG CUU UUA AAA CCU GUU AA |
| 72 | H16A(-07+13) | CCG CUU UUA AAA CCU GUU AA |
| 73 | H16A(+12+37) | UGG AUU GCU UUU UCU UUU CUA GAU CC |
| 74 | H16A(+92+116) | CAU GCU UCC GUC UUC UGG GUC ACU G |
| 75 | H16A(+45+67) | G AUC UUG UUU GAG UGA AUA CAG U |
| 76 | H16A(+105+126) | GUU AUC CAG CCA UGC UUC CGU C |
| 77 | H16D(+05-20) | UGA UAA UUG GUA UCA CUA ACC UGU G |
| 78 | H16D(+12-11) | GUA UCA CUA ACC UGU GCU GUA C |
| 79 | H19A(+35+53) | CAG CAG UAG UUG UCA UCU GC |
| 80 | H19A(+35+65) | GCC UGA GCU GAU CUG CUG GCA UCU UGC AGU U |
| 81 | H20A(+44+71) | CUG GCA GAA UUC GAU CCA CCG GCU GUU C |
| 82 | H20A(+149+170) | CAG CAG UAG UUG UCA UCU GCU C |
| 83 | H20A(+185+203) | UGA UGG GGU GGU GGG UUG G |
| 84 | H20A(-08+17) | AUC UGC AUU AAC ACC CUC UAG AAA G |
| 85 | H20A(+30+53) | CCG GCU GUU CAG UUG UUC UGA GGC |
| 86 | H20A(-11+17) | AUC UGC AUU AAC ACC CUC UAG AAA GAA A |
| 87 | H20D(+08-20) | GAA GGA GAA GAG AUU CUU ACC UUA CAA A |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptidenucleic acids or morpholinos, these U bases may be shown as "T".

| SEQ ID | SEQUENCE | NUCLEOTIDE SEQUENCE (5'-3') |
|---|---|---|
| 88 | H20A(+44+63) | AUU CGA UCC ACC GGC UGU UC |
| 89 | H20A(+149+168) | CUG CUG GCA UCU UGC AGU U |
| 90 | H21A(−06+16) | GCC GGU UGA CUU CAU CCU GUG C |
| 91 | H21A(+85+106) | CUG CAU CCA GGA ACA UGG GUC C |
| 92 | H21A(+85+108) | GUC UGC AUC CAG GAA CAU GGG UC |
| 93 | H21A(+08+31) | GUU GAA GAU CUG AUA GCC GGU UGA |
| 94 | H21D(+18−07) | UAC UUA CUG UCU GUA GCU CUU UCU |
| 95 | H22A(+22+45) | CAC UCA UGG UCU CCU GAU AGC GCA |
| 96 | H22A(+125+106) | CUG CAA UUC CCC GAG UCU CUG C |
| 97 | H22A(+47+69) | ACU GCU GGA CCC AUG UCC UGA UG |
| 98 | H22A(+80+101) | CUA AGU UGA GGU AUG GAG AGU |
| 99 | H22D(+13−11) | UAU UCA CAG ACC UGC AAU UCC CC |
| 100 | H23A(+34+59) | ACA GUG GUG CUG AGA UAG UAU AGG CC |
| 101 | H23A(+18+39) | UAG GCC ACU UUG UUG CUC UUG C |
| 102 | H23A(+72+90) | UUC AGA GGG CGC UUU CUU C |
| 103 | H24A(+48+70) | GGG CAG GCC AUU CCU CCU UCA GA |
| 104 | H24A(−02+22) | UCU UCA GGG UUU GUA UGU GAU UCU |
| 105 | H25A(+9+36) | CTG GGC UGA AUU GUC UGA AUA UCA CUG |
| 106 | H25A(+131+156) | CUG UUG GCA CAU GUG AUC CCA CUG AG |
| 107 | H25D(+16−08) | GUC UAU ACC UGU UGG CAC AUG UGA |
| 108 | H26A(+132+156) | UGC UUU CUG UAA UUC AUC UGG AGU U |
| 109 | H26A(−07+19) | CCU CCU UUC UGG CAU AGA CCU UCC AC |
| 110 | H26A(+68+92) | UGU GUC AUC CAU UCG UGC AUC UCU G |
| 111 | H27A(+82+106) | UUA AGG CCU CUU GUG CUA CAG GUG G |
| 112 | H27A(−4+19) | GGG CCU CUU CUU UAG CUC UCU GA |
| 113 | H27D(+19−03) | GAC UUC CAA AGU CUU GCA UUU C |
| 114 | H28A(−05+19) | GCC AAC AUG CCC AAA CUU CCU AAG |
| 115 | H28A(+99+124) | CAG AGA UUU CCU CAG CUC CGC CAG GA |
| 116 | H28D(+16−05) | CUU ACA UCU AGC ACC UCA GAG |
| 117 | H29A(+57+81) | UCC GCC AUC UGU UAG GGU CUG UGC C |
| 118 | H29A(+18+42) | AUU UGG GUU AUC CUC UGA AUG UCG C |
| 119 | H29D(+17−05) | CAU ACC UCU UCA UGU AGU UCU C |
| 120 | H30A(+122+147) | CAU UUG AGC UGC GUC CAC CUU GUC UG |
| 121 | H30A(+25+50) | UCC UGG GCA GAC UGG AUG CUC UGU UC |
| 122 | H30D(+19−04) | UUG CCU GGG CUU CCU GAG GCA UU |
| 123 | H31D(+06−18) | UUC UGA AAU AAC AUA UAC CUG UGC |
| 124 | H31D(+03−22) | UAG UUU CUG AAA UAA CAU AUA CCU G |
| 125 | H31A(+05+25) | GAC UUG UCA AAU CAG AUU GGA |
| 126 | H31D(+04−20) | GUU UCU GAA AUA ACA UAU ACC UGU |
| 127 | H32D(+04−16) | CAC CAG AAA UAC AUA CCA CA |
| 128 | H32A(+151+170) | CAA UGA UUU AGC UGU GAC UG |
| 129 | H32A(+10+32) | CGA AAC UUC AUG GAG ACA UCU UG |
| 130 | H32A(+49+73) | CUU GUA GAC GCU GCU CAA AAU UGG C |
| 131 | H33D(+09−11) | CAU GCA CAC ACC UUU GCU CC |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptidenucleic acids or morpholinos, these U bases may be shown as "T".

| SEQ ID | SEQUENCE | NUCLEOTIDE SEQUENCE (5'-3') |
|---|---|---|
| 132 | H33A(+53+76) | UCU GUA CAA UCU GAC GUC CAG UCU |
| 133 | H33A(+30+56) | GUC UUU AUC ACC AUU UCC ACU UCA GAC |
| 134 | H33A(+64+88) | CCG UCU GCU UUU UCU GUA CAA UCU G |
| 135 | H34A(+83+104) | UCC AUA UCU GUA GCU GCC AGC C |
| 136 | H34A(+143+165) | CCA GGC AAC UUC AGA AUC CAA AU |
| 137 | H34A(-20+10) | UUU CUG UUA CCU GAA AAG AAU UAU AAU GAA |
| 138 | H34A(+46+70) | CAU UCA UUU CCU UUC GCA UCU UAC G |
| 139 | H34A(+95+120) | UGA UCU CUU UGU CAA UUC CAU AUC UG |
| 140 | H34D(+10-20) | UUC AGU GAU AUA GGU UUU ACC UUU CCC CAG |
| 141 | H34A(+72+96) | CUG UAG CUG CCA GCC AUU CUG UCA AG |
| 142 | H35A(+141+161) | UCU UCU GCU CGG GAG GUG ACA |
| 143 | H35A(+116+135) | CCA GUU ACU AUU CAG AAG AC |
| 144 | H35A(+24+43) | UCU UCA GGU GCA CCU UCU GU |
| 145 | H36A(+26+50) | UGU GAU GUG GUC CAC AUU CUG GUC A |
| 146 | H36A(-02+18) | CCA UGU GUU UCU GGU AUU CC |
| 147 | H37A(+26+50) | CGU GUA GAG UCC ACC UUU GGG CGU A |
| 148 | H37A(+82+105) | UAC UAA UUU CCU GCA GUG GUC ACC |
| 149 | H37A(+134+157) | UUC UGU GUG AAA UGG CUG CAA AUC |
| 150 | H38A(-01+19) | CCU UCA AAG GAA UGG AGG CC |
| 151 | H38A(+59+83) | UGC UGA AUU UCA GCC UCC AGU GGU U |
| 152 | H38A(+88+112) | UGA AGU CUU CCU CUU UCA GAU UCA C |
| 153 | H39A(+62+85) | CUG GCU UUC UCU CAU CUG UGA UUC |
| 154 | H39A(+39+58) | GUU GUA AGU UGU CUC CUC UU |
| 155 | H39A(+102+121) | UUG UCU GUA ACA GCU GCU GU |
| 156 | H39D(+10-10) | GCU CUA AUA CCU UGA GAG CA |
| 157 | H40A(-05+17) | CUU UGA GAC UCU AAA UCC UGU U |
| 158 | H40A(+129+153) | CUU UAU UUU CCU UUC AUC UCU GGG C |
| 159 | H42A(-04+23) | AUC GUU UCU UCA CGG ACA GUG UGC UGG |
| 160 | H42A(+86+109) | GGG CUU GUG AGA CAU GAG UGA UUU |
| 161 | H42D(+19-02) | A CCU UCA GAG GAC UCC UCU UGC |
| 162 | H43D(+10-15) | UAU GUG UUA CCU ACC CUU GUC GGU C |
| 163 | H43A(+101+120) | GGA GAG AGC UUC CUG UAG CU |
| 164 | H43A(+78+100) | UCA CCC UUU CCA CAG GCG UUG CA |
| 165 | H44A(+85+104) | UUU GUG UCU UUC UGA GAA AC |
| 166 | H44D(+10-10) | AAA GAC UUA CCU UAA GAU AC |
| 167 | H44A(-06+14) | AUC UGU CAA AUC GCC UGC AG |
| 168 | H46D(+16-04) | UUA CCU UGA CUU GCU CAA GC |
| 169 | H46A(+90+109) | UCC AGG UUC AAG UGG GAU AC |
| 170 | H47A(+76+100) | GCU CUU CUG GGC UUA UGG GAG CAC U |
| 171 | H47D(+25-02) | ACC UUU AUC CAC UGG AGA UUU GUC UGC |
| 172 | H47A(-9+12) | UUC CAC CAG UAA CUG AAA CAG |
| 173 | H50A(+02+30) | CCA CUC AGA GCU CAG AUC UUC UAA CUU CC |
| 174 | H50A(+07+33) | CUU CCA CUC AGA GCU CAG AUC UUC UAA |
| 175 | H50D(+07-18) | GGG AUC AGU AUU ACU AC AGG CUC C |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptidenucleic acids or morpholinos, these U bases may be shown as "T".

| SEQ ID | SEQUENCE | NUCLEOTIDE SEQUENCE (5'-3') |
|---|---|---|
| 176 | H51A(-01+25) | ACC AGA GUA ACA GUC UGA GUA GGA GC |
| 177 | H51D(+16-07) | CUC AUA CCU UCU GCU UGA UGA UC |
| 178 | H51A(+111+134) | UUC UGU CCA AGC CCG GUU GAA AUC |
| 179 | H51A(+61+90) | ACA UCA AGG AAG AUG GCA UUU CUA GUU UGG |
| 180 | H51A(+66+90) | ACA UCA AGG AAG AUG GCA UUU CUA G |
| 181 | H51A(+66+95) | CUC CAA CAU CAA GGA AGA UGG CAU UUC UAG |
| 182 | H51D(+08-17) | AUC AUU UUU UCU CAU ACC UUC UGC U |
| 183 | H51A/D(+08-17) & (-15+) | AUC AUU UUU UCU CAU ACC UUC UGC UAG GAG CUA AAA |
| 184 | H51A(+175+195) | CAC CCA CCA UCA CCC UCU GUG |
| 185 | H51A(+199+220) | AUC AUC UCG UUG AUA UCC UCA A |
| 186 | H52A(-07+14) | UCC UGC AUU GUU GCC UGU AAG |
| 187 | H52A(+12+41) | UCC AAC UGG GGA CGC CUC UGU UCC AAA UCC |
| 188 | H52A(+17+37) | ACU GGG GAC GCC UCU GUU CCA |
| 189 | H52A(+93+112) | CCG UAA UGA UUG UUC UAG CC |
| 190 | H52D(+05-15) | UGU UAA AAA ACU UAC UUC GA |
| 191 | H53A(+45+69) | CAU UCA ACU GUU GCC UCC GGU UCU G |
| 192 | H53A(+39+62) | CUG UUG CCU CCG GUU CUG AAG GUG |
| 193 | H53A(+39+69) | CAU UCA ACU GUU GCC UCC GGU UCU GAA GGU G |
| 194 | H53D(+14-07) | UAC UAA CCU UGG UUU CUG UGA |
| 195 | H53A(+23+47) | CUG AAG GUG UUC UUG UAC UUC AUC C |
| 196 | H53A(+150+176) | UGU AUA GGG ACC CUC CUU CCA UGA CUC |
| 197 | H53D(+20-05) | CUA ACC UUG GUU UCU GUG AUU UUC U |
| 198 | H53D(+09-18) | GGU AUC UUU GAU ACU AAC CUU GGU UUC |
| 199 | H53A(-12+10) | AUU CUU UCA ACU AGA AUA AAA G |
| 200 | H53A(-07+18) | GAU UCU GAA UUC UUU CAA CUA GAA U |
| 201 | H53A(+07+26) | AUC CCA CUG AUU CUG AAU UC |
| 202 | H53A(+124+145) | UUG GCU CUG GCC UGU CCU AAG A |
| 203 | H46A(+86+115) | CUC UUU UCC AGG UUC AAG UGG GAU ACU AGC |
| 204 | H46A(+107+137) | CAA GCU UUU CUU UUA GUU GCU GCU CUU UUC C |
| 205 | H46A(-10+20) | UAU UCU UUU GUU CUU CUA GCC UGG AGA AAG |
| 206 | H46A(+50+77) | CUG CUU CCU CCA ACC AUA AAA CAA AUU C |
| 207 | H45A(-06+20) | CCA AUG CCA UCC UGG AGU UCC UGU AA |
| 208 | H45A(+91+110) | UCC UGU AGA AUA CUG GCA UC |
| 209 | H45A(+125+151) | UGC AGA CCU CCU GCC ACC GCA GAU UCA |
| 210 | H45D(+16-04) | CUA CCU CUU UUU UCU GUC UG |
| 211 | H45A(+71+90) | UGU UUU UGA GGA UUG CUG AA |

TABLE 1B

Description of a cocktail of 2'-O-methyl phosphorothioate antisense oligonucleotides that have been used to date to study induced exon skipping during the processing of the dystrophin pre-mRNA.

| SEQ ID | SEQUENCE | NUCLEOTIDE SEQUENCE (5'-3') |
|---|---|---|
| 81 | H20A(+44+71) | CUG GCA GAA UUC GAU CCA CCG GCU GUU C |
| 82 | H20A(+149+170) | CAG CAG UAG UUG UCA UCU GCU C |
| 79 | H19A(+35+65) | GCC UGA GCU GAU CUG CUG GCA UCU UGC AGU U |
| 81 | H20A(+44+71) | CUG GCA GAA UUC GAU CCA CCG GCU GUU C |
| 82 | H20A(+149+170) | CAG CAG UAG UUG UCA UCU GCU C |

TABLE 1B-continued

Description of a cocktail of 2'-O-methyl phosphorothioate antisense oligonucleotides that have been used to date to study induced exon skipping during the processing of the dystrophin pre-mRNA.

| SEQ ID | SEQUENCE | NUCLEOTIDE SEQUENCE (5'-3') |
|---|---|---|
| 194 | H53D(+14-07) | UAC UAA CCU UGG UUU CUG UGA |
| 195 | H53A(+23+47) | CTG AAG GUG UUC UUG UAC UUC AUC C |
| 196 | H53A(+150+175) | UGU AUA GGG ACC CUC CUU CCA UGA CUC |

TABLE 1C

Description of a "weasel" of 2'-O-methyl phosphorothioate antisense oligonucleotides that have been used to date to study induced exon skipping during the processing of the dystrophin pre-mRNA.

| SEQ ID | SEQUENCE | NUCELOTIDE SEQUENCE (5'-3') |
|---|---|---|
| 80 | H20A(+44+71)- | CUG GCA GAA UUC GAU CCA CCG GCU GUU C- |
| 82 | H20A(+149+170) | CAG CAG UAG UUG UCA UCU GCU C |
| 81 | H19A(+35+53)- | GCC UGA GCU GAU CUG CUG GCA UCU UGC AGU U |
| 88 | H20A(+44+63)- | -AUU CGA UCU ACC GGC UGU UC- |
| 89 | H20A(+149+168) | AA CUG CUG GCA UCU UGC AGU U |
| 80 | H19A(+35+53)- | GCC UGA GCU GAU CUG CUG GCA UCU UGC AGU U |
| 88 | H20A(+44+63)- | -AUU CGA UCU ACC GGC UGU UC- |
| 80 | H19A(+35+53)- | GCC UGA GCU GAU CUG CUG GCA UCU UGC AGU U |
| 89 | H20A(+149+168) | -AA CUG CUG GCA UCU UGC AGU U |
| 138 | H34A(+46+70)- | CAU UCA UUU CCU UUC GCA UCU UAC G- |
| 139 | H34A(+94+120) | UGA UCU CUU UGU CAA UUC CAU AUC UG |
| 124 | H31D(+03-22)- | UAG UUU CUG AAA UAA CAU AUA CCU G- UU- |
| 144 | H35A(+24+43) | UCU UCA GGU GCA CCU UCU GU |
| 195 | H53A(+23+47)- | CUG AAG GUG UUC UUG UAC UUC AUC C- |
| 196 | H53A(+150+175)-AA- | UGU AUA GGG ACC CUC CUU CCA UGA CUC-AA- |
| 194 | H53D(+14-07) | UAC UAA CCU UGG UUU CUG |
| — | Aimed at exons 19/20/20 | UGA CAG CAG UAG UUG UCA UCU GCU CAA CUG GCA GAA UUC GAU CCA CCG GCU GUU CAA GCC UGA GCU GAU CUG CUC GCA UCU UGC AGU |

DETAILED DESCRIPTION OF THE INVENTION

General

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

Sequence identity numbers (SEQ ID NO:) containing nucleotide and amino acid sequence information included in this specification are collected at the end of the description and have been prepared using the programme PatentIn Version 3.0. Each nucleotide or amino acid sequence is identified in the sequence listing by the numeric indicator <210> followed by the sequence identifier (e.g. <210>1, <210>2, etc.). The length, type of sequence and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (e.g. <400>1, <400>2, etc.).

An antisense molecules nomenclature system was proposed and published to distinguish between the different antisense molecules (see Mann et al., (2002) *J Gen Med* 4, 644-654). This nomenclature became especially relevant when testing several slightly different antisense molecules, all directed at the same target region, as shown below:

H # A/D (x:y).

The first letter designates the species (e.g. H: human, M: murine, C: canine)
"#" designates target dystrophin exon number.
"A/D" indicates acceptor or donor splice site at the beginning and end of the exon, respectively.
(x y) represents the annealing coordinates where "−" or "+" indicate intronic or exonic sequences respectively. As an example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2−18) where the last 2 exonic bases and the first 18 intronic bases correspond to the annealing site of the antisense molecule. Entirely exonic annealing coordinates that would be represented by A(+65+85), that is the site between the $65^{th}$ and $85^{th}$ nucleotide from the start of that exon.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

As used necessarily herein the term "derived" and "derived from" shall be taken to indicate that a specific integer may be obtained from a particular source albeit not directly from that source.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

DESCRIPTION OF THE PREFERRED EMBODIMENT

When antisense molecule(s) are targeted to nucleotide sequences involved in splicing in exons within pre-mRNA sequences, normal splicing of the exon may be inhibited causing the splicing machinery to by-pass the entire mutated exon from the mature mRNA. The concept of antisense oligonucleotide induced exon skipping is shown in FIG. 2. In many genes, deletion of an entire exon would lead to the production of a non-functional protein through the loss of important functional domains or the disruption of the reading frame. In some proteins, however, it is possible to shorten the protein by deleting one or more exons, without disrupting the reading frame, from within the protein without seriously altering the biological activity of the protein. Typically, such proteins have a structural role and or possess functional domains at their ends. The present invention describes antisense molecules capable of binding to specified dystrophin pre-mRNA targets and re-directing processing of that gene.

Antisense Molecules

According to a first aspect of the invention, there is provided antisense molecules capable of binding to a selected target to induce exon skipping. To induce exon skipping in exons of the Dystrophin gene transcript, the antisense molecules are preferably selected from the group of compounds shown in Table 1A. There is also provided a combination or "cocktail" of two or more antisense oligonucleotides capable of binding to a selected target to induce exon skipping. To induce exon skipping in exons of the Dystrophin gene transcript, the antisense molecules in a "cocktail" are preferably selected from the group of compounds shown in Table 1B. Alternatively, exon skipping may be induced by antisense oligonucleotides joined together "weasels" preferably selected from the group of compounds shown in Table 1C.

Designing antisense molecules to completely mask consensus splice sites may not necessarily generate any skipping of the targeted exon. Furthermore, the inventors have discovered that size or length of the antisense oligonucleotide itself is not always a primary factor when designing antisense molecules. With some targets such as exon 19, antisense oligonucleotides as short as 12 bases were able to induce exon skipping, albeit not as efficiently as longer (20-31 bases) oligonucleotides. In some other targets, such as murine dystrophin exon 23, antisense oligonucleotides only 17 residues long were able to induce more efficient skipping than another overlapping compound of 25 nucleotides.

The inventors have also discovered that there does not appear to be any standard motif that can be blocked or masked by antisense molecules to redirect splicing. In some exons, such as mouse dystrophin exon 23, the donor splice site was the most amenable to target to re-direct skipping of that exon. It should be noted that designing and testing a series of exon 23 specific antisense molecules to anneal to overlapping regions of the donor splice site showed considerable variation in the efficacy of induced exon skipping. As reported in Mann et al., (2002) there was a significant variation in the efficiency of bypassing the nonsense mutation depending upon antisense oligonucleotide annealing ("Improved antisense oligonucleotide induced exon skipping in the mdx mouse model of muscular dystrophy". *J Gen Med* 4: 644-654). Targeting the acceptor site of exon 23 or several internal domains was not found to induce any consistent exon 23 skipping.

In other exons targeted for removal, masking the donor splice site did not induce any exon skipping. However, by directing antisense molecules to the acceptor splice site (human exon 8 as discussed below), strong and sustained exon skipping was induced. It should be noted that removal of human exon 8 was tightly linked with the co-removal of exon 9. There is no strong sequence homology between the exon 8 antisense oligonucleotides and corresponding regions of exon 9 so it does not appear to be a matter of cross reaction. Rather the splicing of these two exons is inextricably linked. This is not an isolated instance as the same effect is observed in canine cells where targeting exon 8 for removal also resulted in the skipping of exon 9. Targeting exon 23 for removal in the mouse dystrophin pre-mRNA also results in the frequent removal of exon 22 as well. This effect occurs in a dose dependent manner and also indicates close coordinated processing of 2 adjacent exons.

In other targeted exons, antisense molecules directed at the donor or acceptor splice sites did not induce exon skipping while annealing antisense molecules to intra-exonic regions (i.e. exon splicing enhancers within human dystrophin exon 6) was most efficient at inducing exon skipping. Some exons, both mouse and human exon 19 for example, are readily skipped by targeting antisense molecules to a variety of motifs. That is, targeted exon skipping is induced after using antisense oligonucleotides to mask donor and acceptor splice sites or exon splicing enhancers.

To identify and select antisense oligonucleotides suitable for use in the modulation of exon skipping, a nucleic acid sequence whose function is to be modulated must first be identified. This may be, for example, a gene (or mRNA transcribed form the gene) whose expression is associated with a particular disorder or disease state, or a nucleic acid molecule from an infectious agent. Within the context of the present invention, preferred target site(s) are those involved in mRNA splicing (i.e. splice donor sites, splice acceptor sites, or exonic splicing enhancer elements). Splicing branch points and exon recognition sequences or splice enhancers are also potential target sites for modulation of mRNA splicing.

Preferably, the present invention aims to provide antisense molecules capable of binding to a selected target in the dystrophin pre-mRNA to induce efficient and consistent exon skipping. Duchenne muscular dystrophy arises from mutations that preclude the synthesis of a functional dystrophin gene product. These Duchenne muscular dystrophy gene defects are typically nonsense mutations or genomic rearrangements such as deletions, duplications or micro-deletions or insertions that disrupt the reading frame. As the human dystrophin gene is a large and complex gene with the 79 exons being spliced together to generate a mature mRNA with an open reading frame of approximately 11,000 bases, there are many positions where these mutations can occur. Consequently, a comprehensive antisense oligonucleotide based therapy to address many of the different disease-causing mutations in the dystrophin gene will require that many exons can be targeted for removal during the splicing process.

Within the context of the present invention, preferred target site(s) are those involved in mRNA splicing (i.e. splice donor sites, splice acceptor sites or exonic splicing enhancer elements). Splicing branch points and exon recognition sequences or splice enhancers are also potential target sites for modulation of mRNA splicing.

The oligonucleotide and the DNA or RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the oligonucleotide and the DNA or RNA target. It is understood in the art that the sequence of an antisense molecule need not be 100% complementary to that of its target sequence to be specifically hybridisable. An antisense molecule is specifically hybridisable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

While the above method may be used to select antisense molecules capable of deleting any exon from within a protein that is capable of being shortened without affecting its biological function, the exon deletion should not lead to a reading frame shift in the shortened transcribed mRNA. Thus, if in a linear sequence of three exons the end of the first exon encodes two of three nucleotides in a codon and the next exon is deleted then the third exon in the linear sequence must start with a single nucleotide that is capable of completing the nucleotide triplet for a codon. If the third exon does not commence with a single nucleotide there will be a reading frame shift that would lead to the generation of truncated or a non-functional protein.

It will be appreciated that the codon arrangements at the end of exons in structural proteins may not always break at the end of a codon, consequently there may be a need to delete more than one exon from the pre-mRNA to ensure in-frame reading of the mRNA. In such circumstances, a plurality of antisense oligonucleotides may need to be selected by the method of the invention wherein each is directed to a different region responsible for inducing splicing in the exons that are to be deleted.

The length of an antisense molecule may vary so long as it is capable of binding selectively to the intended location within the pre-mRNA molecule. The length of such sequences can be determined in accordance with selection procedures described herein. Generally, the antisense molecule will be from about 10 nucleotides in length up to about 50 nucleotides in length. It will be appreciated however that any length of nucleotides within this range may be used in the method. Preferably, the length of the antisense molecule is between 17 to 30 nucleotides in length.

In order to determine which exons can be connected in a dystrophin gene, reference should be made to an exon boundary map. Connection of one exon with another is based on the exons possessing the same number at the 3' border as is present at the 5' border of the exon to which it is being connected. Therefore, if exon 7 were deleted, exon 6 must connect to either exons 12 or 18 to maintain the reading frame. Thus, antisense oligonucleotides would need to be selected which redirected splicing for exons 7 to 11 in the first instance or exons 7 to 17 in the second instance. Another and somewhat simpler approach to restore the reading frame around an exon 7 deletion would be to remove the two flanking exons. Induction of exons 6 and 8 skipping should result in an in-frame transcript with the splicing of exons 5 to 9. In practise however, targeting exon 8 for removal from the pre-mRNA results in the co-removal of exon 9 so the resultant transcript would have exon 5 joined to exon 10. The inclusion or exclusion of exon 9 does not alter the reading frame. Once the antisense molecules to be tested have been identified, they are prepared according to standard techniques known in the art. The most common method for producing antisense molecules is the methylation of the 2' hydroxyribose position and the incorporation of a phosphorothioate backbone produces molecules that superficially resemble RNA but that are much more resistant to nuclease degradation.

To avoid degradation of pre-mRNA during duplex formation with the antisense molecules, the antisense molecules used in the method may be adapted to minimise or prevent cleavage by endogenous RNase H. This property is highly preferred as the treatment of the RNA with the unmethylated oligonucleotides either intracellularly or in crude extracts that contain RNase H leads to degradation of the pre-mRNA: antisense oligonucleotide duplexes. Any form of modified antisense molecules that is capable of by-passing or not inducing such degradation may be used in the present method. An example of antisense molecules which when duplexed with RNA are not cleaved by cellular RNase H is 2'-O-methyl derivatives. 2'-O-methyl-oligoribonucleotides are very stable in a cellular environment and in animal tissues, and their duplexes with RNA have higher Tm values than their ribo- or deoxyribo- counterparts.

Antisense molecules that do not activate RNase H can be made in accordance with known techniques (see, e.g., U.S. Pat. No. 5,149,797). Such antisense molecules, which may be deoxyribonucleotide or ribonucleotide sequences, simply contain any structural modification which sterically hinders or prevents binding of RNase H to a duplex molecule containing the oligonucleotide as one member thereof, which structural modification does not substantially hinder or disrupt duplex formation. Because the portions of the oligonucleotide involved in duplex formation are substantially different from those portions involved in RNase H binding thereto, numerous antisense molecules that do not activate RNase H are available. For example, such antisense molecules may be oligonucleotides wherein at least one, or all, of the inter-nucleotide bridging phosphate residues are modified phosphates, such as methyl phosphonates, methyl phosphorothioates, phosphoromorpholidates, phosphoropiperazidates and phosphoramidates. For example, every other one of the internucleotide bridging phosphate residues may be modified as described. In another non-limiting example, such antisense molecules are molecules wherein at least one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

While antisense oligonucleotides are a preferred form of the antisense molecules, the present invention comprehends other oligomeric antisense molecules, including but not limited to oligonucleotide mimetics such as are described below.

Specific examples of preferred antisense compounds useful in this invention include oligonucleotides containing modified backbones or non-natural inter-nucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their inter-nucleoside backbone can also be considered to be oligonucleosides.

In other preferred oligonucleotide mimetics, both the sugar and the inter-nucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleo-bases are retained and are bound directly or indirectly to aza nitrogen atoms of the amide portion of the backbone.

Modified oligonucleotides may also contain one or more substituted sugar moieties. Oligonucleotides may also include nucleobase (often referred to in the art simply as "base") modifications or substitutions. Certain nucleo-bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Another modification of the oligonucleotides of the invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of this invention, are antisense molecules, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the increased resistance to nuclease degradation, increased cellular uptake, and an additional region for increased binding affinity for the target nucleic acid.

Methods of Manufacturing Antisense Molecules

The antisense molecules used in accordance with this invention may be conveniently and routinely made through the well-known technique of solid phase synthesis. Equipment for such synthesis is sold by several vendors including, for example, Applied Biosystems (Foster City, Calif.). One method for synthesising oligonucleotides on a modified solid support is described in U.S. Pat. No. 4,458,066.

Any other means for such synthesis known in the art may additionally or alternatively be employed. It is well known to use similar techniques to prepare oligonucleotides such as the phosphorothioates and alkylated derivatives. In one such automated embodiment, diethyl-phosphoramidites are used as starting materials and may be synthesized as described by Beaucage, et al., (1981) *Tetrahedron Letters,* 22:1859-1862.

The antisense molecules of the invention are synthesised in vitro and do not include antisense compositions of biological origin, or genetic vector constructs designed to direct the in vivo synthesis of antisense molecules. The molecules of the invention may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

Therapeutic Agents

The present invention also can be used as a prophylactic or therapeutic, which may be utilised for the purpose of treatment of a genetic disease.

Accordingly, in one embodiment the present invention provides antisense molecules that bind to a selected target in the dystrophin pre-mRNA to induce efficient and consistent exon skipping described herein in a therapeutically effective amount admixed with a pharmaceutically acceptable carrier, diluent, or excipient.

The phrase "pharmaceutically acceptable" refers to molecular entities and compositions that are physiologically tolerable and do not typically produce an allergic or similarly untoward reaction, such as gastric upset and the like, when administered to a patient. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences,* 18th Ed., Mack Publishing Co., Easton, Pa., (1990).

In a more specific form of the invention there are provided pharmaceutical compositions comprising therapeutically effective amounts of an antisense molecule together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Martin, *Remington's Pharmaceutical Sciences,* 18th Ed. (1990, Mack Publishing Co., Easton, Pa. 18042) pages 1435-1712 that are herein incorporated by reference. The compositions may be prepared in liquid form, or may be in dried powder, such as lyophilised form.

It will be appreciated that pharmaceutical compositions provided according to the present invention may be administered by any means known in the art. Preferably, the pharmaceutical compositions for administration are administered by injection, orally, or by the pulmonary, or nasal route. The antisense molecules are more preferably delivered by intravenous, intra-arterial, intraperitoneal, intramuscular, or subcutaneous routes of administration.

Antisense Molecule Based Therapy

Also addressed by the present invention is the use of antisense molecules of the present invention, for manufacture of a medicament for modulation of a genetic disease.

The delivery of a therapeutically useful amount of antisense molecules may be achieved by methods previously published. For example, intracellular delivery of the antisense molecule may be via a composition comprising an admixture of the antisense molecule and an effective amount of a block copolymer. An example of this method is described in US patent application US 20040248833.

Other methods of delivery of antisense molecules to the nucleus are described in Mann C J et al., (2001) ["*Antisense-induced exon skipping and the synthesis of dystrophin in the mdx mouse*". Proc. Natl. Acad. Science, 98(1) 42-47] and in Gebski et al., (2003). Human Molecular Genetics, 12(15): 1801-1811.

A method for introducing a nucleic acid molecule into a cell by way of an expression vector either as naked DNA or complexed to lipid carriers, is described in U.S. Pat. No. 6,806,084.

It may be desirable to deliver the antisense molecule in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations.

Liposomes are artificial membrane vesicles which are useful as delivery vehicles in vitro and in vivo. These formulations may have net cationic, anionic or neutral charge characteristics and are useful characteristics with in vitro, in vivo and ex vivo delivery methods. It has been shown that large unilamellar vesicles (LUV), which range in size from 0.2-4.0 .PHI.m can encapsulate a substantial percentage of an aqueous buffer containing large macromolecules. RNA, and DNA can be encapsulated within the aqueous interior and be delivered to cells in a biologically active form (Fraley, et al., Trends Biochem. Sci., 6:77, 1981).

In order for a liposome to be an efficient gene transfer vehicle, the following characteristics should be present: (1) encapsulation of the antisense molecule of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Alternatively, the antisense construct may be combined with other pharmaceutically acceptable carriers or diluents to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

The routes of administration described are intended only as a guide since a skilled practitioner will be able to determine readily the optimum route of administration and any dosage for any particular animal and condition. Multiple approaches for introducing functional new genetic material into cells, both in vitro and in vivo have been attempted (Friedmann (1989) Science, 244:1275-1280).

These approaches include integration of the gene to be expressed into modified retroviruses (Friedmann (1989) supra; Rosenberg (1991) Cancer Research 51(18), suppl.: 5074S-5079S); integration into non-retrovirus vectors (Rosenfeld, et al. (1992) Cell, 68:143-155; Rosenfeld, et al. (1991) Science, 252:431-434); or delivery of a transgene linked to a heterologous promoter-enhancer element via liposomes (Friedmann (1989), supra; Brigham, et al. (1989) Am. J. Med. Sci., 298:278-281; Nabel, et al. (1990) Science, 249: 1285-1288; Hazinski, et al. (1991) Am. J. Resp. Cell Molec. Biol., 4:206-209; and Wang and Huang (1987) Proc. Natl. Acad. Sci. (USA), 84:7851-7855); coupled to ligand-specific, cation-based transport systems (Wu and Wu (1988) J. Biol. Chem., 263:14621-14624) or the use of naked DNA, expression vectors (Nabel et al. (1990), supra); Wolff et al. (1990) Science, 247:1465-1468). Direct injection of transgenes into tissue produces only localized expression (Rosenfeld (1992) supra); Rosenfeld et al. (1991) supra; Brigham et al. (1989) supra; Nabel (1990) supra; and Hazinski et al. (1991) supra). The Brigham et al. group (Am. J. Med. Sci. (1989) 298:278-281 and Clinical Research (1991) 39 (abstract)) have reported in vivo transfection only of lungs of mice following either intravenous or intratracheal administration of a DNA liposome complex. An example of a review article of human gene therapy procedures is: Anderson, Science (1992) 256:808-813.

The antisense molecules of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The pharmaceutical compositions of the present invention may be administered in a number of ways depending upon whether local or systemic treatment is desired and upon the area to be treated. Administration may be topical (including ophthalmic and to mucous membranes including rectal delivery), pulmonary, e.g., by inhalation or insufflation of powders or aerosols, (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Kits of the Invention

The invention also provides kits for treatment of a patient with a genetic disease which kit comprises at least an antisense molecule, packaged in a suitable container, together with instructions for its use.

In a preferred embodiment, the kits will contain at least one antisense molecule as shown in Table 1A, or a cocktail of antisense molecules as shown in Table 1B or a "weasel" compound as shown in Table 1C. The kits may also contain peripheral reagents such as buffers, stabilizers, etc.

Those of ordinary skill in the field should appreciate that applications of the above method has wide application for identifying antisense molecules suitable for use in the treatment of many other diseases.

EXAMPLES

The following Examples serve to more fully describe the manner of using the above-described invention, as well as to set forth the best modes contemplated for carrying out various aspects of the invention. It is understood that these Examples in no way serve to limit the true scope of this invention, but rather are presented for illustrative purposes. The references cited herein are expressly incorporated by reference.

Methods of molecular cloning, immunology and protein chemistry, which are not explicitly described in the following examples, are reported in the literature and are known by those skilled in the art. General texts that described conventional molecular biology, microbiology, and recombinant DNA techniques within the skill of the art, included, for example: Sambrook et al., *Molecular Cloning: A Laboratory Manual*, Second Edition, Cold Spring Harbor Laboratory Press, Cold Spring Harbor, N.Y. (1989); Glover ed., *DNA Cloning: A Practical Approach*, Volumes I and II, MRL Press, Ltd., Oxford, U.K. (1985); and Ausubel, F., Brent, R., Kingston, R. E., Moore, D. D., Seidman, J. G., Smith, J. A., Struhl, K. *Current Protocols in Molecular Biology*. Greene Publishing Associates/Wiley Intersciences, New York (2002).

Determining Induced Exon Skipping in Human Muscle Cells

Attempts by the inventors to develop a rational approach in antisense molecules design were not completely successful as there did not appear to be a consistent trend that could be applied to all exons. As such, the identification of the most effective and therefore most therapeutic antisense molecules compounds has been the result of empirical studies.

These empirical studies involved the use of computer programs to identify motifs potentially involved in the splicing process. Other computer programs were also used to identify regions of the pre-mRNA which may not have had extensive secondary structure and therefore potential sites for annealing of antisense molecules. Neither of these approaches proved completely reliable in designing antisense oligonucleotides for reliable and efficient induction of exon skipping.

Annealing sites on the human dystrophin pre-mRNA were selected for examination, initially based upon known or predicted motifs or regions involved in splicing. 2OMe antisense oligonucleotides were designed to be complementary to the target sequences under investigation and were synthesised on an Expedite 8909 Nucleic Acid Synthesiser. Upon completion of synthesis, the oligonucleotides were cleaved from the support column and de-protected in ammonium hydroxide before being desalted. The quality of the oligonucleotide synthesis was monitored by the intensity of the trityl signals upon each deprotection step during the synthesis as detected in the synthesis log. The concentration of the antisense oligonucleotide was estimated by measuring the absorbance of a diluted aliquot at 260 nm.

Specified amounts of the antisense molecules were then tested for their ability to induce exon skipping in an in vitro assay, as described below.

Briefly, normal primary myoblast cultures were prepared from human muscle biopsies obtained after informed consent. The cells were propagated and allowed to differentiate into myotubes using standard culturing techniques. The cells were then transfected with the antisense oligonucleotides by delivery of the oligonucleotides to the cells as cationic lipoplexes, mixtures of antisense molecules or cationic liposome preparations.

The cells were then allowed to grow for another 24 hours, after which total RNA was extracted and molecular analysis commenced. Reverse transcriptase amplification (RT-PCR) was undertaken to study the targeted regions of the dystrophin pre-mRNA or induced exonic re-arrangements.

For example, in the testing of an antisense molecule for inducing exon 19 skipping the RT-PCR test scanned several exons to detect involvement of any adjacent exons. For example, when inducing skipping of exon 19, RT-PCR was carried out with primers that amplified across exons 17 and 21. Amplifications of even larger products in this area (i.e. exons 13-26) were also carried out to ensure that there was minimal amplification bias for the shorter induced skipped transcript. Shorter or exon skipped products tend to be amplified more efficiently and may bias the estimated of the normal and induced transcript.

The sizes of the amplification reaction products were estimated on an agarose gel and compared against appropriate size standards. The final confirmation of identity of these products was carried out by direct DNA sequencing to establish that the correct or expected exon junctions have been maintained.

Once efficient exon skipping had been induced with one antisense molecule, subsequent overlapping antisense molecules may be synthesized and then evaluated in the assay as described above. Our definition of an efficient antisense molecule is one that induces strong and sustained exon skipping at transfection concentrations in the order of 300 nM or less.

Antisense Oligonucleotides Directed at Exon 8

Antisense oligonucleotides directed at exon 8 were prepared and tested for their ability to induce exon skipping in human muscle cells using similar methods as described above.

Figure 3:
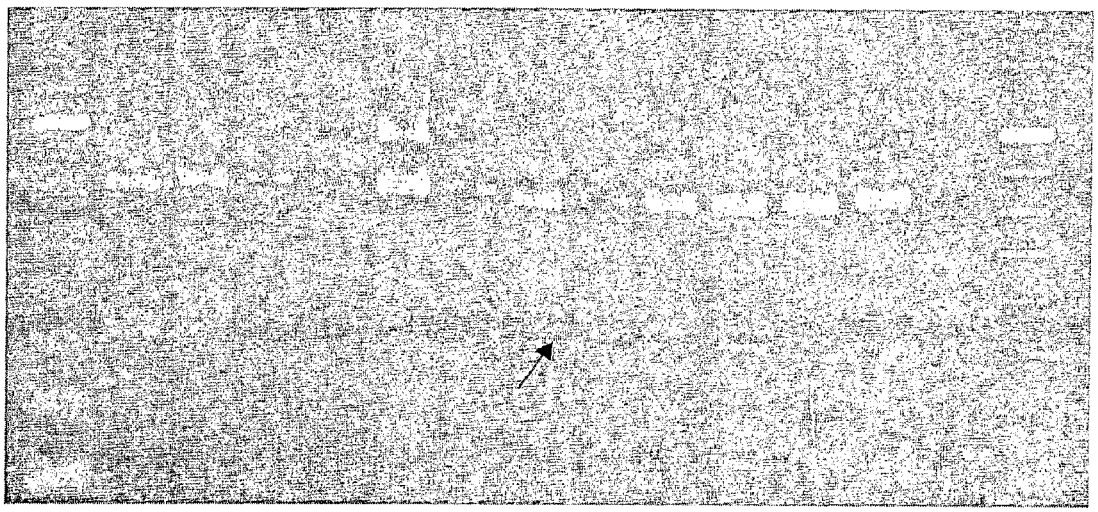
FIG. 3 Gel electrophoresis showing differing efficiencies of two antisense molecules directed at exon 8 acceptor splice site. The preferred compound [H8A(−06+18)] induces strong and consistent exon skipping at a transfection concentration of 20 nanomolar in cultured normal human muscle cells. The less preferred antisense oligonucleotide [H8A(−06+14)] also induces efficient exon skipping, but at much higher concentrations. Other antisense oligonucleotides directed at exon 8 either only induced lower levels of exon skipping or no detectable skipping at all (not shown).

FIG. 3 shows differing efficiencies of two antisense molecules directed at exon 8 acceptor splice site. H8A(−06+18) [SEQ ID NO:1], which anneals to the last 6 bases of intron 7 and the first 18 bases of exon 8, induces substantial exon 8 and 9 skipping when delivered into cells at a concentration of 20 nM. The shorter antisense molecule, H8A(−06+14) [SEQ ID NO: 4] was only able to induce exon 8 and 9 skipping at 300 nM, a concentration some 15 fold higher than H8A(−06+18), which is the preferred antisense molecule.

This data shows that some particular antisense molecules induce efficient exon skipping while another antisense molecule, which targets a near-by or overlapping region, can be much less efficient. Titration studies show one compound is able to induce targeted exon skipping at 20 nM while the less efficient antisense molecules only induced exon skipping at concentrations of 300 nM and above. Therefore, we have shown that targeting of the antisense molecules to motifs involved in the splicing process plays a crucial role in the overall efficacy of that compound.

Efficacy refers to the ability to induce consistent skipping of a target exon. However, sometimes skipping of the target exons is consistently associated with a flanking exon. That is, we have found that the splicing of some exons is tightly linked. For example, in targeting exon 23 in the mouse model of muscular dystrophy with antisense molecules directed at the donor site of that exon, dystrophin transcripts missing exons 22 and 23 are frequently detected. As another example, when using an antisense molecule directed to exon 8 of the human dystrophin gene, all induced transcripts are missing both exons 8 and 9. Dystrophin transcripts missing only exon 8 are not observed.

Table 2 below discloses antisense molecule sequences that induce exon 8 (and 9) skipping.

TABLE 2

| Antisense Oligo-nucleotide name | Sequence | Ability to induce skipping |
|---|---|---|
| H8A(−06+18) | 5'-GAU AGG UGG UAU CAA CAU CUG UAA | Very strong to 20 nM |
| H8A(−03+18) | 5'-GAU AGG UGG UAU CAA CAU CUG | Very strong skipping to 40 nM |
| H8A(−07+18) | 5'-GAU AGG UGG UAU CAA CAU CUG UAA G | Strong skipping to 40 nM |
| H8A(−06+14) | 5'-GGU GGU AUC AAC AUC UGU AA | Skipping to 300 nM |
| H8A(−10+10) | 5'-GUA UCA ACA UCU GUA AGC AC | Patchy/weak skipping to 100 nm |

Antisense Oligonucleotides Directed at Exon 7

Antisense oligonucleotides directed at exon 7 were prepared and tested for their ability to induce exon skipping in human muscle cells using similar methods as described above.

Figure 4:
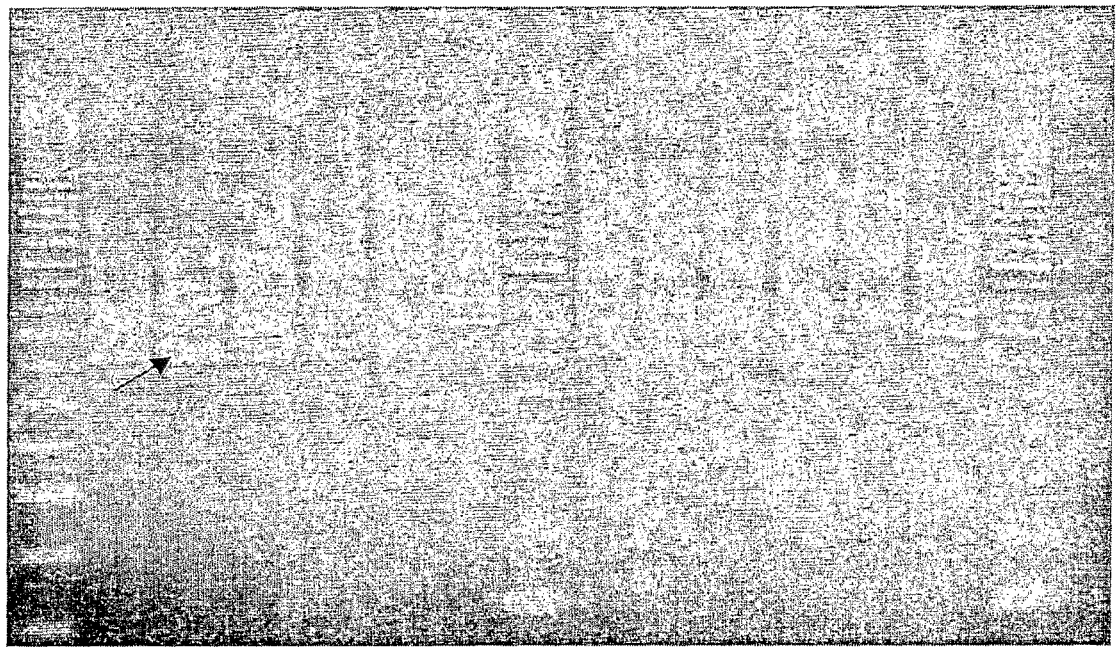
FIG. 4 Gel electrophoresis showing differing efficiencies of two antisense molecules directed at internal domains within exon 7, presumably exon splicing enhancers. The preferred compound [H7A(+45+67)] induces strong and consistent exon skipping at a transfection concentration of 20 nanomolar in cultured human muscle cells. The less preferred antisense oligonucleotide [H7A(+2+26)] induces only low levels of exon skipping at the higher transfection concentrations. Other antisense oligonucleotides directed at exon 7 either only induced lower levels of exon skipping or no detectable skipping at all (not shown).

FIG. 4 shows the preferred antisense molecule, H7A(+45+67) [SEQ ID NO: 6], and another antisense molecule, H7A(+2+26) [SEQ ID NO: 7], inducing exon 7 skipping. Nested amplification products span exons 3 to 9. Additional products above the induced transcript missing exon 7 arise from amplification from carry-over outer primers from the RT-PCR as well as heteroduplex formation.

Table 3 below discloses antisense molecule sequences for induced exon 7 skipping.

TABLE 3

| Antisense Oligo-nucleotide name | Sequence | Ability to induce skipping |
|---|---|---|
| H7A(+45+67) | 5'-UGC AUG UUC CAG UCG UUG UGU GG | Strong skipping to 20 nM |
| H7A(+02+26) | 5'-CAC UAU UCC AGU CAA AUA GGU CUG G | Weak skipping at 100 nM |
| H7D(+15−10) | 5'-AUU UAC CAA CCU UCA GGA UCG AGU A | Weak skipping to 300 nM |
| H7A(−18+03) | 5'-GGC CUA AAA CAC AUA CAC AUA | Weak skipping to 300 nM |

Antisense Oligonucleotides Directed at Exon 6

Antisense oligonucleotides directed at exon 6 were prepared and tested for their ability to induce exon skipping in human muscle cells using similar methods as described above.

Figure 5:
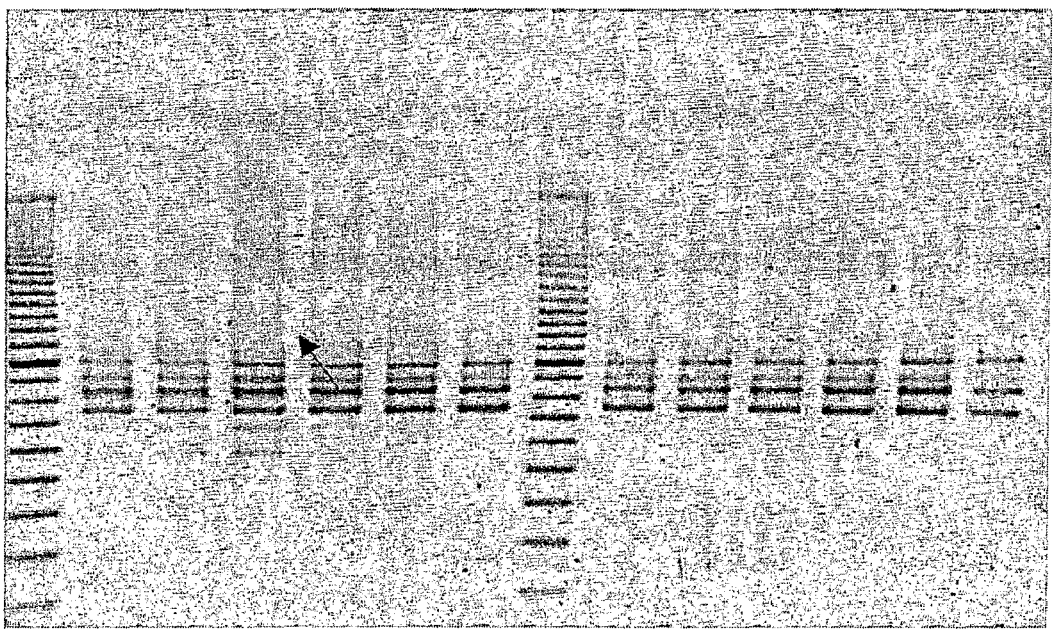
FIG. 5 Gel electrophoresis showing an example of low efficiency exon 6 skipping using two non-preferred antisense molecules directed at human exon 6 donor splice site. Levels of induced exon 6 skipping are either very low [H6D(+04−21)] or almost undetectable [H6D(+18−04)]. These are examples of non-preferred antisense oligonucleotides to demonstrate that antisense oligonucleotide design plays a crucial role in the efficacy of these compounds.

FIG. 5 shows an example of two non-preferred antisense molecules inducing very low levels of exon 6 skipping in cultured human cells. Targeting this exon for specific removal was first undertaken during a study of the canine model using the oligonucleotides as listed in Table 4, below. Some of the human specific oligonucleotides were also evaluated, as shown in FIG. 5. In this example, both antisense molecules target the donor splice site and only induced low levels of exon 6 skipping. Both H6D(+4−21) [SEQ ID NO: 17] and H6D(+18−4) [SEQ ID NO: 18] would be regarded as non-preferred antisense molecules.

Figure 6:
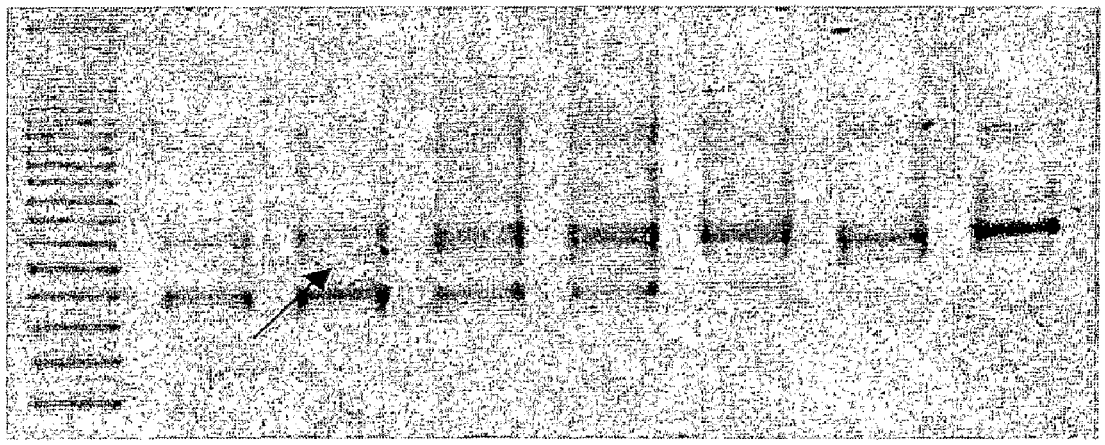
FIG. 6 Gel electrophoresis showing strong and efficient human exon 6 skipping using an antisense molecules [H6A(+69+91)] directed at an exon 6 internal domain, presumably an exon splicing enhancer. This preferred compound induces consistent exon skipping at a transfection concentration of 20 nanomolar in cultured human muscle cells.

One antisense oligonucleotide that induced very efficient exon 6 skipping in the canine model, C6A(+69+91) [SEQ ID NO: 14], would anneal perfectly to the corresponding region in human dystrophin exon 6. This compound was evaluated, found to be highly efficient at inducing skipping of that target exon, as shown in FIG. 6 and is regarded as the preferred compound for induced exon 6 skipping. Table 4 below discloses antisense molecule sequences for induced exon 6 skipping.

TABLE 4

| Antisense Oligo name | Sequence | Ability to induce skipping |
|---|---|---|
| C6A(−10+10) | 5' CAU UUU UGA CCU ACA UGU GG | No skipping |
| C6A(−14+06) | 5' UUU GAC CUA CAU GUG GAA AG | No skipping |
| C6A(−14+12) | 5' UAC AUU UUU GAC CUA CAU GUG GAA AG | No skipping |
| C6A(−13+09) | 5' AUU UUU GAC CUA CAU GGG AAA G | No skipping |
| CH6A(+69+91) | 5' UAC GAG UUG AUU GUC GGA CCC AG | Strong skipping to 20 nM |

TABLE 4-continued

| Antisense Oligo name | Sequence | Ability to induce skipping |
|---|---|---|
| C6D(+12-13) | 5' GUG GUC UCC UUA CCU AUG ACU GUG G | Weak skipping at 300 nM |
| C6D(+06-11) | 5' GGU CUC CUU ACC UAU GA | No skipping |
| H6D(+04-21) | 5' UGU CUC AGU AAU CUU CUU ACC UAU | Weak skipping to 50 nM |
| H6D(+18-04) | 5' UCU UAC CUA UGA CUA UGG AUG AGA | Very weak skipping to 300 nM |

Antisense Oligonucleotides Directed at Exon 4

Antisense oligonucleotides directed at exon 4 were prepared and tested for their ability to induce exon skipping in human muscle cells using similar methods as described above.

Figure 7:
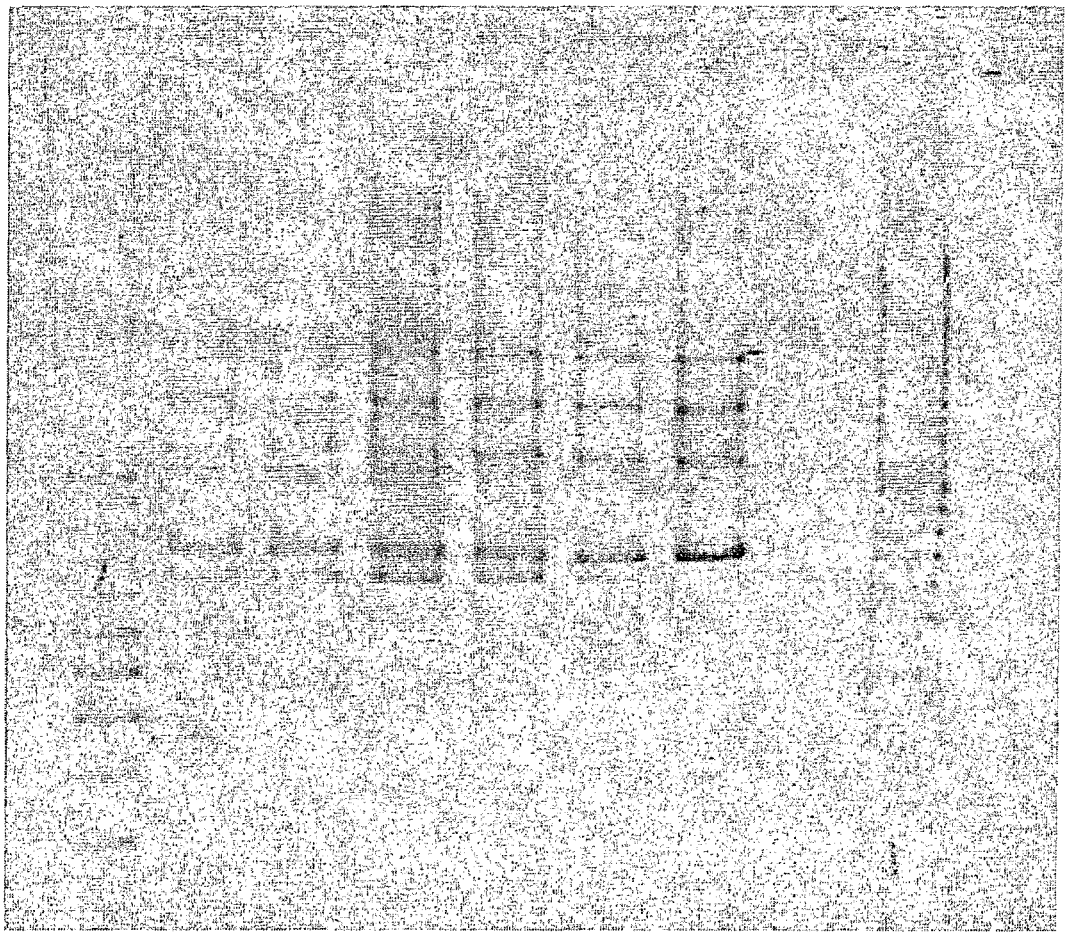
FIG. 7 Gel electrophoresis showing strong human exon 4 skipping using an antisense molecule H4A(+13+32) directed at an exon 6 internal domain, presumably an exon splicing enhancer. This preferred compound induces strong and consistent exon skipping at a transfection concentration of 20 nanomolar in cultured human muscle cells.

FIG. 7 shows an example of a preferred antisense molecule inducing skipping of exon 4 skipping in cultured human cells. In this example, one preferred antisense compound, H4A(+13+32) [SEQ ID NO:19], which targeted a presumed exonic splicing enhancer induced efficient exon skipping at a concentration of 20 nM while other non-preferred antisense oligonucleotides failed to induce even low levels of exon 4 skipping. Another preferred antisense molecule inducing skipping of exon 4 was H4A(+111+40) [SEQ ID NO:22], which induced efficient exon skipping at a concentration of 20 nM.

Table 5 below discloses antisense molecule sequences for inducing exon 4 skipping.

TABLE 5

| Antisense Oligo-nucleotide name | Sequence | Ability to induce skipping |
|---|---|---|
| H4A(+13+32) | 5' GCA UGA ACU CUU GUG GAU CC | Skipping to 20 nM |
| H4A(+11+40) | 5'UGU UCA GGG CAU GAA CUC UUG UGG AUC CUU | Skipping to 20 nM |
| H4D(+04-16) | 5' CCA GGG UAC UAC UUA CAU UA | No skipping |
| H4D(-24-44) | 5' AUC GUG UGU CAC AGC AUC CAG | No skipping |

Antisense Oligonucleotides Directed at Exon 3

Antisense oligonucleotides directed at exon 3 were prepared and tested for their ability to induce exon skipping in human muscle cells using similar methods as described above.

H3A(+30+60) [SEQ ID NO:23] induced substantial exon 3 skipping when delivered into cells at a concentration of 20 nM to 600 nM. The antisense molecule, H3A(+35+65) [SEQ ID NO: 24] induced exon skipping at 300 nM.

Table 6 below discloses antisense molecule sequences that induce exon 3 skipping.

TABLE 6

| Antisense Oligonucleotide name | Sequence | Ability to induce skipping |
|---|---|---|
| H3A(+30+60) | UAG GAG GCG CCU CCC AUC CUG UAG GUC ACU G | Moderate skipping to 20 to 600 nM |
| H3A(+35+65) | AGG UCU AGG AGG CGC CUC CCA UCC UGU AGG U | Working to 300 nM |
| H3A(+30+54) | GCG CCU CCC AUC CUG UAG GUC ACU G | Moderate 100-600 nM |
| H3D(+46-21) | CUU CGA GGA GGU CUA GGA GGC GCC UC | No skipping |
| H3A(+30+50) | CUC CCA UCC UGU AGG UCA CUG | Moderate 20-600 nM |
| H3D(+19-03) | UAC CAG UUU UUG CCC UGU CAG G | No skipping |
| H3A(-06+20) | UCA AUA UGC UGC UUCCCA AAC UGA AA | No skipping |
| H3A(+37+61) | CUA GGA GGC GCC UCC CAU CCU GUA G | No skipping |

Antisense Oligonucleotides Directed at Exon 5

Antisense oligonucleotides directed at exon 5 were prepared and tested for their ability to induce exon skipping in human muscle cells using similar methods as described above.

H5A(+20+50) [SEQ ID NO:31] induces substantial exon 5 skipping when delivered into cells at a concentration of 100 nM. Table 7 below shows other antisense molecules tested. The majority of these antisense molecules were not as effective at exon skipping as H5A(+20+50). However, H5A(+15+45) [SEQ ID NO: 40] was able to induce exon 5 skipping at 300 nM.

Table 7 below discloses antisense molecule sequences that induce exon 5 skipping.

TABLE 7

| Antisense Oligonucleotide name | Sequence | Ability to induce skipping |
|---|---|---|
| H5A(+20+50) | UUA UGA UUU CCA UCU ACG AUG UCA GUA CUU C | Working to 100 nM |
| H5D(+25-05) | CUU ACC UGC CAG UGG AGG AUU AUA UUC CAA A | No skipping |
| H5D(+10-15) | CAU CAG GAU UCU UAC CUG CCA GUG G | Inconsistent at 300 nM |
| H5A(+10+34) | CGA UGU CAG UAC UUC CAA UAU UCA C | Very weak |
| H5D(-04-21) | ACC AUU CAU CAG GAU UCU | No skipping |

TABLE 7-continued

| Antisense Oligonucleotide name | Sequence | Ability to induce skipping |
|---|---|---|
| H5D(+16-02) | ACC UGC CAG UGG AGG AUU | No skipping |
| H5A(-07+20) | CCA AUA UUC ACU AAA UCA ACC UGU UAA | No skipping |
| H5D(+18-12) | CAG GAU UCU UAC CUG CCA GUG GAG GAU UAU | No skipping |
| H5A(+05+35) | ACG AUG UCA GUA CUU CCA AUA UUC ACU AAA U | No skipping |
| H5A(+15+45) | AUU UCC AUC UAC GAU GUC AGU ACU UCC AAU A | Working to 300 nM |

Antisense Oligonucleotides Directed at Exon 10

Antisense oligonucleotides directed at exon 10 were prepared and tested for their ability to induce exon skipping in human muscle cells using similar methods as described above.

H10A(−05+16) [SEQ ID NO:41] induced substantial exon 10 skipping when delivered into cells. Table 8 below shows other antisense molecules tested. The antisense molecules ability to induce exon skipping was variable. Table 8 below discloses antisense molecule sequences that induce exon 10 skipping.

TABLE 8

| Antisense Oligonucleotide name | Sequence | Ability to induce skipping |
|---|---|---|
| H10A(-05+16) | CAG GAG CUU CCA AAU GCU GCA | Not tested |
| H10A(-05+24) | CUU GUC UUC AGG AGC UUC CAA AUG CUG CA | Not tested |
| H10A(+98+119) | UCC UCA GCA GAA AGA AGC CAC G | Not tested |
| H10A(+130+149) | UUA GAA AUC UCU CCU UGU GC | No skipping |
| H10A(-33-14) | UAA AUU GGG UGU UAC ACA AU | No skipping |

Antisense Oligonucleotides Directed at Exon 11

Antisense oligonucleotides directed at exon 11 were prepared and tested for their ability to induce exon skipping in human muscle cells using similar methods as described above.

Figure 8:
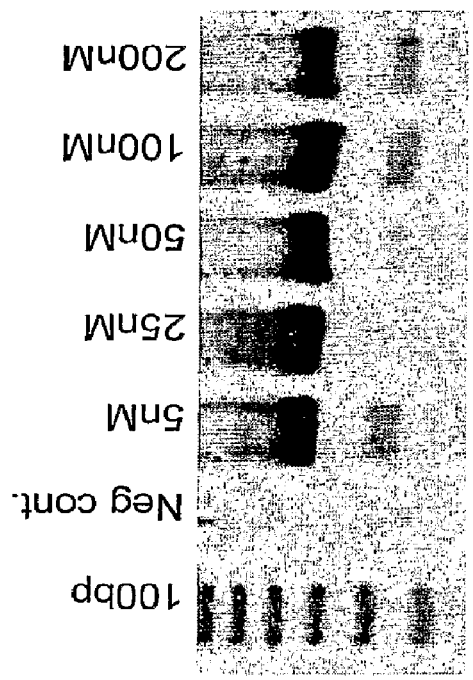
FIG. 8 Gel electrophoresis showing (8B) strong human exon 11 skipping using antisense molecule H11A(+75+97) directed at an exon 11 internal domain; and (8B) strong human exon 12 skipping using antisense molecule H12A(+52+75) directed at exon 12 internal domain.
Figure 8:
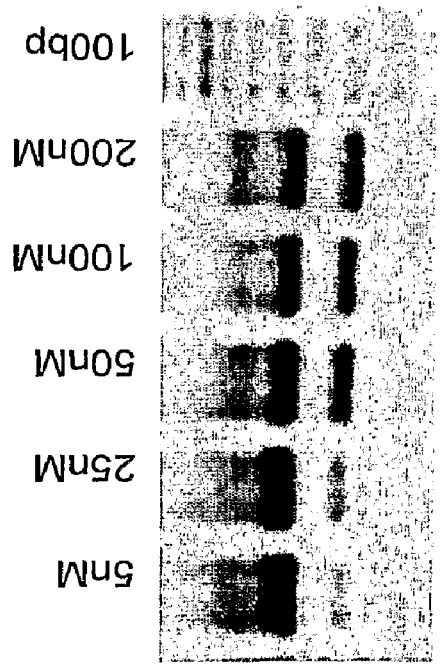

FIG. 8B shows an example of H11A(+75+97) [SEQ ID NO:49] antisense molecule inducing exon 11 skipping in cultured human cells. H11A(+75+97) induced substantial exon 11 skipping when delivered into cells at a concentration of 5 nM. Table 9 below shows other antisense molecules tested. The antisense molecules ability to induce exon skipping was observed at 100 nM.

TABLE 9

| Antisense Oligonucleotide name | Sequence | Ability to induce skipping |
|---|---|---|
| H11D(+26+49) | CCC UGA GGC AUU CCC AUC UUG AAU | Skipping at 100 nM |
| H11D(+11-09) | AGG ACU UAC UUG CUU UGU UU | Skipping at 100 nM |
| H11A(+118+140) | CUU GAA UUU AGG AGA UUC AUC UG | Skipping at 100 nM |
| H11A(+75+97) | CAU CUU CUG AUA AUU UUC CUG UU | Skipping at 100 nM |
| H11D(+26+49) | CCC UGA GGC AUU CCC AUC UUG AAU | Skipping at 5 nM |

Antisense Oligonucleotides Directed at Exon 12

Antisense oligonucleotides directed at exon 12 were prepared and tested for their ability to induce exon skipping in human muscle cells using similar methods as described above.

H12A(+52+75) [SEQ ID NO:50] induced substantial exon 12 skipping when delivered into cells at a concentration of 5 nM, as shown in FIG. 8A. Table 10 below shows other antisense molecules tested at a concentration range of 5, 25, 50, 100, 200 and 300 nM. The antisense molecules ability to induce exon skipping was variable.

TABLE 10

| Antisense Oligonucleotide name | Sequence | Ability to induce skipping |
|---|---|---|
| H12A(+52+75) | UCU UCU GUU UUU GUU AGC CAG UCA | Skipping at 5 nM |
| H12A(-10+10) | UCU AUG UAA ACU GAA AAU UU | Skipping at 100 nM |
| H12A(+11+30) | UUC UGG AGA UCC AUU AAA AC | No skipping |

Antisense Oligonucleotides Directed at Exon 13

Antisense oligonucleotides directed at exon 13 were prepared and tested for their ability to induce exon skipping in human muscle cells using similar methods as described above.

H13A(+77+100) [SEQ ID NO:53] induced substantial exon 13 skipping when delivered into cells at a concentration of 5 nM. Table 11 below includes two other antisense molecules tested at a concentration range of 5, 25, 50, 100, 200 and 300 nM. These other antisense molecules were unable to induce exon skipping.

TABLE 11

| Antisense Oligonucleotide name | Sequence | Ability to induce skipping |
|---|---|---|
| H13A(+77+100) | CAG CAG UUG CGU GAU CUC CAC UAG | Skipping at 5 nM |
| H13A(+55+75) | UUC AUC AAC UAC CAC CAC CAU | No skipping |
| H13D(+06-19) | CUA AGC AAA AUA AUC UGA CCU UAA G | No skipping |

Antisense Oligonucleotides Directed at Exon 14

Antisense oligonucleotides directed at exon 14 were prepared and tested for their ability to induce exon skipping in human muscle cells using similar methods as described above.

H14A(+37+64) [SEQ ID NO:56] induced weak exon 14 skipping when delivered into cells at a concentration of 100 nM. Table 12 below includes other antisense molecules tested at a concentration range of 5, 25, 50, 100, 200 and 300 nM. The other antisense molecules were unable to induce exon skipping at any of the concentrations tested.

TABLE 12

| Antisense Oligonucleotide name | Sequence | Ability to induce skipping |
|---|---|---|
| H14A(+37+64) | CUU GUA AAA GAA CCC AGC GGU CUU CUG U | Skipping at 100 nM |
| H14A(+14+35) | CAU CUA CAG AUG UUU GCC CAU C | No skipping |
| H14A(+51+73) | GAA GGA UGU CUU GUA AAA GAA CC | No skipping |
| H14D(-02+18) | ACC UGU UCU UCA GUA AGA CG | No skipping |
| H14D(+14-10) | CAU GAC ACA CCU GUU CUU CAG UAA | No skipping |
| H14A(+61+80) | CAU UUG AGA AGG AUG UCU UG | No skipping |
| H14A(-12+12) | AUC UCC CAA UAC CUG GAG AAG AGA | No skipping |

Antisense Oligonucleotides Directed at Exon 15

Antisense oligonucleotides directed at exon 15 were prepared and tested for their ability to induce exon skipping in human muscle cells using similar methods as described above.

Figure 9:
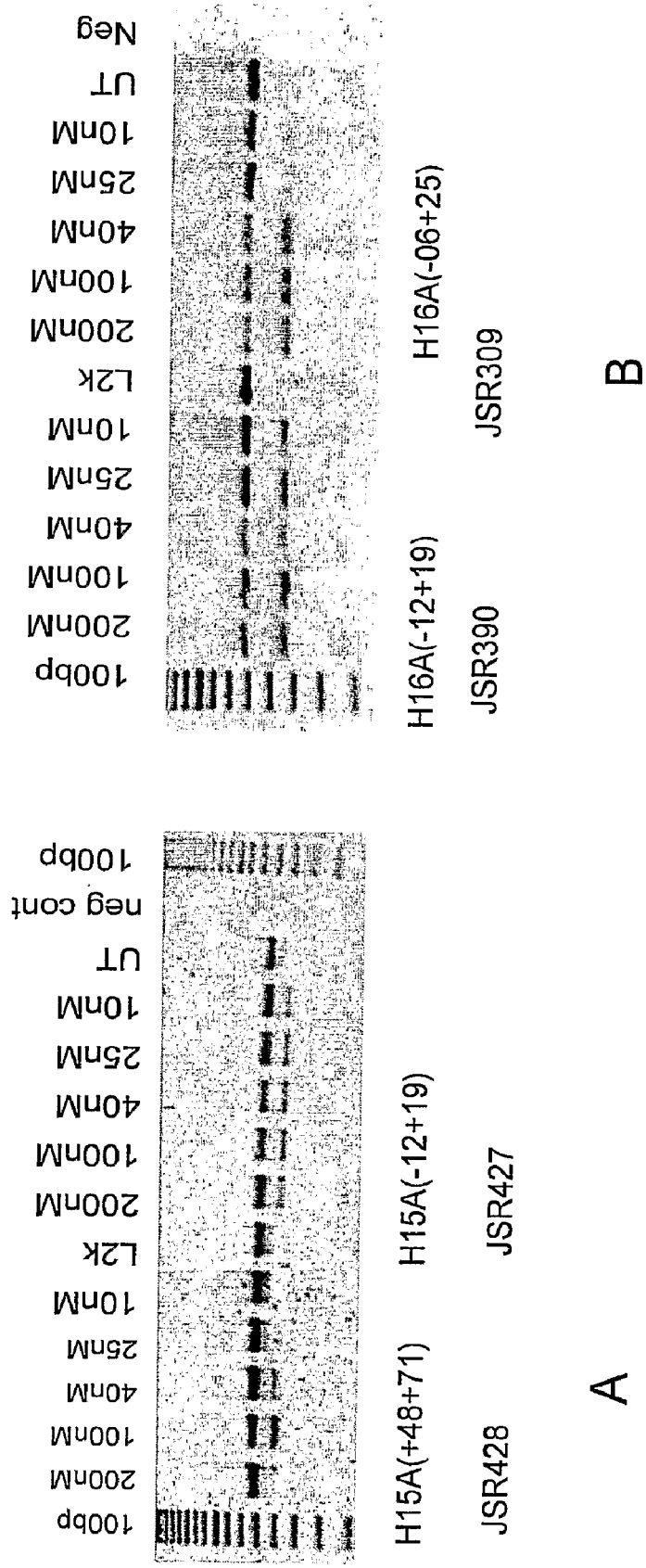
FIG. 9 Gel electrophoresis showing (9A) strong human exon 15 skipping using antisense molecules H15A(+48+71) and H15A(−12+19) directed at an exon 15 internal domain; and (9B) strong human exon 16 skipping using antisense molecules H16A(−12+19) and H16A(−06+25).

H15A(-12+19) [SEQ ID NO:63] and H15A(+48+71) [SEQ ID NO:64] induced substantial exon 15 skipping when delivered into cells at a concentration of 10 Nm, as shown in FIG. 9A. Table 13 below includes other antisense molecules tested at a concentration range of 5, 25, 50, 100, 200 and 300 Nm. These other antisense molecules were unable to induce exon skipping at any of the concentrations tested.

TABLE 13

| Antisense Oligonucleotide name | Sequence | Ability to induce skipping |
|---|---|---|
| H15A(-12+19) | GCC AUG CAC UAA AAA GGC ACU GCA AGA CAU U | Skipping at 5 Nm |
| H15A(+48+71) | UCU UUA AAG CCA GUU GUG UGA AUC | Skipping at 5 Nm |
| H15A(+08+28) | UUU CUG AAA GCC AUG CAC UAA | No skipping |
| H15A(-12+19) | GCC AUG CAC UAA AAA GGC ACU GCA AGA CAU U | No skipping |
| H15D(+17-08) | GUA CAU ACG GCC AGU UUU UGA AGA C | No skipping |

Antisense Oligonucleotides Directed at Exon 16

Antisense oligonucleotides directed at exon 16 were prepared and tested for their ability to induce exon skipping in human muscle cells using similar methods as described above.

H16A(-12+19) [SEQ ID NO:67] and H16A(-06+25) [SEQ ID NO:68] induced substantial exon 16 skipping when delivered into cells at a concentration of 10 nM, as shown in FIG. 9B. Table 14 below includes other antisense molecules tested. H16A(-06+19) [SEQ ID NO:69] and H16A(+87+109) [SEQ ID NO:70] were tested at a concentration range of 5, 25, 50, 100, 200 and 300 nM. These two antisense molecules were able to induce exon skipping at 25 nM and 100 nM, respectively. Additional antisense molecules were tested at 100, 200 and 300 nM and did not result in any exon skipping.

TABLE 14

| Antisense Oligonucleotide name | Sequence | Ability to induce skipping |
|---|---|---|
| H16A(-12+19) | CUA GAU CCG CUU UUA AAA CCU GUU AAA ACA A | Skipping at 5 nM |
| H16A(-06+25) | UCU UUU CUA GAU CCG CUU UUA AAA CCU GUU A | Skipping at 5 nM |
| H16A(-06+19) | CUA GAU CCG CUU UUA AAA CCU GUU A | Skipping at 25 nM |
| H16A(+87+109) | CCG UCU UCU GGG UCA CUG ACU UA | Skipping at 100 nM |
| H16A(-07+19) | CUA GAU CCG CUU UUA AAA CCU GUU AA | No skipping |
| H16A(-07+13) | CCG CUU UUA AAA CCU GUU AA | No skipping |
| H16A(+12+37) | UGG AUU GCU UUU UCU UUU CUA GAU CC | No skipping |
| H16A(+92+116) | CAU GCU UCC GUC UUC UGG GUC ACU G | No skipping |
| H16A(+45+67) | G AUC UUG UUU GAG UGA AUA CAG U | No skipping |
| H16A(+105+126) | GUU AUC CAG CCA UGC UUC CGU C | No skipping |
| H16D(+05-20) | UGA UAA UUG GUA UCA CUA ACC UGU G | No skipping |
| H16D(+12-11) | GUA UCA CUA ACC UGU GCU GUA C | No skipping |

Antisense Oligonucleotides Directed at Exon 19

Antisense oligonucleotides directed at exon 19 were prepared and tested for their ability to induce exon skipping in human muscle cells using similar methods as described above.

H19A(+35+65) [SEQ ID NO:79] induced substantial exon 19 skipping when delivered into cells at a concentration of 10 nM. This antisense molecule also showed very strong exon skipping at concentrations of 25, 50, 100, 300 and 600 nM.

Figure 10:
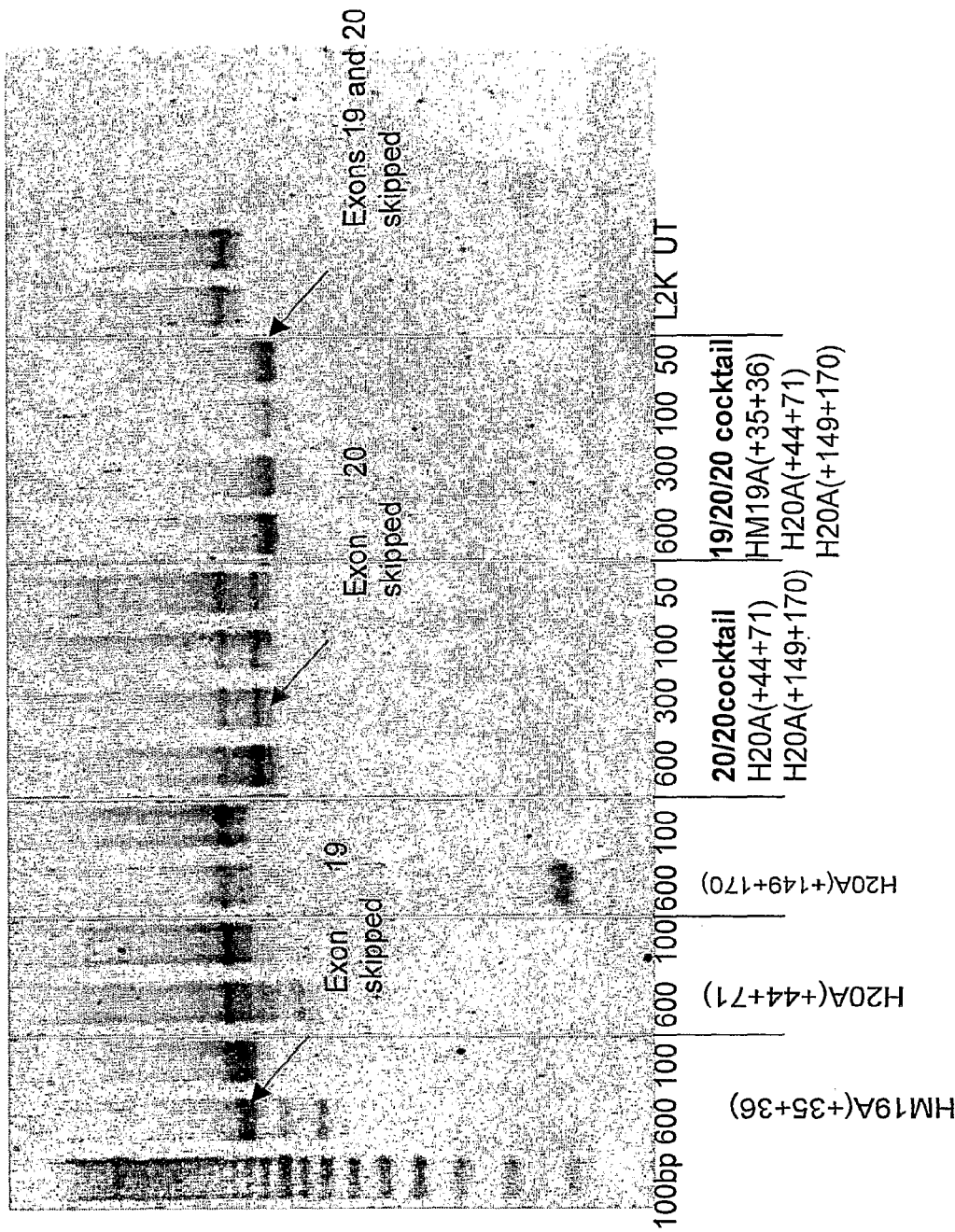
FIG. 10 Gel electrophoresis showing human exon 19/20 skipping using antisense molecules H20A(+44+71) and H20A(+149+170) directed at an exon 20 and a "cocktail" of antisense oligonucleotides H19A(+35+65, H20A(+44+71) and H20A(+149+170) directed at exons 19/20.

FIG. 10 illustrates exon 19 and 20 skipping using a "cocktail" of antisense oligonucleotides, as tested using gel electrophoresis. It is interesting to note that it was not easy to induce exon 20 skipping using single antisense oligonucleotides H20A(+44+71) [SEQ ID NO:81] or H20A(+149+170)

[SEQ ID NO:82], as illustrated in sections 2 and 3 of the gel shown in FIG. 10. Whereas, a "cocktail" of antisense oligonucleotides was more efficient as can be seen in section 4 of FIG. 10 using a "cocktail" of antisense oligonucleotides H20A(+44+71) and H20A(+149+170). When the cocktail was used to target exon 19, skipping was even stronger (see section 5, FIG. 10).

Figure 11:
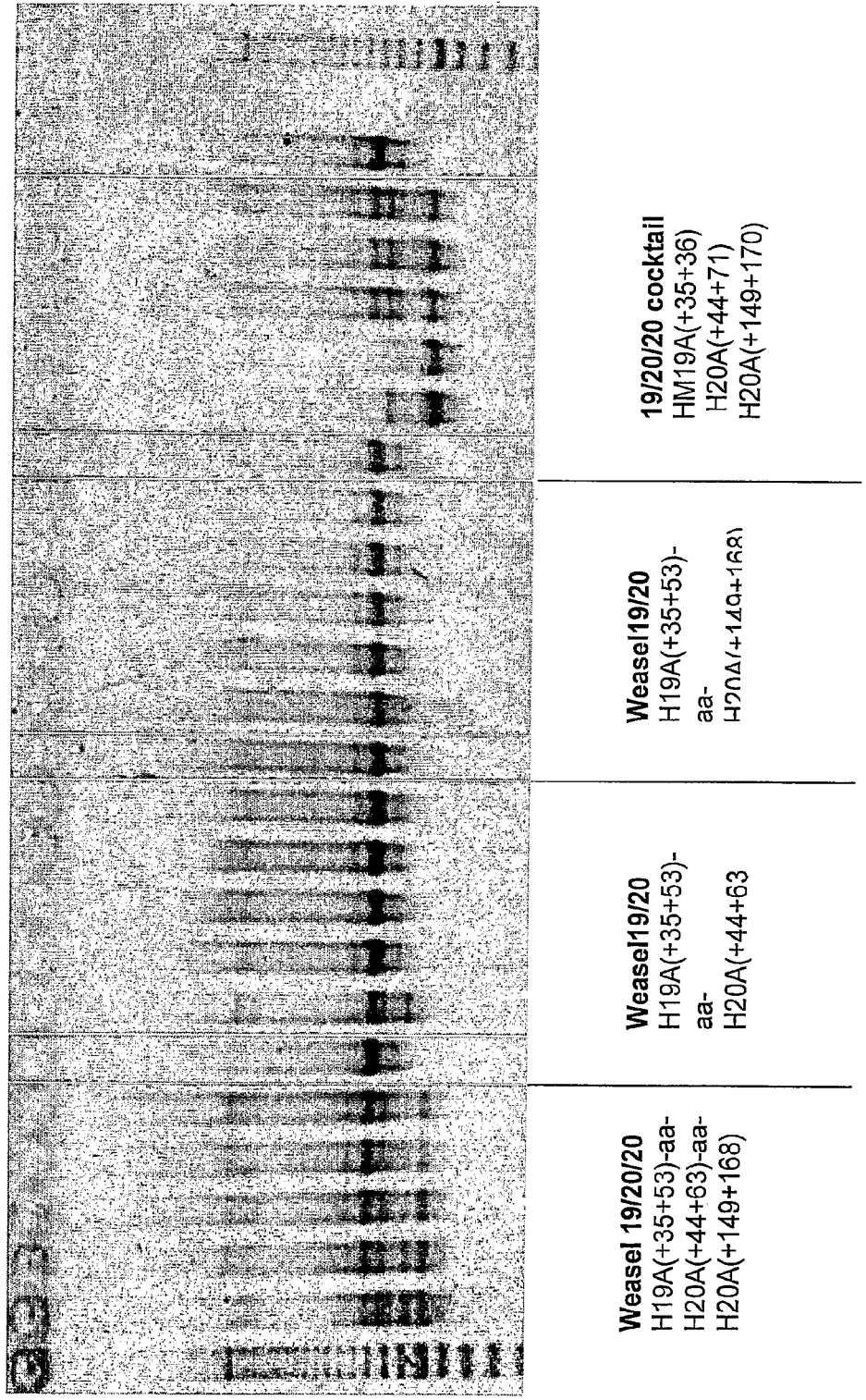
FIG. 11 Gel electrophoresis showing human exon 19/20 skipping using "weasels" directed at exons 19 and 20.

FIG. 11 illustrates gel electrophoresis results of exon 19/20 skipping using "weasels" The "weasels" were effective in skipping exons 19 and 20 at concentrations of 25, 50, 100, 300 and 600 nM. A further "weasel" sequence is shown in the last row of Table 3C. This compound should give good results.

Antisense Oligonucleotides Directed at Exon 20

Antisense oligonucleotides directed at exon 20 were prepared and tested for their ability to induce exon skipping in human muscle cells using similar methods as described above.

None of the antisense oligonucleotides tested induced exon 20 skipping when delivered into cells at a concentration of 10, 25, 50, 300 or 600 nM (see Table 15). Antisense molecules H20A(−11+17) [SEQ ID NO:86] and H20D(+08−20) [SEQ ID NO:87] are yet to be tested.

However, a combination or "cocktail" of H20A(+44+71) [SEQ ID NO: 81] and H20(+149+170) [SEQ ID NO:82] in a ratio of 1:1, exhibited very strong exon skipping at a concentration of 100 nM and 600 nM. Further, a combination of antisense molecules H19A(+35+65) [SEQ ID NO:79], H20A (+44+71) [SEQ ID NO:81] and H20A(+149+170) [SEQ ID NO:82] in a ratio of 2:1:1, induced very strong exon skipping at a concentration ranging from 10 nM to 600 nM.

TABLE 15

| Antisense Oligo-nucloetide name | Sequence | Ability to induce skipping |
|---|---|---|
| H20A(+44+71) | CUG GCA GAA UUC GAU CCA CCG GCU GUU C | No skipping |
| H20A(+149+170) | CAG CAG UAG UUG UCA UCU GCU C | No skipping |
| H20A(+185+203) | UGA UGG GGU GGU GGG UUG G | No skipping |
| H20A(−08+17) | AUC UGC AUU AAC ACC CUC UAG AAA G | No skipping |
| H20A(+30+53) | CCG GCU GUU CAG UUG UUC UGA GGC | No skipping |
| H20A(−11+17) | AUC UGC AUU AAC ACC CUC UAG AAA GAA A | Not tested yet |
| H20D(+08−20) | GAA GGA GAA GAG AUU CUU ACC UUA CAA A | Not tested yet |
| H20A(+44+71) & H20A(+149+170) | CUG GCA GAA UUC GAU CCA CCG GCU GUU C CAG CAG UAG UUG UCA UCU GCU C | Very strong skipping |
| H19A(+44+71) : H20A(+44+71) ; H20A(+149+170) | GCC UGA GCU GAU CUG CUG GCA UCU UGC AGU U CUG GCA GAA UUC GAU CCA CCG GCU GUU C CAG CAG UAG UUG UCA UCU GCU C | Very strong skipping |

Antisense Oligonucleotides Directed at Exon 21

Antisense oligonucleotides directed at exon 21 were prepared and tested for their ability to induce exon skipping in human muscle cells using similar methods as described above.

H21A(+85+108) [SEQ ID NO:92] and H21A(+85+106) [SEQ ID NO:91] induced exon 21 skipping when delivered into cells at a concentration of 50 nM. Table 16 below includes other antisense molecules tested at a concentration range of 5, 25, 50, 100, 200 and 300 nM. These antisense molecules showed a variable ability to induce exon skipping

TABLE 16

| Antisense Oligonucleotide name | Sequence | Ability to induce skipping |
|---|---|---|
| H21A(−06+16) | GCC GGU UGA CUU CAU CCU GUG C | Skips at 600 nM |
| H21A(+85+106) | CUG CAU CCA GGA ACA UGG GUC C | Skips at 50 nM |
| H21A(+85+108) | GUC UGC AUC CAG GAA CAU GGG UC | Skips at 50 nM |
| H21A(+08+31) | GUU GAA GAU CUG AUA GCC GGU UGA | Skips faintly to |
| H21D(+18−07) | UAC UUA CUG UCU GUA GCU CUU UCU | No skipping |

Antisense Oligonucleotides Directed at Exon 22

Antisense oligonucleotides directed at exon 22 were prepared and tested for their ability to induce exon skipping in human muscle cells using similar methods as described above.

Figure 12:
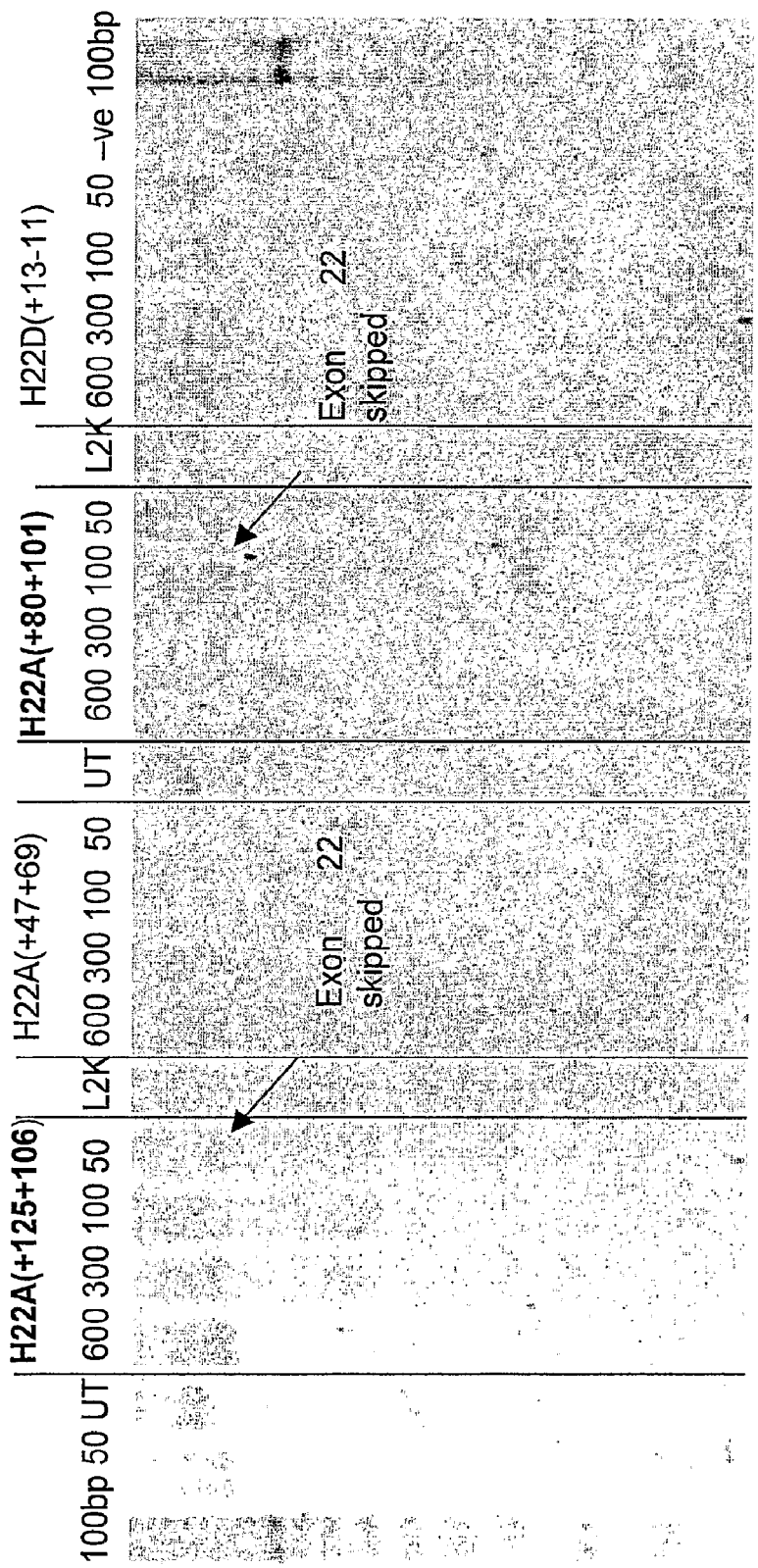
FIG. 12 Gel electrophoresis showing exon 22 skipping using antisense molecules H22A(+125+106), H22A(+47+69), H22A(+80+101) and H22D(+13−11) directed at exon 22.

FIG. 12 illustrates differing efficiencies of two antisense molecules directed at exon 22 acceptor splice site. H22A(+125+106) [SEQ ID NO:96] and H22A(+80+101) [SEQ ID NO: 98] induce strong exon 22 skipping from 50 nM to 600 nM concentration.

H22A(+125+146) [SEQ ID NO:96] and H22A(+80+101) [SEQ ID NO:98] induced exon 22 skipping when delivered into cells at a concentration of 50 nM. Table 17 below shows other antisense molecules tested at a concentration range of 50, 100, 300 and 600 nM. These antisense molecules showed a variable ability to induce exon skipping.

TABLE 17

| Antisense oligonucleotide name | Sequence | Ability to induce skipping |
|---|---|---|
| H22A(+22+45) | CAC UCA UGG UCU CCU GAU AGC GCA | No skipping |
| H22A(+125+146) | CUG CAA UUC CCC GAG UCU CUG C | Skipping to 50 nM |
| H22A(+47+69) | ACU GCU GGA CCC AUG UCC UGA UG | Skipping to 300 nM |
| H22A(+80+101) | CUA AGU UGA GGU AUG GAG AGU | Skipping to 50 nM |
| H22D(+13−11) | UAU UCA CAG ACC UGC AAU UCC CC | No skipping |

Antisense Oligonucleotides Directed at Exon 23

Antisense oligonucleotides directed at exon 23 were prepared and tested for their ability to induce exon skipping in human muscle cells using similar methods as described above.

Table 18 below shows antisense molecules tested at a concentration range of 25, 50, 100, 300 and 600 nM. These antisense molecules showed no ability to induce exon skipping or are yet to be tested.

TABLE 18

| Antisense oligonucleotide name | Sequence | Ability to induce skipping |
|---|---|---|
| H23A(+34+59) | ACA GUG GUG CUG AGA UAG UAU AGG CC | No skipping |
| H23A(+18+39) | UAG GCC ACU UUG UUG CUC UUG C | No Skipping |
| H23A(+72+90) | UUC AGA GGG CGC UUU CUU C | No Skipping |

Antisense Oligonucleotides Directed at Exon 24

Antisense oligonucleotides directed at exon 24 were prepared using similar methods as described above. Table 19 below outlines the antisense oligonucleotides directed at exon 24 that are yet to be tested for their ability to induce exon 24 skipping.

TABLE 19

| Antisense oligonucleotide name | Sequence | Ability to induce skipping |
|---|---|---|
| H24A(+48+70) | GGG CAG GCC AUU CCU CCU UCA GA | Needs testing |
| H24A(-02+22) | UCU UCA GGG UUU GUA UGU GAU UCU | Needs testing |

Antisense Oligonucleotides Directed at Exon 25

Antisense oligonucleotides directed at exon 25 were prepared using similar methods as described above. Table 20 below shows the antisense oligonucleotides directed at exon 25 that are yet to be tested for their ability to induce exon 25 skipping.

TABLE 20

| Antisense oligonucleotide name | Sequence | Ability to induce skipping |
|---|---|---|
| H25A(+9+36) | CUG GGC UGA AUU GUC UGA AUA UCA CUG | Needs testing |
| H25A(+131+156) | CUG UUG GCA CAU GUG AUC CCA CUG AG | Needs testing |
| H25D(+16-08) | GUC UAU ACC UGU UGG CAC AUG UGA | Needs testing |

Antisense Oligonucleotides Directed at Exon 26

Antisense oligonucleotides directed at exon 26 were prepared using similar methods as described above. Table 21 below outlines the antisense oligonucleotides directed at exon 26 that are yet to be tested for their ability to induce exon 26 skipping.

TABLE 21

| Antisense oligonucleotide name | Sequence | Ability to induce skipping |
|---|---|---|
| H26A(+132+156) | UGC UUU CUG UAA UUC AUC UGG AGU U | Needs testing |
| H26A(-07+19) | CCU CCU UUC UGG CAU AGA CCU UCC AC | Needs testing |
| H26A(+68+92) | UGU GUC AUC CAU UCG UGC AUC UCU G | Faint skipping at 600 nM |

Antisense Oligonucleotides Directed at Exon 27

Antisense oligonucleotides directed at exon 27 were prepared using similar methods as described above. Table 22 below outlines the antisense oligonucleotides directed at exon 27 that are yet to be tested for their ability to induce exon 27 skipping.

TABLE 22

| Antisense oligonucleotide name | Sequence | Ability to induce skipping |
|---|---|---|
| H27A(+82+106) | UUA AGG CCU CUU GUG CUA CAG GUG G | Needs testing |
| H27A(-4+19) | GGG CCU CUU CUU UAG CUC UCU GA | Faint skipping at 600 and 300 nM |
| H27D(+19-03) | GAC UUC CAA AGU CUU GCA UUU C | v. strong skipping at 600 and 300 nM |

Antisense Oligonucleotides Directed at Exon 28

Antisense oligonucleotides directed at exon 28 were prepared using similar methods as described above. Table 23 below outlines the antisense oligonucleotides directed at exon 28 that are yet to be tested for their ability to induce exon 28 skipping.

TABLE 23

| Antisense oligonucleotide name | Sequence | Ability to induce skipping |
|---|---|---|
| H28A(-05+19) | GCC AAC AUG CCC AAA CUU CCU AAG | v. strong skipping at 600 and 300 nM |
| H28A(+99+124) | CAG AGA UUU CCU CAG CUC CGC CAG GA | Needs testing |
| H28D(+16-05) | CUU ACA UCU AGC ACC UCA GAG | v. strong skipping at 600 and 300 nM |

Antisense Oligonucleotides Directed at Exon 29

Antisense oligonucleotides directed at exon 29 were prepared using similar methods as described above. Table 24 below outlines the antisense oligonucleotides directed at exon 29 that are yet to be tested for their ability to induce exon 29 skipping.

TABLE 24

| Antisense oligonucleotide name | Sequence | Ability to induce skipping |
|---|---|---|
| H29A(+57+81) | UCC GCC AUC UGU UAG GGU CUG UGC C | Needs testing |
| H29A(+18+42) | AUU UGG GUU AUC CUC UGA AUG UCG C | v. strong skipping at 600 and 300 nM |
| H29D(+17-05) | CAU ACC UCU UCA UGU AGU UCC C | v. strong skipping at 600 and 300 nM |

Antisense Oligonucleotides Directed at Exon 30

Antisense oligonucleotides directed at exon 30 were prepared using similar methods as described above. Table 25 below outlines the antisense oligonucleotides directed at exon 30 that are yet to be tested for their ability to induce exon 30 skipping.

TABLE 25

| Antisense oligonucleotide name | Sequence | Ability to induce skipping |
|---|---|---|
| H30A(+122+147) | CAU UUG AGC UGC GUC CAC CUU GUC UG | Needs testing |
| H30A(+25+50) | UCC UGG GCA GAC UGG AUG CUC UGU UC | Very strong skipping at 600 and 300 nM. |
| H30D(+19-04) | UUG CCU GGG CUU CCU GAG GCA UU | Very strong skipping at 600 and 300 nM. |

Antisense Oligonucleotides Directed at Exon 31

Antisense oligonucleotides directed at exon 31 were prepared and tested for their ability to induce exon skipping in human muscle cells using similar methods as described above.

Figure 13:
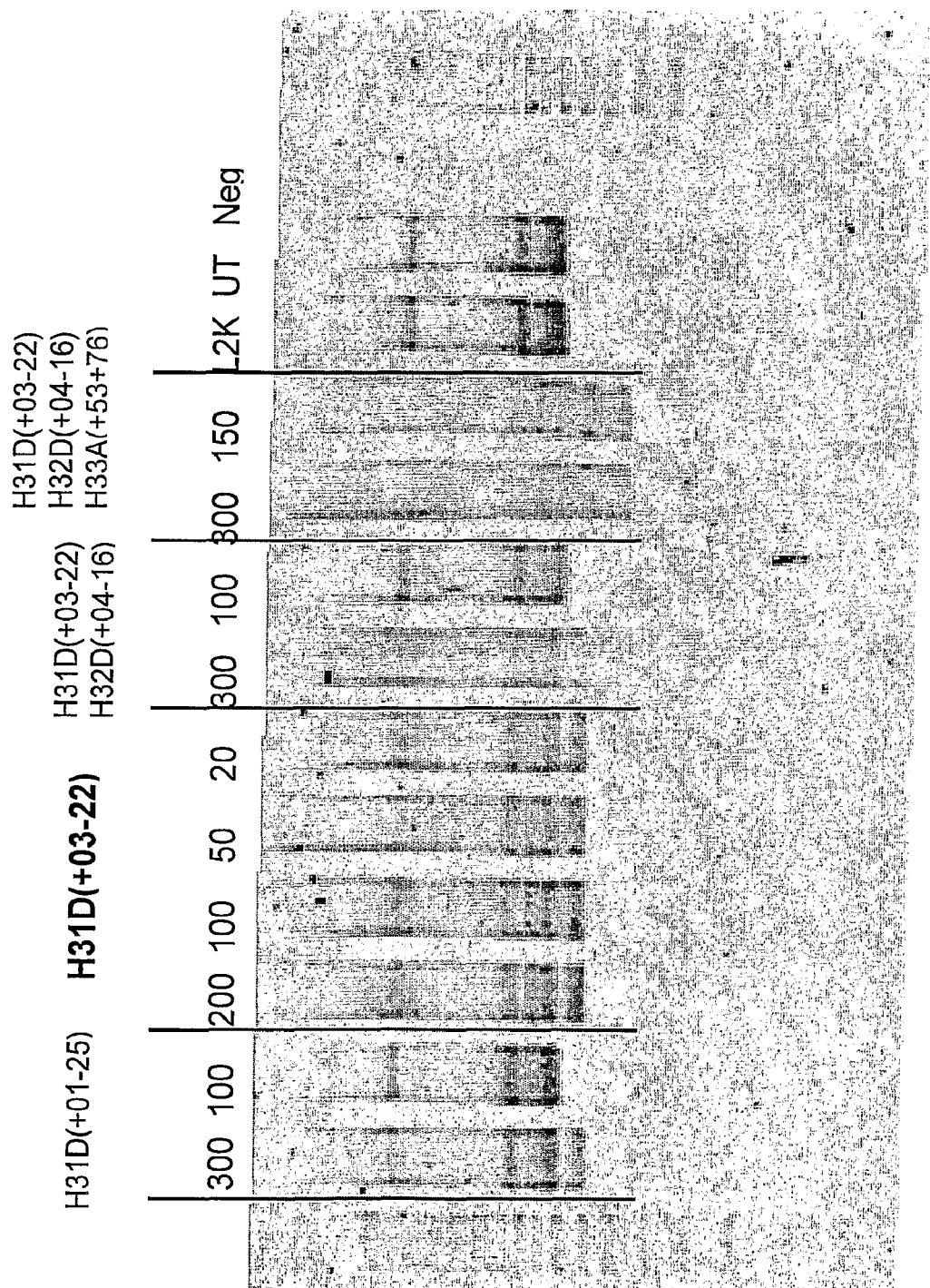
FIG. 13 Gel electrophoresis showing exon 31 skipping using antisense molecules H31D(+01−25) and H31D(+03−22); and a "cocktail" of antisense molecules directed at exon 31.

FIG. 13 illustrates differing efficiencies of two antisense molecules directed at exon 31 acceptor splice site and a "cocktail" of exon 31 antisense oligonucleotides at varying concentrations. H31 D(+03-22) [SEQ ID NO:124] substantially induced exon 31 skipping when delivered into cells at a concentration of 20 nM. Table 26 below also includes other antisense molecules tested at a concentration of 100 and 300 nM. These antisense molecules showed a variable ability to induce exon skipping.

TABLE 26

| Antisense oligonucleotide name | Sequence | Ability to induce skipping |
|---|---|---|
| H31D(+06-18) | UUC UGA AAU AAC AUA UAC CUG UGC | Skipping to 300 nM |
| H31D(+03-22) | UAG UUU CUG AAA UAA CAU AUA CCU G | Skipping to 20 nM |

TABLE 26-continued

| Antisense oligonucleotide name | Sequence | Ability to induce skipping |
|---|---|---|
| H31A(+05+25) | GAC UUG UCA AAU CAG AUU GGA | No skipping |
| H31D(+04-20) | GUU UCU GAA AUA ACA UAU ACC UGU | Skipping to 300 nM |

Antisense Oligonucleotides Directed at Exon 32

Antisense oligonucleotides directed at exon 32 were prepared and tested for their ability to induce exon skipping in human muscle cells using similar methods as described above.

H32D(+04–16) [SEQ ID NO:127] and H32A(+49+73) [SEQ ID NO:130] induced exon 32 skipping when delivered into cells at a concentration of 300 nM. Table 27 below also shows other antisense molecules tested at a concentration of 100 and 300 nM. These antisense molecules did not show an ability to induce exon skipping.

TABLE 27

| Antisense oligonucleotide name | Sequence | Ability to induce skipping |
|---|---|---|
| H32D(+04-16) | CAC CAG AAA UAC AUA CCA CA | Skipping to 300 nM |
| H32A(+151+170) | CAA UGA UUU AGC UGU GAC UG | No skipping |
| H32A(+10+32) | CGA AAC UUC AUG GAG ACA UCU UG | No skipping |
| H32A(+49+73) | CUU GUA GAC GCU GCU CAA AAU UGG C | Skipping to 300 nM |

Antisense Oligonucleotides Directed at Exon 33

Antisense oligonucleotides directed at exon 33 were prepared and tested for their ability to induce exon skipping in human muscle cells using similar methods as described above.

Figure 14:
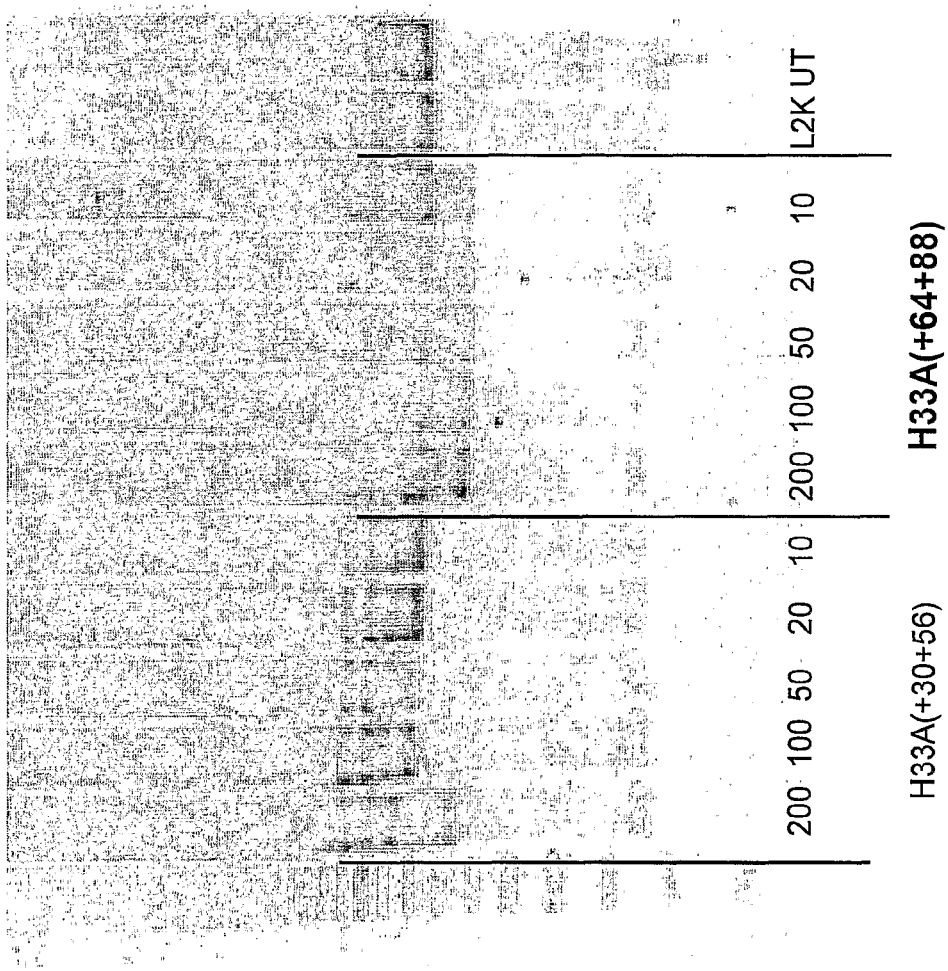
FIG. 14 Gel electrophoresis showing exon 33 skipping using antisense molecules H33A(+30+56) and H33A(+64+88) directed at exon 33.

FIG. 14 shows differing efficiencies of two antisense molecules directed at exon 33 acceptor splice site. H33A(+64+88) [SEQ ID NO:134] substantially induced exon 33 skipping when delivered into cells at a concentration of 10 nM. Table 28 below includes other antisense molecules tested at a concentration of 100, 200 and 300 nM. These antisense molecules showed a variable ability to induce exon skipping.

TABLE 28

| Antisense oligonucleotide name | Sequence | Ability to induce skipping |
|---|---|---|
| H33D(+09-11) | CAU GCA CAC ACC UUU GCU CC | No skipping |
| H33A(+53+76) | UCU GUA CAA UCU GAC GUC CAG UCU | Skipping to 200 nM |
| H33A(+30+56) | GUC UUU AUC ACC AUU UCC ACU UCA GAC | Skipping to 200 nM |
| H33A(+64+88) | CCG UCU GCU UUU UCU GUA CAA UCU G | Skipping to 10 nM |

Antisense Oligonucleotides Directed at Exon 34

Antisense oligonucleotides directed at exon 34 were prepared and tested for their ability to induce exon skipping in human muscle cells using similar methods as described above.

Table 29 below includes antisense molecules tested at a concentration of 100 and 300 nM. These antisense molecules showed a variable ability to induce exon skipping.

TABLE 29

| Antisense oligonucleotide name | Sequence | Ability to induce skipping |
|---|---|---|
| H34A(+83+104) | UCC AUA UCU GUA GCU GCC AGC C | No skipping |
| H34A(+143+165) | CCA GGC AAC UUC AGA AUC CAA AU | No skipping |
| H34A(−20+10) | UUU CUG UUA CCU GAA AAG AAU UAU AAU GAA | Not tested |
| H34A(+46+70) | CAU UCA UUU CCU UUC GCA UCU UAC G | Skipping to 300 nM |
| H34A(+95+120) | UGA UCU CUU UGU CAA UUC CAU AUC UG | Skipping to 300 nM |
| H34D(+10−20) | UUC AGU GAU AUA GGU UUU ACC UUU CCC CAG | Not tested |
| H34A(+72+96) | CUG UAG CUG CCA GCC AUU CUG UCA AG | No skipping |

Antisense Oligonucleotides Directed at Exon 35

Antisense oligonucleotides directed at exon 35 were prepared and tested for their ability to induce exon skipping in human muscle cells using similar methods as described above.

Figure 15:
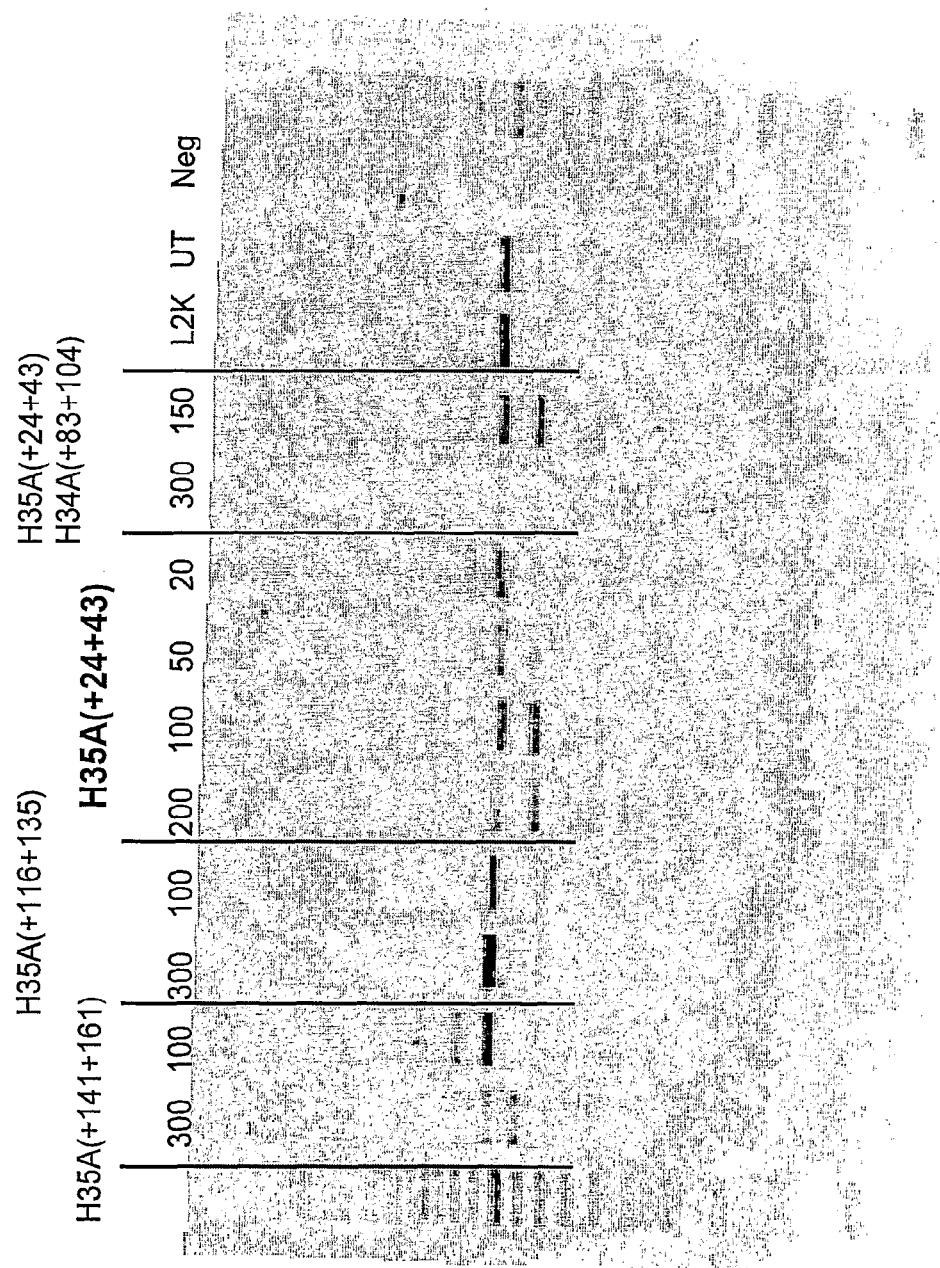
FIG. 15 Gel electrophoresis showing exon 35 skipping using antisense molecules H35A(+141+161), H35A(+116+135), and H35A(+24+43) and a "cocktail" of two antisense molecules, directed at exon 35.

FIG. 15 shows differing efficiencies of antisense molecules directed at exon 35 acceptor splice site. H35A(+24+43) [SEQ ID NO:144] substantially induced exon 35 skipping when delivered into cells at a concentration of 20 nM. Table 30 below also includes other antisense molecules tested at a concentration of 100 and 300 nM. These antisense molecules showed no ability to induce exon skipping.

TABLE 30

| Antisense oligonucleotide name | Sequence | Ability to induce skipping |
|---|---|---|
| H35A(+141+161) | UCU UCU GCU CGG GAG GUG ACA | Skipping to 20 nM |
| H35A(+116+135) | CCA GUU ACU AUU CAG AAG AC | No skipping |
| H35A(+24+43) | UCU UCA GGU GCA CCU UCU GU | No skipping |

Antisense Oligonucleotides Directed at Exon 36

Antisense oligonucleotides directed at exon 36 were prepared and tested for their ability to induce exon skipping in human muscle cells using similar methods as described above.

Figure 16:
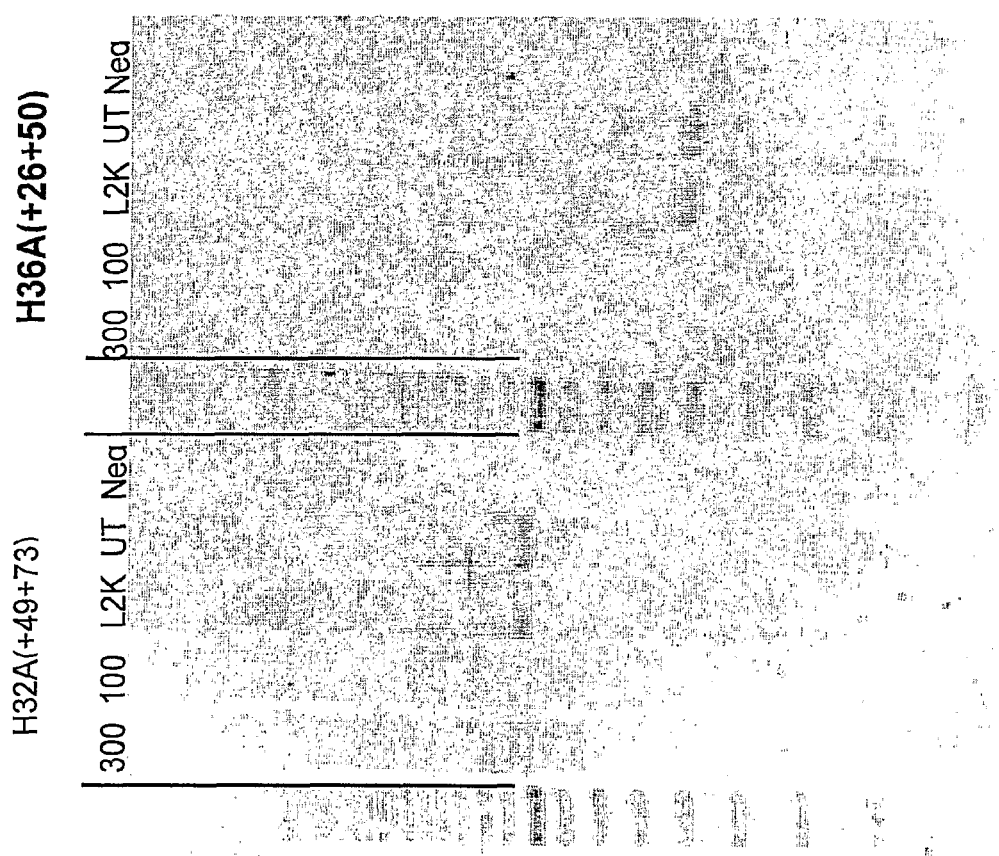
FIG. 16 Gel electrophoresis showing exon 36 skipping using antisense molecules H32A(+49+73) and H36A(+26+50) directed at exon 36.

Antisense molecule H36A(+26+50) [SEQ ID NO:145] induced exon 36 skipping when delivered into cells at a concentration of 300 nM, as shown in FIG. 16.

Antisense Oligonucleotides Directed at Exon 37

Antisense oligonucleotides directed at exon 37 were prepared and tested for their ability to induce exon skipping in human muscle cells using similar methods as described above.

Figure 17:
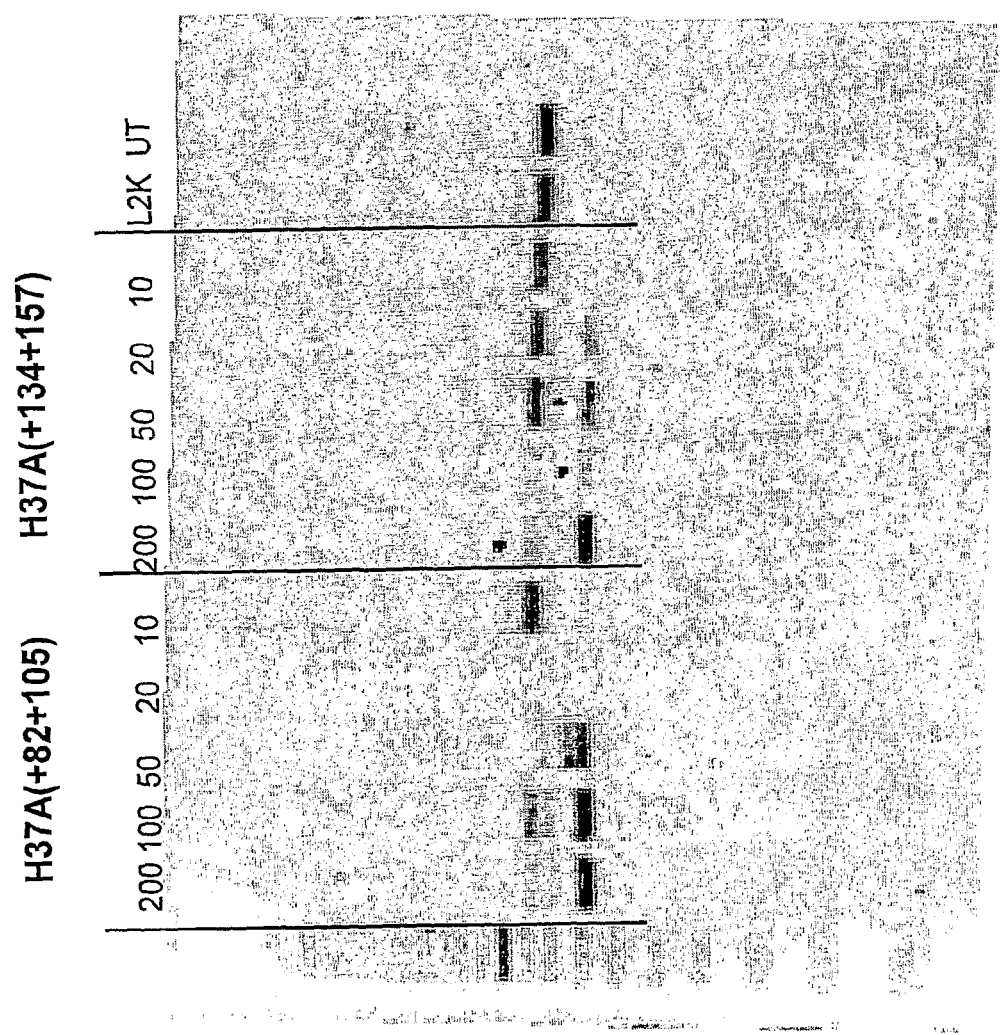
FIG. 17 Gel electrophoresis showing exon 37 skipping using antisense molecules H37A(+82+105) and H37A(+134+157) directed at exon 37.

FIG. 17 shows differing efficiencies of two antisense molecules directed at exon 37 acceptor splice site. H37A(+82+105) [SEQ ID NO:148] and H37A(+134+157) [SEQ ID NO:149] substantially induced exon 37 skipping when delivered into cells at a concentration of 10 nM. Table 31 below shows the antisense molecules tested.

TABLE 31

| Antisense oligonucleotide name | Sequence | Ability to induce skipping |
|---|---|---|
| H37A(+26+50) | CGU GUA GAG UCC ACC UUU GGG CGU A | No skipping |
| H37A(+82+105) | UAC UAA UUU CCU GCA GUG GUC ACC | Skipping to 10 nM |
| H37A(+134+157) | UUC UGU GUG AAA UGG CUG CAA AUC | Skipping to 10 nM |

Antisense Oligonucleotides Directed at Exon 38

Antisense oligonucleotides directed at exon 38 were prepared and tested for their ability to induce exon skipping in human muscle cells using similar methods as described above.

Figure 18:
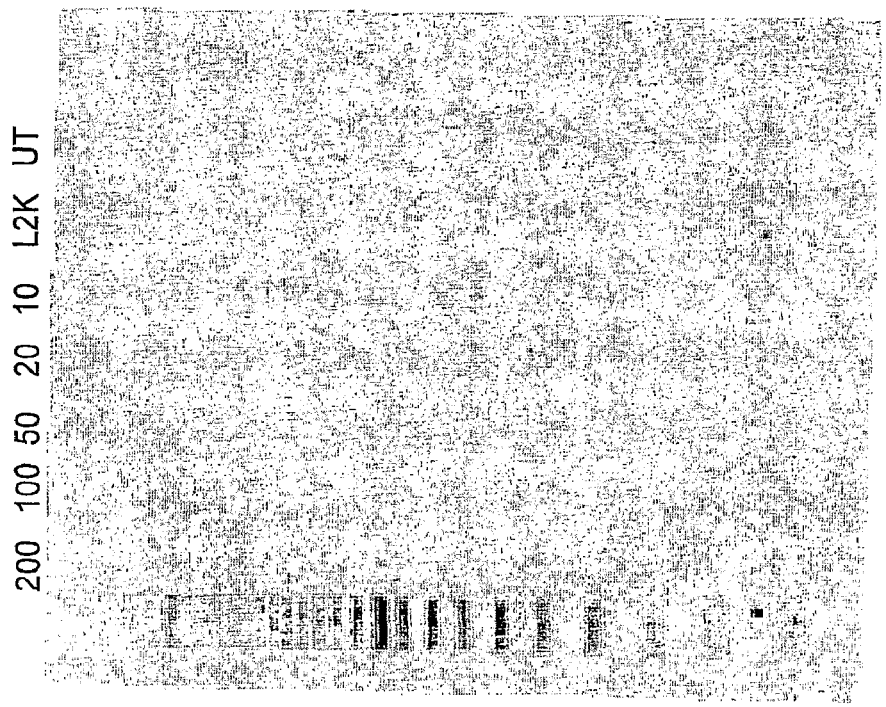
FIG. 18 Gel electrophoresis showing exon 38 skipping using antisense molecule H38A(+88+112) directed at exon 38.

FIG. 18 illustrates antisense molecule H38A(+88+112) [SEQ ID NO:152], directed at exon 38 acceptor splice site. H38A(+88+112) substantially induced exon 38 skipping when delivered into cells at a concentration of 10 nM. Table 32 below shows the antisense molecules tested and their ability to induce exon skipping.

TABLE 32

| Antisense oligonucleotide name | Sequence | Ability to induce skipping |
|---|---|---|
| H38A(−01+19) | CCU UCA AAG GAA UGG AGG CC | No skipping |
| H38A(+59+83) | UGC UGA AUU UCA GCC UCC AGU GGU U | Skipping to 10 nM |
| H38A(+88+112) | UGA AGU CUU CCU CUU UCA GAU UCA C | Skipping to 10 nM |

Antisense Oligonucleotides Directed at Exon 39

Antisense oligonucleotides directed at exon 39 were prepared and tested for their ability to induce exon skipping in human muscle cells using similar methods as described above.

H39A(+62+85) [SEQ ID NO:153] induced exon 39 skipping when delivered into cells at a concentration of 100 nM. Table 33 below shows the antisense molecules tested and their ability to induce exon skipping.

TABLE 33

| Antisense oligonucleotide name | Sequence | Ability to induce skipping |
|---|---|---|
| H39A(+62+85) | CUG GCU UUC UCU CAU CUG UGA UUC | Skipping to 100 nM |

TABLE 33-continued

| Antisense oligonucleotide name | Sequence | Ability to induce skipping |
|---|---|---|
| H39A(+39+58) | GUU GUA AGU UGU CUC CUC UU | No skipping |
| H39A(+102+121) | UUG UCU GUA ACA GCU GCU GU | No skipping |
| H39D(+10-10) | GCU CUA AUA CCU UGA GAG CA | Skipping to 300 nM |

Antisense Oligonucleotides Directed at Exon 40

Antisense oligonucleotides directed at exon 40 were prepared and tested for their ability to induce exon skipping in human muscle cells using similar methods as described above.

Figure 19:
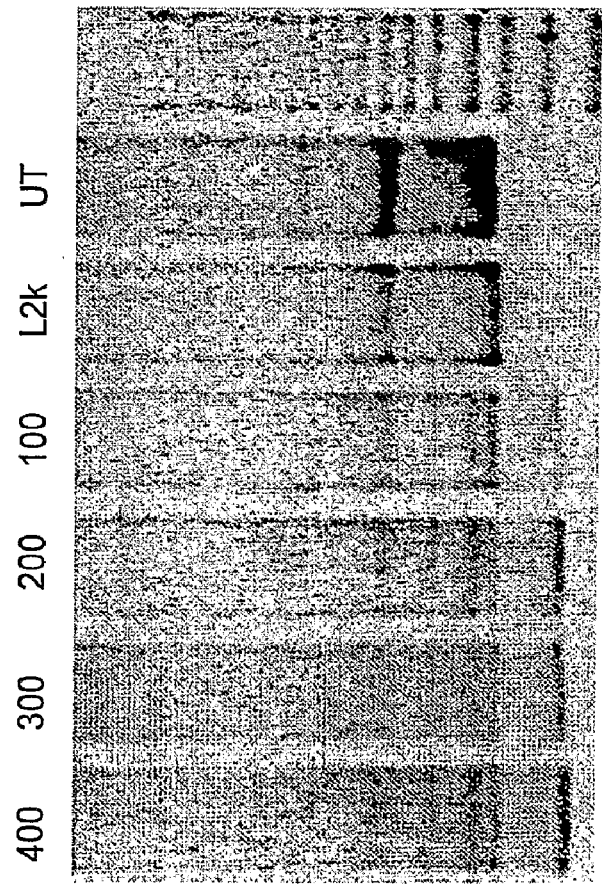
FIG. 19 Gel electrophoresis showing exon 40 skipping using antisense molecule H40A(−05+17) directed at exon 40.

FIG. 19 illustrates antisense molecule H40A(-05+17) [SEQ ID NO:157] directed at exon 40 acceptor splice site. H40A(-05+17) and H40A(+129+153) [SEQ ID NO:158] both substantially induced exon 40 skipping when delivered into cells at a concentration of 5 nM.

Antisense Oligonucleotides Directed at Exon 42

Antisense oligonucleotides directed at exon 42 were prepared and tested for their ability to induce exon skipping in human muscle cells using similar methods as described above.

Figure 20:
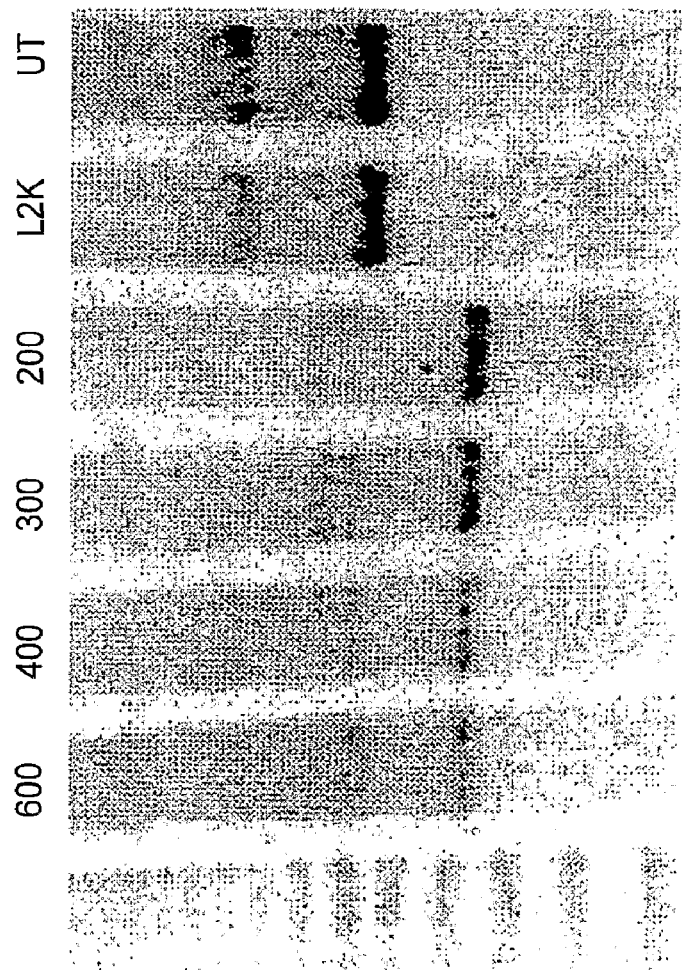
FIG. 20 Gel electrophoresis showing exon 42 skipping using antisense molecule H42A(−04+23) directed at exon 42.

FIG. 20 illustrates antisense molecule H42A(-04+23) [SEQ ID NO:159], directed at exon 42 acceptor splice site. H42A(-4+23) and H42D(+19-02) [SEQ ID NO:161] both induced exon 42 skipping when delivered into cells at a concentration of 5 nM. Table 34 below shows the antisense molecules tested and their ability to induce exon 42 skipping.

TABLE 34

| Antisense oligonucleotide name | Sequence | Ability to induce skipping |
|---|---|---|
| H42A(-4+23) | AUC GUU UCU UCA CGG ACA GUG UGC UGG | Skipping to 5 nM |
| H42A(+86+109) | GGG CUU GUG AGA CAU GAG UGA UUU | Skipping to 100 nM |
| H42D(+19-02) | A CCU UCA GAG GAC UCC UCU UGC | Skipping to 5 nM |

Antisense Oligonucleotides Directed at Exon 43

Antisense oligonucleotides directed at exon 43 were prepared and tested for their ability to induce exon skipping in human muscle cells using similar methods as described above.

H43A(+101+120) [SEQ ID NO:163] induced exon 43 skipping when delivered into cells at a concentration of 25 nM. Table 35 below includes the antisense molecules tested and their ability to induce exon 43 skipping.

TABLE 35

| Antisense oligonucleotide name | Sequence | Ability to induce skipping |
|---|---|---|
| H43D(+10-15) | UAU GUG UUA CCU ACC CUU GUC GGU C | Skipping to 100 nM |

TABLE 35-continued

| Antisense oligonucleotide name | Sequence | Ability to induce skipping |
|---|---|---|
| H43A(+101+120) | GGA GAG AGC UUC CUG UAG CU | Skipping to 25 nM |
| H43A(+78+100) | UCA CCC UUU CCA CAG GCG UUG CA | Skipping to 200 nM |

Antisense Oligonucleotides Directed at Exon 44

Antisense oligonucleotides directed at exon 44 were prepared using similar methods as described above. Testing for the ability of these antisense molecules to induce exon 44 skipping is still in progress. The antisense molecules under review are shown as SEQ ID Nos: 165 to 167 in Table 1A.

Antisense Oligonucleotides Directed at Exon 45

Antisense oligonucleotides directed at exon 45 were prepared using similar methods as described above. Testing for the ability of these antisense molecules to induce exon 45 skipping is still in progress. The antisense molecules under review are shown as SEQ ID Nos: 207 to 211 in Table 1A.

Antisense Oligonucleotides Directed at Exon 46

Antisense oligonucleotides directed at exon 46 were prepared and tested for their ability to induce exon skipping in human muscle cells using similar methods as described above.

Figure 21:
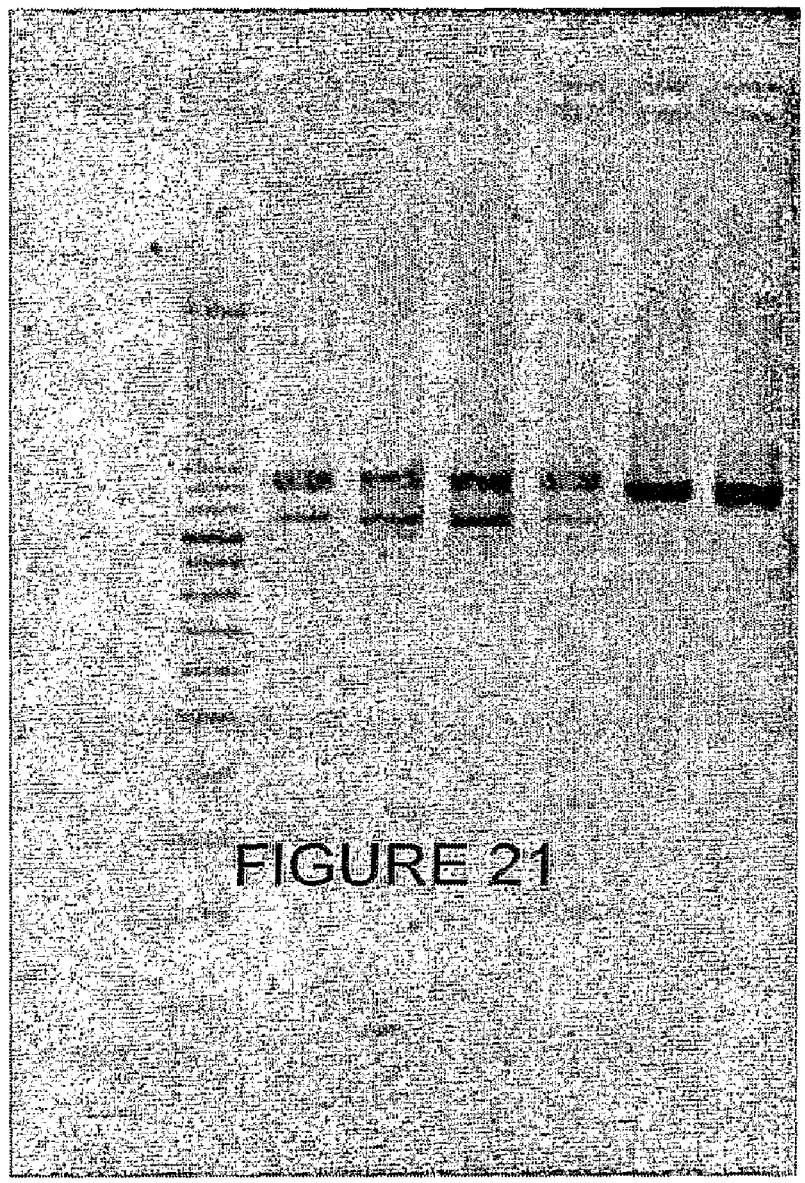
FIG. 21 Gel electrophoresis showing exon 46 skipping using antisense molecule H46A(+86+115) directed at exon 46

FIG. 21 illustrates the efficiency of one antisense molecule directed at exon 46 acceptor splice site. Antisense oligonucleotide H46A(+86+115) [SEQ ID NO:203] showed very strong ability to induce exon 46 skipping. Table 36 below includes antisense molecules tested. These antisense molecules showed varying ability to induce exon 46 skipping.

TABLE 36

| Antisense oligonucleotide name | Sequence | Ability to induce skipping |
|---|---|---|
| H46D(+16-04) | UUA CCU UGA CUU GCU CAA GC | No skipping |
| H46A(+90+109) | UCC AGG UUC AAG UGG GAU AC | No skipping |
| H46A(+86+115) | CUC UUU UCC AGG UUC AAG UGG GAU ACU AGC | Good skipping to 100 nM |
| H46A(+107+137) | CAA GCU UUU CUU UUA GUU GCU GCU CUU UUC C | Good skipping to 100 nM |
| H46A(-10+20) | UAU UCU UUU GUU CUU CUA GCC UGG AGA AAG | Weak skipping |
| H46A(+50+77) | CUG CUU CCU CCA ACC AUA AAA CAA AUU C | Weak skipping |

Antisense Oligonucleotides Directed at Exon 47

Antisense oligonucleotides directed at exon 47 were prepared and tested for their ability to induce exon skipping in human muscle cells using similar methods as described above.

H47A(+76+100) [SEQ ID NO:170] and H47A(-09+12) [SEQ ID NO:172] both induced exon 47 skipping when delivered into cells at a concentration of 200 nM. H47D(+25-02) [SEQ ID NO: 171] is yet to be prepared and tested.

Antisense Oligonucleotides Directed at Exon 50

Antisense oligonucleotides directed at exon 50 were prepared and tested for their ability to induce exon skipping in human muscle cells using similar methods as described above.

Antisense oligonucleotide molecule H50(+02+30) [SEQ ID NO: 173] was a strong inducer of exon skipping. Further, H50A(+07+33) [SEQ ID NO:174] and H50D(+07−18) [SEQ ID NO:175] both induced exon 50 skipping when delivered into cells at a concentration of 100 nM.

Antisense Oligonucleotides Directed at Exon 51

Antisense oligonucleotides directed at exon 51 were prepared and tested for their ability to induce exon skipping in human muscle cells using similar methods as described above.

Figure 22:
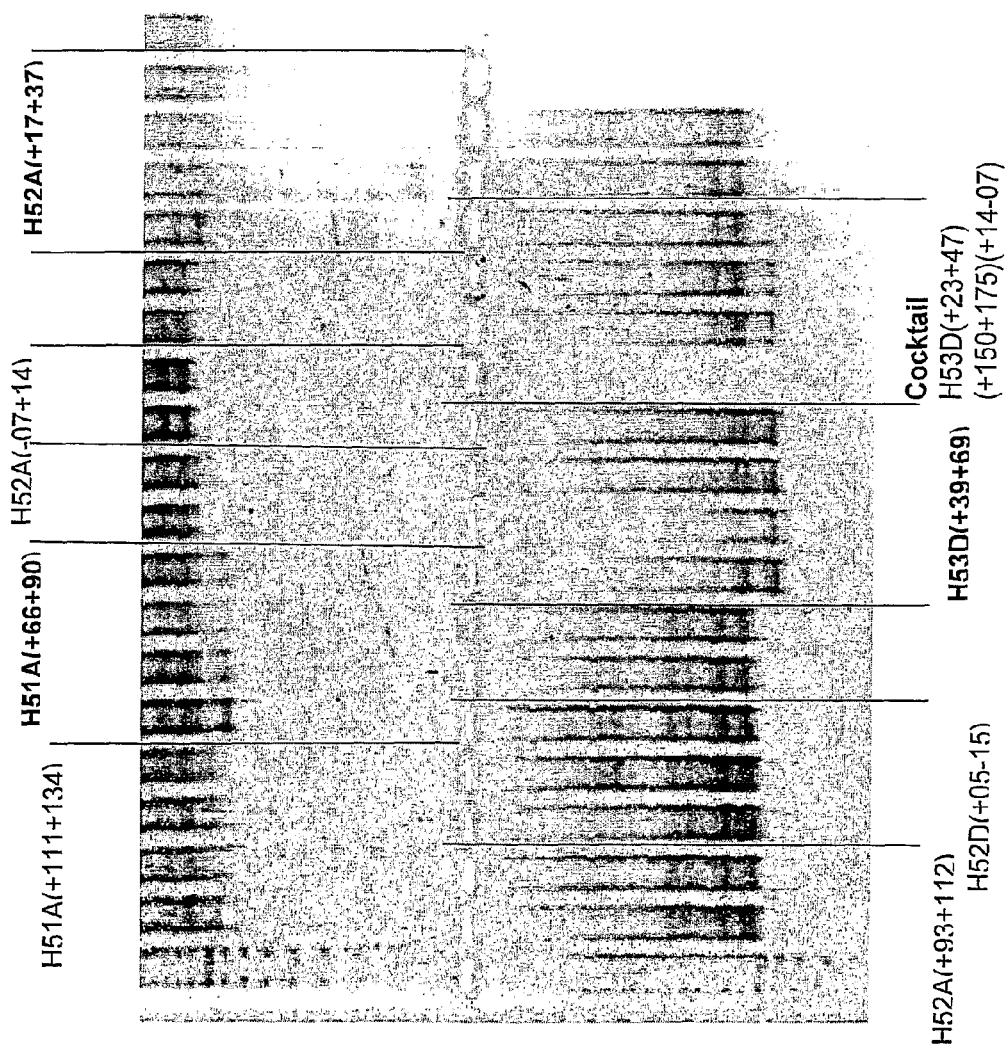
FIG. 22 Gel electrophoresis showing exon 51, exon 52 and exon 53 skipping using various antisense molecules directed at exons 51, 52 and 53, respectively. A "cocktail" of antisense molecules is also shown directed at exon 53.

FIG. 22 illustrates differing efficiencies of two antisense molecules directed at exon 51 acceptor splice site. Antisense oligonucleotide H51A(+66+90) [SEQ ID NO: 180] showed the stronger ability to induce exon 51 skipping. Table 37 below includes antisense molecules tested at a concentration range of 25, 50, 100, 300 and 600 nM. These antisense molecules showed varying ability to induce exon 51 skipping. The strongest inducers of exon skipping were antisense oligonucleotide H51A(+61+90) [SEQ ID NO: 179] and H51A (+66+95) [SEQ ID NO:181].

TABLE 37

| Antisense oligonucleotide name | Sequence | Ability to induce skipping |
| --- | --- | --- |
| H51A(−01+25) | ACC AGA GUA ACA GUC UGA GUA GGA GC | Faint skipping |
| H51D(+16−07) | CUC AUA CCU UCU GCU UGA UGA UC | Skipping at 300 nM |
| H51A(+111+134) | UUC UGU CCA AGC CCG GUU GAA AUC | Needs re-testing |
| H51A(+61+90) | ACA UCA AGG AAG AUG GCA UUU CUA GUU UGG | Very strong skipping |
| H51A(+66+90) | ACA UCA AGG AAG AUG GCA UUU CUA G | skipping |
| H51A(+66+95) | CUC CAA CAU CAA GGA AGA UGG CAU UUC UAG | Very strong skipping |
| H51D(+08−17) | AUC AUU UUU UCU CAU ACC UUC UGC U | No skipping |
| H51A/D(+08−17) & (−15+?) | AUC AUU UUU UCU CAU ACC UUC UGC UAG GAG CUA AAA | No skipping |
| H51A(+175+195) | CAC CCA CCA UCA CCC UCY GUG | No skipping |
| H51A(+199+220) | AUC AUC UCG UUG AUA UCC UCA A | No skipping |

Antisense Oligonucleotides Directed at Exon 52

Antisense oligonucleotides directed at exon 52 were prepared and tested for their ability to induce exon skipping in human muscle cells using similar methods as described above.

FIG. 22 also shows differing efficiencies of four antisense molecules directed at exon 52 acceptor splice site. The most effective antisense oligonucleotide for inducing exon 52 skipping was H52A(+17+37) [SEQ ID NO:188].

Table 38 below shows antisense molecules tested at a concentration range of 50, 100, 300 and 600 nM. These antisense molecules showed varying ability to induce exon 50 skipping. Antisense molecules H52A(+12+41) [SEQ ID NO:187] and H52A(+17+37) [SEQ ID NO:188] showed the strongest exon 50 skipping at a concentration of 50 nM.

TABLE 38

| Antisense oligonucleotide name | Sequence | Ability to induce skipping |
| --- | --- | --- |
| H52A(−07+14) | UCC UGC AUU GUU GCC UGU AAG | No skipping |
| H52A(+12+41) | UCC AAC UGG GGA CGC CUC UGU UCC AAA UCC | Very strong skipping |
| H52A(+17+37) | ACU GGG GAC GCC UCU GUU CCA | Skipping to 50 nM |
| H52A(+93+112) | CCG UAA UGA UUG UUC UAG CC | No skipping |
| H52D(+05−15) | UGU UAA AAA ACU UAC UUC GA | No skipping |

Antisense Oligonucleotides Directed at Exon 53

Antisense oligonucleotides directed at exon 53 were prepared and tested for their ability to induce exon skipping in human muscle cells using similar methods as described above.

FIG. 22 also shows antisense molecule H53A(+39+69) [SEQ ID NO:193] directed at exon 53 acceptor splice site. This antisense oligonucleotide was able to induce exon 53 skipping at 5, 100, 300 and 600 nM. A "cocktail" of three exon 53 antisense oligonucleotides:—H53D(+23+47) [SEQ ID NO:195], H53A(+150+175) [SEQ ID NO:196] and H53A (+14−07) [SEQ ID NO:194], were also tested, as shown in FIG. 20 and exhibited an ability to induce exon skipping.

Table 39 below includes other antisense molecules tested at a concentration range of 50, 100, 300 and 600 nM. These antisense molecules showed varying ability to induce exon 53 skipping. Antisense molecule H53A(+39+69) [SEQ ID NO:193] induced the strongest exon 53 skipping.

TABLE 39

| Antisense oligonucleotide name | Sequence | Ability to induce skipping |
| --- | --- | --- |
| H53A(+45+69) | CAU UCA ACU GUU GCC UCC GGU UCU G | Faint skipping at 50 nM |
| H53A(+39+62) | CUG UUG CCU CCG GUU CUG AAG GUG | Faint skipping at 50 nM |
| H53A(+39+69) | CAU UCA ACU GUU GCC UCC GGU UCU GAA GGU G | Strong skipping to 50 nM |
| H53D(+14−07) | UAC UAA CCU UGG UUU CUG UGA | Very faint skipping to 50 nM |
| H53A(+23+47) | CUG AAG GUG UUC UUG UAC UUC AUC C | Very faint skipping to 50 nM |
| H53A(+150+176) | UGU AUA GGG ACC CUC CUU CCA UGA CUC | Very faint skipping to 50 nM |

TABLE 39-continued

| Antisense oligonucleotide name | Sequence | Ability to induce skipping |
|---|---|---|
| H53D(+20-05) | CUA ACC UUG GUU UCU GUG AUU UUC U | Not made yet |
| H53D(+09-18) | GGU AUC UUU GAU ACU AAC CUU GGU UUC | Faint at 600 nM |
| H53A(-12+10) | AUU CUU UCA ACU AGA AUA AAA G | No skipping |
| H53A(-07+18) | GAU UCU GAA UUC UUU CAA CUA GAA U | No skipping |
| H53A(+07+26) | AUC CCA CUG AUU CUG AAU UC | No skipping |
| H53A(+124+145) | UUG GCU CUG GCC UGU CCU AAG A | No skipping |

The invention claimed is:

1. An isolated antisense oligonucleotide of 25 to 50 nucleotides in length comprising SEQ ID NO: 180, wherein the uracil bases are optionally thymine bases.

2. The antisense oligonucleotide of claim 1, wherein the antisense oligonucleotide comprises a non-natural backbone.

3. The antisense oligonucleotide of claim 1, wherein the antisense oligonucleotide is chemically linked to one or more moieties or conjugates that enhance the activity, cellular distribution, or cellular uptake of the antisense oligonucleotide.

4. The antisense oligonucleotide of claim 1, wherein the antisense oligonucleotide does not activate RNase H.

5. The antisense oligonucleotide of claim 2, wherein the sugar moieties of the oligonucleotide backbone are replaced with non-natural moieties.

6. The antisense oligonucleotide of claim 5, wherein the non-natural moieties are morpholinos.

7. The antisense oligonucleotide of claim 6, wherein the uracil bases are thymine bases.

8. The antisense oligonucleotide of claim 1, wherein the inter-nucleotide linkages of the oligonucleotide backbone are replaced with non-natural inter-nucleotide linkages.

9. The antisense oligonucleotide of claim 8, wherein the non-natural inter-nucleotide linkages are modified phosphates.

10. The antisense oligonucleotide of claim 9, wherein the modified phosphates are methyl phosphonates, methyl phosphorothioates, phosphoromorpholidates, phosphoropiperazidates or phosphoroamidates.

11. The antisense oligonucleotide of claim 10, wherein the modified phosphates are phosphoroamidates.

12. The antisense oligonucleotide of claim 10, wherein the modified phosphates are phosphoromorpholidates.

13. The antisense oligonucleotide of claim 1, wherein the sugar moieties of the oligonucleotide backbone are replaced with non-natural moieties and the inter-nucleotide linkages of the oligonucleotide backbone are replaced with non-natural inter-nucleotide linkages.

14. The antisense oligonucleotide of claim 13, wherein the non-natural moieties are morpholinos and the non-natural internucleotide linkages are modified phosphates.

15. The antisense oligonucleotide of claim 14, wherein the modified phosphates are methyl phosphonates, methyl phosphorothioates, phosphoromorpholidates, phosphoropiperazidates or phosphoroamidates.

16. The antisense oligonucleotide of claim 15, wherein the modified phosphates are phosphoroamidates.

17. The antisense oligonucleotide of claim 15, wherein the modified phosphates are phosphoromorpholidates.

18. The antisense oligonucleotide of claim 15, wherein the uracil bases are thymine bases.

19. The antisense oligonucleotide of claim 18, wherein the antisense oligonucleotide is chemically linked to one or more moieties or conjugates that enhance the activity, cellular distribution, or cellular uptake of the antisense oligonucleotide.

20. The antisense oligonucleotide of claim 1, wherein the antisense oligonucleotide is 25 nucleotides in length.

21. The antisense oligonucleotide of claim 20, wherein the uracil bases are thymine bases.

22. A pharmaceutical composition, comprising the antisense oligonucleotide of claim 1 and a pharmaceutically acceptable carrier.

23. The pharmaceutical composition of claim 22, wherein the pharmaceutically acceptable carrier is phosphate-buffered saline.

24. A pharmaceutically acceptable salt of the antisense oligonucleotide of claim 1.

* * * * *

SEQUENCE LISTING

<160> NUMBER OF SEQ ID NOS: 214

<210> SEQ ID NO 1
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 1
gauagguggu aucaacaucu guaa                                        24

<210> SEQ ID NO 2
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 2
gauagguggu aucaacaucu g                                           21

<210> SEQ ID NO 3
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 3
gauagguggu aucaacaucu guaag                                       25

<210> SEQ ID NO 4
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 4
ggugguauca acaucuguaa                                             20

<210> SEQ ID NO 5
<211> LENGTH: 20
<212> TYPE: DNA
<213> ORGANISM: Artificial Sequence

```
<220> FEATURE:
<223> OTHER INFORMATION: Human 2'-O-methyl phosphorothioate antisense
      oligonucleotide

<400> SEQUENCE: 5
guaucaacau cuguaagcac                                                    20

<210> SEQ ID NO 6
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 6
ugcauguucc agucguugug ugg                                                23

<210> SEQ ID NO 7
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 7
cacuauucca gucaaauagg ucugg                                              25

<210> SEQ ID NO 8
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 8
auuuaccaac cuucaggauc gagua                                              25

<210> SEQ ID NO 9
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 9
ggccuaaaac acauacacau a                                                  21

<210> SEQ ID NO 10
<211> LENGTH: 20
<212> TYPE: DNA
<213> ORGANISM: Artificial Sequence
<220> FEATURE:
<223> OTHER INFORMATION: Canine 2'-O-methyl phosphorothioate antisense
      oligonucleotide

<400> SEQUENCE: 10 cauuuugac cuacaugugg                                                     20

<210> SEQ ID NO 11
<211> LENGTH: 20
<212> TYPE: DNA
<213> ORGANISM: Artificial Sequence
<220> FEATURE:
<223> OTHER INFORMATION: Canine 2'-O-methyl phosphorothioate antisense
```

-continued

```
                                    oligonucleotide

<400> SEQUENCE: 11
uuugaccuac auguggaaag                                                    20

<210> SEQ ID NO 12
<211> LENGTH: 26
<212> TYPE: DNA
<213> ORGANISM: Artificial Sequence
<220> FEATURE:
<223> OTHER INFORMATION: Canine 2'-O-methyl phosphorothioate antisense
      oligonucleotide

<400> SEQUENCE: 12
uacauuuuug accuacaugu ggaaag                                             26

<210> SEQ ID NO 13
<211> LENGTH: 22
<212> TYPE: DNA
<213> ORGANISM: Artificial Sequence
<220> FEATURE:
<223> OTHER INFORMATION: Canine 2'-O-methyl phosphorothioate antisense
      oligonucleotide

<400> SEQUENCE: 13
auuuuugacc uacaugggaa ag                                                 22

<210> SEQ ID NO 14
<211> LENGTH: 23
<212> TYPE: DNA
<213> ORGANISM: Artificial Sequence
<220> FEATURE:
<223> OTHER INFORMATION: Canine 2'-O-methyl phosphorothioate antisense
      oligonucleotide

<400> SEQUENCE: 14
uacgaguuga uugucggacc cag                                                23

<210> SEQ ID NO 15
<211> LENGTH: 25
<212> TYPE: DNA
<213> ORGANISM: Artificial Sequence
<220> FEATURE:
<223> OTHER INFORMATION: Canine 2'-O-methyl phosphorothioate antisense
      oligonucleotide

<400> SEQUENCE: 15
guggucuccu uaccuaugac ugugg                                              25

<210> SEQ ID NO 16
<211> LENGTH: 17
<212> TYPE: DNA
<213> ORGANISM: Artificial Sequence
<220> FEATURE:
<223> OTHER INFORMATION: Canine 2'-O-methyl phosphorothioate antisense
      oligonucleotide

<400> SEQUENCE: 16
ggucuccuua ccuauga                                                       17

<210> SEQ ID NO 17
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide
```

```
-continued

<400> SEQUENCE: 17
ugucucagua aucuucuuac cuau                                              24

<210> SEQ ID NO 18
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 18
ucuuaccuau gacuauggau gaga                                              24

<210> SEQ ID NO 19
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 19
gcaugaacuc uuguggaucc                                                   20

<210> SEQ ID NO 20
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 20
ccaggguacu acuuacauua                                                   20

<210> SEQ ID NO 21
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 21
aucguguguc acagcaucca g                                                 21

<210> SEQ ID NO 22
<211> LENGTH: 30
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 22
uguucagggc augaacucuu guggauccuu                                        30

<210> SEQ ID NO 23
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 23
```
uaggaggcgc ucccauccu guagucacu g                    31

```
<210> SEQ ID NO 24
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 24
```
aggucuagga ggcgccuccc auccuguagg u                  31

```
<210> SEQ ID NO 25
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 25
```
gcgccuccca uccuguaggu cacug                         25

```
<210> SEQ ID NO 26
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 26
```
cuucgaggag gucuaggagg cgccuc                        26

```
<210> SEQ ID NO 27
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 27
```
cucccauccu guaggucacu g                             21

```
<210> SEQ ID NO 28
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 28
```
uaccaguuuu ugcccuguca gg                            22

```
<210> SEQ ID NO 29
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 29
```
ucaauaugcu gcuucccaaa cugaaa                        26

```
<210> SEQ ID NO 30
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 30
cuaggaggcg ccucccaucc uguag                                           25

<210> SEQ ID NO 31
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 31
uuaugauuuc caucuacgau gucaguacuu c                                    31

<210> SEQ ID NO 32
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 32
cuuaccugcc aguggaggau uauauuccaa a                                    31

<210> SEQ ID NO 33
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 33
caucaggauu cuuaccugcc agugg                                           25

<210> SEQ ID NO 34
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 34
cgaugucagu acuuccaaua uucac                                           25

<210> SEQ ID NO 35
<211> LENGTH: 18
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 35
accauucauc aggauucu                                                   18

<210> SEQ ID NO 36
```

-continued

```
<211> LENGTH: 18
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 36
accugccagu ggaggauu                                                   18

<210> SEQ ID NO 37
<211> LENGTH: 27
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 37
ccaauauuca cuaaaucaac cuguuaa                                         27

<210> SEQ ID NO 38
<211> LENGTH: 30
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 38
caggauucuu accugccagu ggaggauuau                                      30

<210> SEQ ID NO 39
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 39
acgaugucag uacuuccaau auucacuaaa u                                    31

<210> SEQ ID NO 40
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 40
auuuccaucu acgaugucag uacuuccaau a                                    31

<210> SEQ ID NO 41
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 41
caggagcuuc caaaugcugc a                                               21

<210> SEQ ID NO 42
<211> LENGTH: 29
<212> TYPE: DNA
```

```
<213> ORGANISM: Artificial Sequence
<220> FEATURE:
<223> OTHER INFORMATION: Human 2'-O-methyl phosphorothioate antisense
      oligonucleotide

<400> SEQUENCE: 42
cuugucuuca ggagcuucca aaugcugca                                       29

<210> SEQ ID NO 43
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 43
uccucagcag aaagaagcca cg                                              22

<210> SEQ ID NO 44
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 44
uuagaaaucu cuccuugugc                                                 20

<210> SEQ ID NO 45
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 45
uaaauugggu guuacacaau                                                 20

<210> SEQ ID NO 46
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 46
cccugaggca uucccaucuu gaau                                            24

<210> SEQ ID NO 47
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 47
aggacuuacu ugcuuuguuu                                                 20

<210> SEQ ID NO 48
<211> LENGTH: 23
<212> TYPE: DNA
<213> ORGANISM: Artificial Sequence
<220> FEATURE:
```

```
<223> OTHER INFORMATION: Human 2'-O-methyl phosphorothioate antisense
      oligonucleotide

<400> SEQUENCE: 48
cuugaauuua ggagauucau cug                                            23

<210> SEQ ID NO 49
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 49
caucuucuga uaauuuccu guu                                             23

<210> SEQ ID NO 50
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 50
ucuucuguuu uuguuagcca guca                                           24

<210> SEQ ID NO 51
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 51
ucuauguaaa cugaaaauuu                                                20

<210> SEQ ID NO 52
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 52
uucuggagau ccauuaaaac                                                20

<210> SEQ ID NO 53
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 53
cagcaguugc gugaucucca cuag                                           24

<210> SEQ ID NO 54
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide
```

```
<400> SEQUENCE: 54
uucaucaacu accaccacca u                                              21

<210> SEQ ID NO 55
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 55
cuaagcaaaa uaaucugacc uuaag                                          25

<210> SEQ ID NO 56
<211> LENGTH: 28
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 56
cuuguaaaag aacccagcgg ucuucugu                                       28

<210> SEQ ID NO 57
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 57
caucuacaga uguuugccca uc                                             22

<210> SEQ ID NO 58
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 58
gaaggauguc uuguaaaaga acc                                            23

<210> SEQ ID NO 59
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 59
accuguucuu caguaagacg                                                20

<210> SEQ ID NO 60
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 60
```

```
caugacacac cuguucuuca guaa                                          24
```

<210> SEQ ID NO 61
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 61

```
cauuugagaa ggaugucuug                                               20
```

<210> SEQ ID NO 62
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 62

```
aucucccaau accuggagaa gaga                                          24
```

<210> SEQ ID NO 63
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 63

```
gccaugcacu aaaaggcac ugcaagacau u                                   31
```

<210> SEQ ID NO 64
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 64

```
ucuuuaaagc caguugugug aauc                                          24
```

<210> SEQ ID NO 65
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 65

```
uuucugaaag ccaugcacua a                                             21
```

<210> SEQ ID NO 66
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 66

```
guacauacgg ccaguuuuug aagac                                         25
```

```
<210> SEQ ID NO 67
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 67
cuagauccgc uuuuaaaacc uguuaaaaca a                                      31

<210> SEQ ID NO 68
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 68
ucuuuucuag auccgcuuuu aaaaccuguu a                                      31

<210> SEQ ID NO 69
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 69
cuagauccgc uuuuaaaacc uguua                                             25

<210> SEQ ID NO 70
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 70
ccgucuucug ggucacugac uua                                               23

<210> SEQ ID NO 71
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 71
cuagauccgc uuuuaaaacc uguuaa                                            26

<210> SEQ ID NO 72
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 72
ccgcuuuuaa aaccuguuaa                                                   20
```

```
<210> SEQ ID NO 73
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 73
uggauugcuu uuucuuuucu agaucc                                          26

<210> SEQ ID NO 74
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 74
caugcuuccg ucuucugggu cacug                                           25

<210> SEQ ID NO 75
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 75
gaucuuguuu gagugaauac agu                                             23

<210> SEQ ID NO 76
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 76
guuauccagc caugcuuccg uc                                              22

<210> SEQ ID NO 77
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 77
ugauaauugg uaucacuaac cugug                                           25

<210> SEQ ID NO 78
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 78
guaucacuaa ccugugcugu ac                                              22

<210> SEQ ID NO 79
<211> LENGTH: 20
```

-continued

```
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 79
cagcaguagu ugucaucugc                                              20

<210> SEQ ID NO 80
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 80
gccugagcug aucugcuggc aucuugcagu u                                 31

<210> SEQ ID NO 81
<211> LENGTH: 28
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 81
cuggcagaau ucgauccacc ggcuguuc                                     28

<210> SEQ ID NO 82
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 82
cagcaguagu ugucaucugc uc                                           22

<210> SEQ ID NO 83
<211> LENGTH: 19
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 83 ugaugggug gugggguugg                                               19

<210> SEQ ID NO 84
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 84
aucugcauua acacccucua gaaag                                        25

<210> SEQ ID NO 85
<211> LENGTH: 24
<212> TYPE: DNA
<213> ORGANISM: Artificial Sequence
```

```
<220> FEATURE:
<223> OTHER INFORMATION: Human 2'-O-methyl phosphorothioate antisense
      oligonucleotide

<400> SEQUENCE: 85
ccggcuguuc aguuguucug aggc                                              24

<210> SEQ ID NO 86
<211> LENGTH: 28
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 86
aucugcauua acacccucua gaaagaaa                                          28

<210> SEQ ID NO 87
<211> LENGTH: 28
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 87
gaaggagaag agauucuuac cuuacaaa                                          28

<210> SEQ ID NO 88
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 88
auucgaucca ccggcuguuc                                                   20

<210> SEQ ID NO 89
<211> LENGTH: 19
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 89
cugcuggcau cuugcaguu                                                    19

<210> SEQ ID NO 90
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 90
gccgguugac uucauccugu gc                                                22

<210> SEQ ID NO 91
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
```

```
                                    oligonucleotide

<400> SEQUENCE: 91
cugcauccag gaacaugggu cc                                                  22

<210> SEQ ID NO 92
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 92
gucugcaucc aggaacaugg guc                                                 23

<210> SEQ ID NO 93
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 93
guugaagauc ugauagccgg uuga                                                24

<210> SEQ ID NO 94
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 94
uacuuacugu cuguagcucu uucu                                                24

<210> SEQ ID NO 95
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 95
cacucauggu cuccugauag cgca                                                24

<210> SEQ ID NO 96
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 96
cugcaauucc ccgagucucu gc                                                  22

<210> SEQ ID NO 97
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide
```

-continued

```
<400> SEQUENCE: 97
acugcuggac ccauguccug aug                                      23

<210> SEQ ID NO 98
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 98
cuaaguugag guauggagag u                                        21

<210> SEQ ID NO 99
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 99
uauucacaga ccugcaauuc ccc                                      23

<210> SEQ ID NO 100
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 100
acaguggugc ugagauagua uaggcc                                   26

<210> SEQ ID NO 101
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 101
uaggccacuu uguugcucuu gc                                       22

<210> SEQ ID NO 102
<211> LENGTH: 19
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 102
uucagagggc gcuuucuuc                                           19

<210> SEQ ID NO 103
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 103
```

-continued gggcaggcca uuccuccuuc aga                          23

<210> SEQ ID NO 104
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 104
ucuucagggu uuguauguga uucu                          24

<210> SEQ ID NO 105
<211> LENGTH: 27
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 105
cugggcugaa uugucugaau aucacug                       27

<210> SEQ ID NO 106
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 106
cuguuggcac augugauccc acugag                        26

<210> SEQ ID NO 107
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 107
gucuauaccu guuggcacau guga                          24

<210> SEQ ID NO 108
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 108
ugcuuucugu aauucaucug gaguu                         25

<210> SEQ ID NO 109
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 109
ccuccuuucu ggcauagacc uuccac                        26

```
<210> SEQ ID NO 110
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 110
ugugucaucc auucgugcau cucug                                              25

<210> SEQ ID NO 111
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 111
uuaaggccuc uugugcuaca ggugg                                              25

<210> SEQ ID NO 112
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 112
gggccucuuc uuuagcucuc uga                                                23

<210> SEQ ID NO 113
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 113
gacuuccaaa gucuugcauu uc                                                 22

<210> SEQ ID NO 114
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 114
gccaacaugc ccaaacuucc uaag                                               24

<210> SEQ ID NO 115
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 115
cagagauuuc cucagcuccg ccagga                                             26

<210> SEQ ID NO 116
```

```
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 116
cuuacaucua gcaccucaga g                                                21

<210> SEQ ID NO 117
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 117
uccgccaucu guuaggucu gugcc                                             25

<210> SEQ ID NO 118
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 118
auuuggguua uccucugaau gucgc                                            25

<210> SEQ ID NO 119
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 119
cauaccucuu cauguaguuc uc                                               22

<210> SEQ ID NO 120
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 120
cauuugagcu gcguccaccu gucgucugu g                                      31

<210> SEQ ID NO 121
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 121
uccugggcag acuggaugcu cuguuc                                           26

<210> SEQ ID NO 122
<211> LENGTH: 23
<212> TYPE: DNA
```

```
<213> ORGANISM: Artificial Sequence
<220> FEATURE:
<223> OTHER INFORMATION: Human 2'-O-methyl phosphorothioate antisense
      oligonucleotide

<400> SEQUENCE: 122
uugccugggc uuccugaggc auu                                             23

<210> SEQ ID NO 123
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 123
uucugaaaua acauauaccu gugc                                            24

<210> SEQ ID NO 124
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 124
uaguuucuga aauaacauau accug                                           25

<210> SEQ ID NO 125
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 125
gacuugucaa aucagauugg a                                               21

<210> SEQ ID NO 126
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 126
guuucugaaa uaacauauac cugu                                            24

<210> SEQ ID NO 127
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 127
caccagaaau acauaccaca                                                 20

<210> SEQ ID NO 128
<211> LENGTH: 20
<212> TYPE: DNA
<213> ORGANISM: Artificial Sequence
<220> FEATURE:
```

<223> OTHER INFORMATION: Human 2'-O-methyl phosphorothioate antisense
      oligonucleotide

<400> SEQUENCE: 128
caaugauuua gcugugacug                                                     20

<210> SEQ ID NO 129
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 129
cgaaacuuca uggagacauc uug                                                 23

<210> SEQ ID NO 130
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 130
cuuguagacg cugcucaaaa uuggc                                               25

<210> SEQ ID NO 131
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 131
caugcacaca ccuuugcucc                                                     20

<210> SEQ ID NO 132
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 132
ucuguacaau cugacgucca gucu                                                24

<210> SEQ ID NO 133
<211> LENGTH: 27
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 133
gucuuuauca ccauuccac uucagac                                              27

<210> SEQ ID NO 134
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

```
<400> SEQUENCE: 134
ccgucugcuu uuucuguaca aucug                                       25

<210> SEQ ID NO 135
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 135
uccauaucug uagcugccag cc                                          22

<210> SEQ ID NO 136
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 136
ccaggcaacu ucagaaucca aau                                         23

<210> SEQ ID NO 137
<211> LENGTH: 30
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 137
uuucuguuac cugaaaagaa uuauaaugaa                                  30

<210> SEQ ID NO 138
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 138
cauucauuuc cuuucgcauc uuacg                                       25

<210> SEQ ID NO 139
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 139
ugaucucuuu gucaauucca uaucug                                      26

<210> SEQ ID NO 140
<211> LENGTH: 27
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 140
```

-continued

```
uucagugaua uagguuuuac cuuuccc                                27
```

<210> SEQ ID NO 141
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 141

```
cuguagcugc cagccauucu gucaag                                 26
```

<210> SEQ ID NO 142
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 142

```
ucuucugcuc gggaggugac a                                      21
```

<210> SEQ ID NO 143
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 143

```
ccaguuacua uucagaagac                                        20
```

<210> SEQ ID NO 144
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 144

```
ucuucaggug caccuucugu                                        20
```

<210> SEQ ID NO 145
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 145

```
ugugaugugg uccacauucu gguca                                  25
```

<210> SEQ ID NO 146
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 146

```
ccauguguuu cugguauucc                                        20
```

<210> SEQ ID NO 147
<211> LENGTH: 25
<212> TYPE: DNA
<213> ORGANISM: Artificial Sequence
<220> FEATURE:
<223> OTHER INFORMATION: Human 2'-O-methyl phosphorothioate antisense oligonucleotide

<400> SEQUENCE: 147
cguguagagu ccaccuuugg gcgua                                          25

<210> SEQ ID NO 148
<211> LENGTH: 24
<212> TYPE: DNA
<213> ORGANISM: Artificial Sequence
<220> FEATURE:
<223> OTHER INFORMATION: Human 2'-O-methyl phosphorothioate antisense oligonucleotide

<400> SEQUENCE: 148
uacuaauuuc cugcaguggu cacc                                           24

<210> SEQ ID NO 149
<211> LENGTH: 24
<212> TYPE: DNA
<213> ORGANISM: Artificial Sequence
<220> FEATURE:
<223> OTHER INFORMATION: Human 2'-O-methyl phosphorothioate antisense oligonucleotide

<400> SEQUENCE: 149
uucuguguga aauggcugca aauc                                           24

<210> SEQ ID NO 150
<211> LENGTH: 20
<212> TYPE: DNA
<213> ORGANISM: Artificial Sequence
<220> FEATURE:
<223> OTHER INFORMATION: Human 2'-O-methyl phosphorothioate antisense oligonucleotide

<400> SEQUENCE: 150
ccuucaaagg aauggaggcc                                                20

<210> SEQ ID NO 151
<211> LENGTH: 25
<212> TYPE: DNA
<213> ORGANISM: Artificial Sequence
<220> FEATURE:
<223> OTHER INFORMATION: Human 2'-O-methyl phosphorothioate antisense oligonucleotide

<400> SEQUENCE: 151
ugcugaauuu cagccuccag ugguu                                          25

<210> SEQ ID NO 152
<211> LENGTH: 25
<212> TYPE: DNA
<213> ORGANISM: Artificial Sequence
<220> FEATURE:
<223> OTHER INFORMATION: Human 2'-O-methyl phosphorothioate antisense oligonucleotide

<400> SEQUENCE: 152
ugaagucuuc cucuuucaga uucac                                          25

```
<210> SEQ ID NO 153
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 153
cuggcuuucu cucaucugug auuc                                          24

<210> SEQ ID NO 154
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 154
guuguaaguu gucccucuu                                                20

<210> SEQ ID NO 155
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 155
uugucuguaa cagcugcugu                                               20

<210> SEQ ID NO 156
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 156
gcucuaauac cuugagagca                                               20

<210> SEQ ID NO 157
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 157
cuuugagacc ucaaauccug uu                                            22

<210> SEQ ID NO 158
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 158
cuuuauuuuc cuuucaucuc ugggc                                         25

<210> SEQ ID NO 159
<211> LENGTH: 27
```

```
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 159
aucguuucuu cacggacagu gugcugg                                           27

<210> SEQ ID NO 160
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 160
gggcuuguga gacaugagug auuu                                              24

<210> SEQ ID NO 161
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 161
accuucagag gacuccucuu gc                                                22

<210> SEQ ID NO 162
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 162
uauguguuac cuacccuugu cgguc                                             25

<210> SEQ ID NO 163
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 163
ggagagagcu uccuguagcu                                                   20

<210> SEQ ID NO 164
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 164
ucacccuuuc cacaggcguu gca                                               23

<210> SEQ ID NO 165
<211> LENGTH: 20
<212> TYPE: DNA
<213> ORGANISM: Artificial Sequence
```

```
<220> FEATURE:
<223> OTHER INFORMATION: Human 2'-O-methyl phosphorothioate antisense
      oligonucleotide

<400> SEQUENCE: 165
uuugugucuu ucugagaaac                                              20

<210> SEQ ID NO 166
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 166
aaagacuuac cuuaagauac                                              20

<210> SEQ ID NO 167
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 167
aucugucaaa ucgccugcag                                              20

<210> SEQ ID NO 168
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 168
uuaccuugac uugcucaagc                                              20

<210> SEQ ID NO 169
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 169
uccagguuca agugggauac                                              20

<210> SEQ ID NO 170
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 170
gcucuucugg gcuuauggga gcacu                                        25

<210> SEQ ID NO 171
<211> LENGTH: 27
<212> TYPE: DNA
<213> ORGANISM: Artificial Sequence
<220> FEATURE:
<223> OTHER INFORMATION: Human 2'-O-methyl phosphorothioate antisense
```

-continued

```
      oligonucleotide

<400> SEQUENCE: 171
accuuuaucc acuggagauu ugucugc                                          27

<210> SEQ ID NO 172
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 172
uuccaccagu aacugaaaca g                                                21

<210> SEQ ID NO 173
<211> LENGTH: 29
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 173
ccacucagag cucagaucuu cuaacuucc                                        29

<210> SEQ ID NO 174
<211> LENGTH: 27
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 174
cuucaacuca gagcucagau cuucuaa                                          27

<210> SEQ ID NO 175
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 175
gggauccagu auacuuacag gcucc                                            25

<210> SEQ ID NO 176
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 176
accagaguaa cagucugagu aggagc                                           26

<210> SEQ ID NO 177
<211> LENGTH: 23
<212> TYPE: DNA
<213> ORGANISM: Artificial Sequence
<220> FEATURE:
<223> OTHER INFORMATION: Human 2'-O-methyl phosphorothioate antisense
      oligonucleotide
```

```
<400> SEQUENCE: 177
cucauaccuu cugcuugaug auc                                          23

<210> SEQ ID NO 178
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 178
uucuguccaa gcccgguuga aauc                                         24

<210> SEQ ID NO 179
<211> LENGTH: 30
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 179
acaucaagga agauggcauu ucuaguuugg                                   30

<210> SEQ ID NO 180
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 180
acaucaagga agauggcauu ucuag                                        25

<210> SEQ ID NO 181
<211> LENGTH: 30
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 181
cuccaacauc aaggaagaug gcauuucuag                                   30

<210> SEQ ID NO 182
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 182
aucauuuuuu cucauaccuu cugcu                                        25

<210> SEQ ID NO 183
<211> LENGTH: 36
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 183
```

```
aucauuuuuu cucauaccuu cugcuaggag cuaaaa                               36
```

<210> SEQ ID NO 184
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 184

```
cacccaccau cacccucugu g                                               21
```

<210> SEQ ID NO 185
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 185

```
aucaucucgu ugauauccuc aa                                              22
```

<210> SEQ ID NO 186
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 186

```
uccugcauug uugccuguaa g                                               21
```

<210> SEQ ID NO 187
<211> LENGTH: 30
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 187

```
uccaacuggg gacgccucug uuccaaaucc                                      30
```

<210> SEQ ID NO 188
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 188

```
acugggacg ccucuguucc a                                                21
```

<210> SEQ ID NO 189
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 189

```
ccguaaugau uguucuagcc                                                 20
```

-continued

<210> SEQ ID NO 190
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 190
uguuaaaaaa cuuacuucga                                               20

<210> SEQ ID NO 191
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 191
cauucaacug uugccuccgg uucugaaggu g                                  31

<210> SEQ ID NO 192
<211> LENGTH: 24
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 192
cuguugccuc cgguucugaa ggug                                          24

<210> SEQ ID NO 193
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 193
cauucaacug uugccuccgg uucug                                         25

<210> SEQ ID NO 194
<211> LENGTH: 21
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 194
uacuaaccuu gguuucugug a                                             21

<210> SEQ ID NO 195
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 195
cugaaggugu ucuuguacuu caucc                                         25

<210> SEQ ID NO 196

```
<211> LENGTH: 27
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 196
uguauaggga cccuccuucc augacuc                                          27

<210> SEQ ID NO 197
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 197
cuaaccuugg uuucugugau uuucu                                            25

<210> SEQ ID NO 198
<211> LENGTH: 27
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 198
gguaucuuug auacuaaccu ugguuuc                                          27

<210> SEQ ID NO 199
<211> LENGTH: 22
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 199
auucuuucaa cuagaauaaa ag                                               22

<210> SEQ ID NO 200
<211> LENGTH: 25
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 200
gauucugaau ucuuucaacu agaau                                            25

<210> SEQ ID NO 201
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 201
aucccacuga uucugaauuc                                                  20

<210> SEQ ID NO 202
<211> LENGTH: 22
<212> TYPE: DNA
```

<213> ORGANISM: Artificial Sequence
<220> FEATURE:
<223> OTHER INFORMATION: Human 2'-O-methyl phosphorothioate antisense
      oligonucleotide

<400> SEQUENCE: 202
uuggcucugg ccuguccuaa ga                                              22

<210> SEQ ID NO 203
<211> LENGTH: 29
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 203 cuuuuccag guucaagugg gauacuagc                                        29

<210> SEQ ID NO 204
<211> LENGTH: 31
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 204
caagcuuuuc uuuuaguugc ugcucuuuuc c                                    31

<210> SEQ ID NO 205
<211> LENGTH: 30
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 205
uauucuuuug uucuucuagc cuggagaaag                                      30

<210> SEQ ID NO 206
<211> LENGTH: 28
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 206
cugcuuccuc caaccauaaa acaaauuc                                        28

<210> SEQ ID NO 207
<211> LENGTH: 26
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 207
ccaaugccau ccuggaguuc cuguaa                                          26

<210> SEQ ID NO 208
<211> LENGTH: 20
<212> TYPE: DNA
<213> ORGANISM: Artificial Sequence
<220> FEATURE:

<223> OTHER INFORMATION: Human 2'-O-methyl phosphorothioate antisense
      oligonucleotide

<400> SEQUENCE: 208
uccuguagaa uacuggcauc                                                    20

<210> SEQ ID NO 209
<211> LENGTH: 27
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 209
ugcagaccuc cugccaccgc agauuca                                            27

<210> SEQ ID NO 210
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 210
cuaccucuuu uuucugucug                                                    20

<210> SEQ ID NO 211
<211> LENGTH: 20
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 211
uguuuuugag gauugcugaa                                                    20

<210> SEQ ID NO 212
<211> LENGTH: 84
<212> TYPE: DNA
<213> ORGANISM: Artificial Sequence
<220> FEATURE:
<223> OTHER INFORMATION: Human 2'-O-methyl phosphorothioate antisense
      oligonucleotide

<400> SEQUENCE: 212
cagcaguagu ugucaucugc ucaacuggca gaauucgauc caccggcugu ucaagccuga        60
gcugaucugc ucgcaucuug cagu                                               84

<210> SEQ ID NO 213
<211> LENGTH: 44
<212> TYPE: DNA
<213> ORGANISM: Homo sapiens

<400> SEQUENCE: 213
ucaugcacug agugaccucu uucucgcagg cgcuagcugg agca                         44

<210> SEQ ID NO 214
<211> LENGTH: 22

```
<212> TYPE: DNA
<213> ORGANISM: Homo sapiens

<400> SEQUENCE: 214
ccgugcagac ugacggucuc au                                        22
```